United States Patent
Kim et al.

(10) Patent No.: US 9,603,889 B2
(45) Date of Patent: Mar. 28, 2017

(54) IAP ANTAGONISTS

(71) Applicant: BRISTOL-MYERS SQUIBB COMPANY, Princeton, NJ (US)

(72) Inventors: Kyoung S. Kim, North Brunswick, NJ (US); Liping Zhang, East Windsor, NJ (US); Donna D. Wei, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/432,517

(22) PCT Filed: Oct. 1, 2013

(86) PCT No.: PCT/US2013/062781
§ 371 (c)(1),
(2) Date: Mar. 31, 2015

(87) PCT Pub. No.: WO2014/055461
PCT Pub. Date: Apr. 10, 2014

(65) Prior Publication Data
US 2015/0238558 A1  Aug. 27, 2015

Related U.S. Application Data

(60) Provisional application No. 61/708,828, filed on Oct. 2, 2012.

(51) Int. Cl.
| | | |
|---|---|---|
| *A61K 38/08* | (2006.01) |
| *C07K 5/083* | (2006.01) |
| *A61K 45/06* | (2006.01) |
| *C07K 7/06* | (2006.01) |
| *A61K 38/00* | (2006.01) |

(52) U.S. Cl.
CPC .............. *A61K 38/08* (2013.01); *A61K 45/06* (2013.01); *C07K 5/0806* (2013.01); *C07K 7/06* (2013.01); *A61K 38/00* (2013.01)

(58) Field of Classification Search
None
See application file for complete search history.

(56) References Cited

U.S. PATENT DOCUMENTS

| | | |
|---|---|---|
| 2011/0117081 A1 | 5/2011 | Laurent et al. |
| 2011/0177060 A1 | 7/2011 | Jaquith |
| 2012/0009141 A1 | 1/2012 | Laurent et al. |

FOREIGN PATENT DOCUMENTS

| | | |
|---|---|---|
| WO | WO2007131366 A1 * | 11/2007 |
| WO | WO2008128121 A1 * | 10/2008 |
| WO | WO2008128121 A1 * | 10/2008 |
| WO | WO 2011/059763 | 5/2011 |
| WO | WO2011059763 A2 * | 5/2011 |
| WO | WO2011059763 A2 * | 5/2011 |

OTHER PUBLICATIONS

Solanas, Concepcion et al, "Therapeutic index of gramicidin s is strongly modulated by d-phenylalanine analogues at the beta-turn." J. Med. Chem. (2009) 52 p. 664-674.*
Oost, Thorsein K. et al, "Discovery of potent antagonists of the antiapoptotic protein xiap for the treatment of cancer." J. Med. Chem. (2004) 47 p. 4417-4426.*

* cited by examiner

*Primary Examiner* — Fred Reynolds
(74) *Attorney, Agent, or Firm* — Elliott Korsen

(57) ABSTRACT

There are disclosed compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

1 Claim, No Drawings

IAP ANTAGONISTS

FIELD OF THE INVENTION

The invention relates generally to compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

BACKGROUND OF THE INVENTION

Apoptosis or programmed cell death is a genetically and biochemically regulated mechanism that plays an important role in development and homeostasis in invertebrates as well as vertebrates.

Aberrancies in apoptosis that lead to premature cell death have been linked to a variety of developmental disorders. Deficiencies in apoptosis that result in the lack of cell death have been linked to cancer and chronic viral infections.

Caspases are cysteine-containing aspartate specific proteases that play a key role in effecting apoptosis. Once activated from their inactive zymogen form by proteolytic processing, caspases digest vital cell proteins from within the cell. Since caspases are such strong proteases, tight control of this family of proteins is necessary to prevent premature cell death. In addition to proteolytic processing, caspases are also regulated by a family of molecules known as Inhibitors of Apoptosis Proteins (IAP). IAPs are naturally occurring intra-cellular proteins that suppress caspase-dependent apoptosis. SMAC, an intracellular protein also known as DIABLO, functions to modulate the activity of IAPs. In normal healthy cells, SMAC and IAPs function together to maintain healthy cells. However, in certain disease states, e.g., cancers and other proliferative disorders, the activities of IAPs are not adequately modulated and therefore, prevent apoptosis and cause or exacerbate abnormal proliferation and survival.

IAP antagonists, also known as SMAC mimetics, are synthetic molecules that mimic the structure and IAP modulating activity of the four N-terminal amino acids of SMAC (AVPI). When administered to a subject suffering proliferative disorders, the compounds antagonize IAP activities causing an increase in apoptosis among abnormally proliferating cells.

IAPs are found in all organisms ranging from *Drosophila* to human and are known to be overexpressed in many human cancers. IAPs comprise one to three Baculovirus IAP repeat (BIR) domains. The BIR domain is a zinc binding domain of about 70 residues comprising 4 alpha-helices and 3 beta strands, with cysteine and histidine residues that coordinate the zinc ion. The BIR2 and 3 domains contain a conserved inhibitor of apoptosis binding motif (IBM) capable of binding caspases- and inhibiting their proteolytic activity.

As an example, human X-chromosome linked IAP (XIAP) inhibits the executioner caspases-3, and -7 as well as the Apaf-1-cytochrome C mediated activation of the initiator caspase-9. Caspases-3 and -7 are inhibited by the BIR2 domain of XIAP, while the BIR3 domain of XIAP is responsible for the inhibition of caspase-9 activation. XIAP is expressed ubiquitously in most adult and fetal tissues. Overexpression of XIAP in tumor cells has been demonstrated to confer protection of the tumor cells against a variety of pro-apoptotic stimuli and promotes resistance to chemotherapy. Consistent with this, a strong correlation between XIAP protein levels and survival has been demonstrated for patients with acute myelogenous leukemia.

Other BIR2-3 containing IAP family members, while capable of binding caspases, do not directly inhibit their proteolytic activity. Rather they inhibit apoptosis by affecting signalling activities of key proteins in cell survival pathways. Like XIAP, these IAPs possess a carboxyl-terminal RING finger domain capable of conjugating ubiquitin to specific protein substrates. As an example, cellular IAPs 1 and 2 (cIAP1/2), ubiquitinate RIPK, a signalling intermediate of tumor necrosis death receptor (TNF-DR) activation. Ubiquitinated RIPK is unable to activate caspase-8 in the context of DR activation by TNF family DR ligands. On the contrary, the long ubiquitin chains attached to RIPK provide a scaffold by which cell components of the NFkB cell survival signalling cascade can attach and become activated.

In normal cells undergoing apoptosis, the IAP-mediated inhibition is removed by the mitochondrial protein SMAC (second mitochondrial activator of caspases; also known as DIABLO). SMAC is synthesized as a precursor molecule of 239 amino acids; the N-terminal 55 residues serving as the mitochondria targeting sequence that is removed after import. The mature form of SMAC resides in the intermembrane space of mitochondria. At the time of apoptosis induction, SMAC is released from mitochondria into the cytosol where, together with cytochrome c, it binds to XIAP, and eliminates its inhibitory effect on caspases. SMAC also binds cIAP1/2 and inhibits their ability to ubiquinate RIPK. SMAC interacts with essentially all IAPs that have been examined to date and thus appears to be a master regulator of apoptosis in mammals.

Down-regulation of XIAP expression by antisense oligonucleotides has been shown to sensitize tumor cells to death induced by a wide range of pro-apoptotic agents, both in vitro and in vivo. SMAC/DIABLO-derived peptides have also been demonstrated to sensitize a number of different tumor induced select cell lines to undergo apoptosis as single agents, while other cell lines require an additional stimulus such as DR agonists or co-treatment with pro-apoptotic drugs. Because IAP inhibition appears to be a viable mechanism for promoting apoptosis and treating diseases and conditions that are sensitive to apoptosis, there is a continuing need to develop compounds that can inhibit IAP.

SUMMARY OF THE INVENTION

There is provided compounds, methods of modulating the activity of IAP, and methods for treating various medical conditions using such compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in the treatment and/or prophylaxis of multiple diseases or disorders associated with IAP inhibition, such as cancer and other maladies.

The compounds of the invention may be used in therapy.

The compounds of the invention may be used for the manufacture of a medicament for the treatment and/or prophylaxis of multiple diseases or disorders associated with IAP inhibition.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

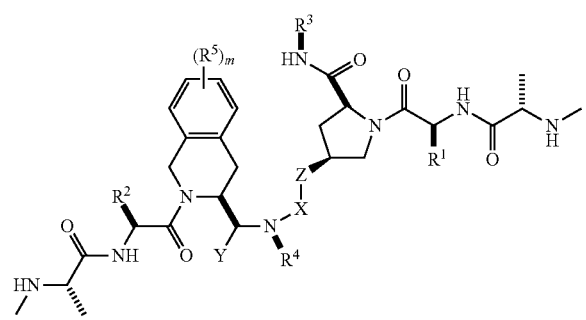

wherein:

Y is a carbonyl group (C=O) or is absent;

X is $-(CR^8R^9)_m-$, optionally substituted heteroaryl or optionally substituted heterocyclyl,

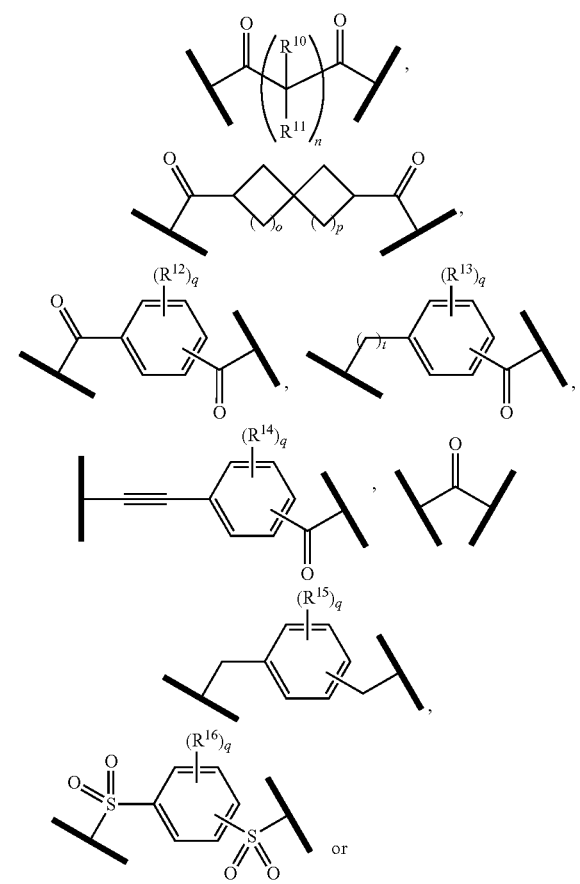

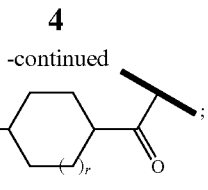

Z is C=O, —O—, —NR$^7$—, —CONH—, —NHCO— or may be absent;

R$^1$ and R$^2$ are independently optionally substituted alkyl, optionally substituted cycloalkyl, optionally substituted cycloalkylalkyl, optionally substituted thioalkyl, optionally substituted arylalkyl or optionally substituted aryl;

R$^3$ and R$^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$ is hydrogen, halogen, optionally substituted alkyl or OR$^6$;

R$^6$ is hydrogen, optionally substituted alkyl or optionally substituted cycloalkyl;

R$^7$ is hydrogen, optionally substituted alkyl or optionally substituted cycloalkyl;

R$^8$ and R$^9$ are independently hydrogen, halogen, optionally substituted alkyl or optionally substituted cycloalkyl; or R$^8$ and R$^9$ can be taken together to form a carbocyclic ring;

R$^{10}$ and R$^{11}$ are independently hydrogen, halogen or optionally substituted alkyl; or R$^8$ and R$^9$ can be taken together to form a carbocyclic ring;

R$^{12}$, R$^{13}$, R$^{14}$, R$^{15}$ and R$^{16}$ are independently hydrogen, halogen or optionally substituted alkyl or OR$^{17}$;

R$^{17}$ is hydrogen, optionally substituted alkyl or optionally substituted cycloalkyl;

m and n are independently 0, 1, 2, 3, or 4;

o and p are independently 0, 1, 2 or 3;

q and t are independently 0, 1, 2, 3, or 4;

r is 0 or 1;

and/or a pharmaceutically acceptable salt, tautomer or stereoisomer thereof.

In a second aspect, the invention provides a compound of Formula (I) within the scope of the first aspect, wherein:

Z is —NH— or —CONH—;

X is $-(CR^8R^9)_m-$, optionally substituted heteroaryl or optionally substituted heterocyclyl,

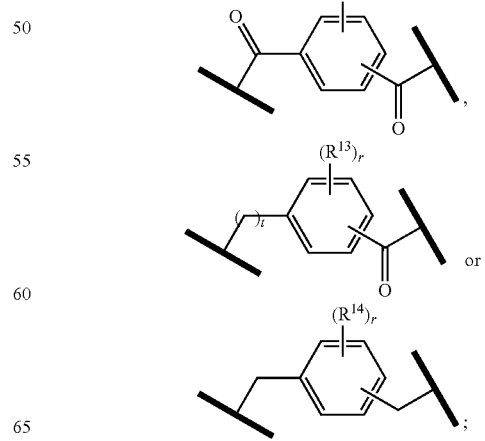

$R^1$ and $R^2$ are independently optionally substituted alkyl or optionally substituted thioalkyl;

$R^3$ and $R^4$ are independently optionally substituted alkyl, optionally substituted aryl or optionally substituted arylalkyl;

$R^5$ is hydrogen or alkyl;

$R^6$ is hydrogen;

$R^7$ is hydrogen or alkyl;

$R^8$ and $R^9$ are independently optionally substituted alkyl;

or a pharmaceutically acceptable salt, tautomer or stereoisomer thereof.

In a third aspect, there is provided a compound of Formula (I) within the scope of the first and second aspect, wherein:

$R^1$ and $R^2$ are independently t-butyl or methylthio;

$R^3$ and $R^4$ are independently optionally substituted phenyl or 1,2,3,4-tetrahydronaphthalenyl;

or a pharmaceutically acceptable salt, tautomer or stereoisomer thereof.

In a fourth aspect, the invention provides a compound of Formula (II)

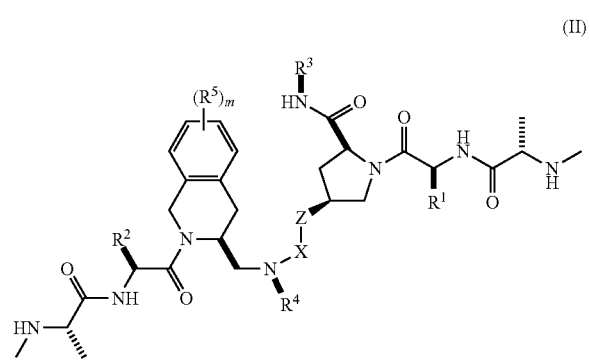

(II)

X is —(CR$^8$R$^9$)$_m$—, optionally substituted heteroaryl or optionally substituted heterocyclyl,

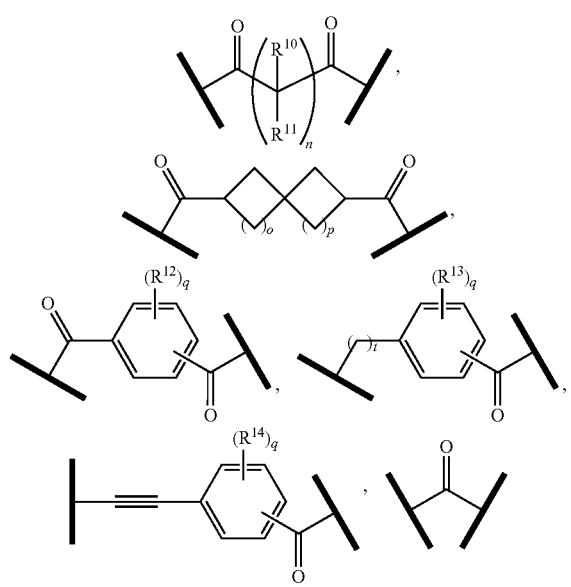

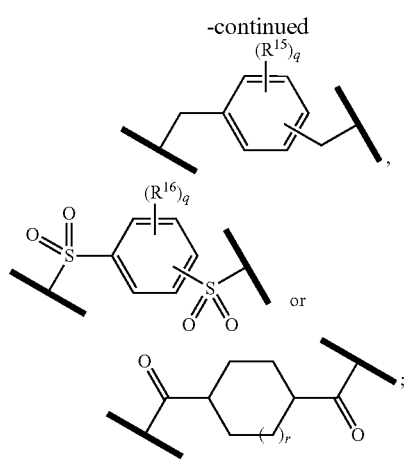

Z is C=O, —O—, —NR$^7$—, —CONH—, —NHCO— or may be absent;

$R^1$ and $R^2$ are independently optionally substituted alkyl, optionally substituted cycloalkyl, optionally substituted cycloalkylalkyl, optionally substituted thioalkyl, optionally substituted arylalkyl or optionally substituted aryl;

$R^3$ and $R^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$ is hydrogen, halogen, optionally substituted alkyl or OR$^6$;

$R^6$ is hydrogen, optionally substituted alkyl or optionally substituted cycloalkyl;

$R^7$ is hydrogen, optionally substituted alkyl or optionally substituted cycloalkyl;

$R^8$ and $R^9$ are independently hydrogen, halogen, optionally substituted alkyl or optionally substituted cycloalkyl; or $R^8$ and $R^9$ can be taken together to form a carbocyclic ring;

$R^{10}$ and $R^{11}$ are independently hydrogen, halogen or optionally substituted alkyl; or $R^8$ and $R^9$ can be taken together to form a carbocyclic ring;

$R^{12}$, $R^{13}$, $R^{14}$, $R^{15}$ and $R^{16}$ are independently hydrogen, halogen or optionally substituted alkyl or OR$^{17}$;

$R^{17}$ is hydrogen, optionally substituted alkyl or optionally substituted cycloalkyl;

m and n are independently 0, 1, 2, 3, or 4;

o and p are independently 0, 1, 2 or 3;

q and t are independently 0, 1, 2, 3, or 4;

r is 0 or 1;

and/or a pharmaceutically acceptable salt, tautomer or stereoisomer thereof.

In a fifth aspect, the invention provides a compound of Formula (II) within the scope of the fourth aspect, wherein:

Z is —NH— or —CONH—;

X is —(CR$^8$R$^9$)$_m$—, optionally substituted heteroaryl or optionally substituted heterocyclyl,

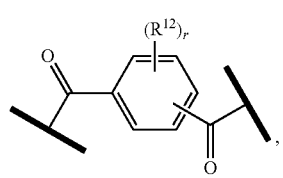

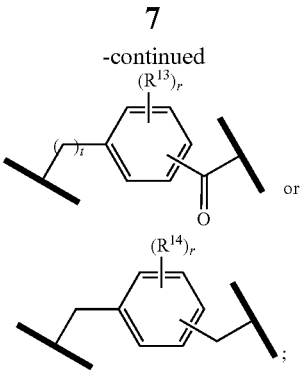

or

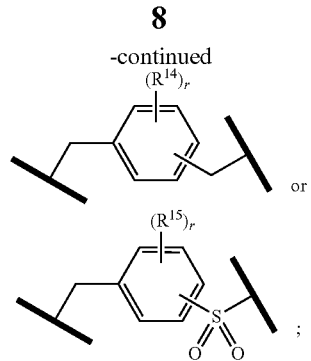

or

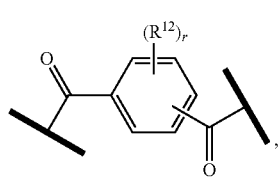

;

$R^1$ and $R^2$ are independently optionally substituted alkyl or optionally substituted thioalkyl;

$R^3$ and $R^4$ are independently optionally substituted alkyl, optionally substituted aryl or optionally substituted arylalkyl;

$R^5$ is hydrogen or alkyl;

$R^6$ is hydrogen;

$R^7$ is hydrogen or alkyl;

$R^8$ and $R^9$ are independently optionally substituted alkyl;

or a pharmaceutically acceptable salt, tautomer or stereoisomer thereof.

In a sixth aspect, there is provided a compound of Formula (II) within the scope of the fourth and fifth aspect, wherein:

$R^1$ and $R^2$ are independently t-butyl or methylthio;

$R^3$ and $R^4$ are independently optionally substituted phenyl or 1,2,3,4-tetrahydronaphthalenyl;

or a pharmaceutically acceptable salt, tautomer or stereoisomer thereof.

In a seventh aspect, the invention provides a compound of Formula (III)

(III)

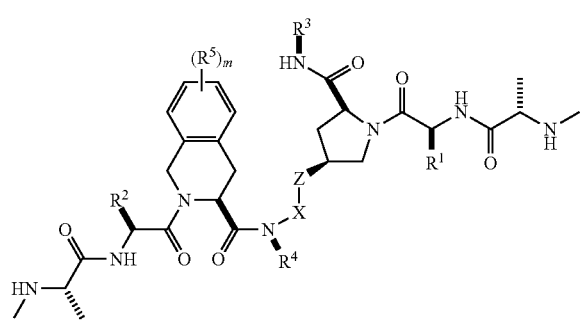

X is —$(CR^8R^9)_n$—, optionally substituted heteroaryl or optionally substituted heterocyclyl, Z is C=O, —O—, —$NR^7$—, —CONH—, —NHCO— or may be absent;

$R^1$ and $R^2$ are independently optionally substituted alkyl, optionally substituted cycloalkyl, optionally substituted cycloalkylalkyl, optionally substituted thioalkyl, optionally substituted arylalkyl or optionally substituted aryl;

$R^3$ and $R^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$ is hydrogen, halogen, optionally substituted alkyl or $OR^6$;

$R^6$ is hydrogen, optionally substituted alkyl or optionally substituted cycloalkyl;

$R^7$ is hydrogen, optionally substituted alkyl or optionally substituted cycloalkyl;

$R^8$ and $R^9$ are independently hydrogen, halogen, optionally substituted alkyl or optionally substituted cycloalkyl; or $R^8$ and $R^9$ can be taken together to form a carbocyclic ring;

$R^{10}$ and $R^{11}$ are independently hydrogen, halogen or optionally substituted alkyl; or $R^8$ and $R^9$ can be taken together to form a carbocyclic ring;

$R^{12}$, $R^{13}$, $R^{14}$, $R^{15}$ and $R^{16}$ are independently hydrogen, halogen or optionally substituted alkyl or $OR^{17}$;

$R^{17}$ is hydrogen, optionally substituted alkyl or optionally substituted cycloalkyl;

m and n are independently 0, 1, 2, 3, or 4;

o and p are independently 0, 1, 2 or 3;

q and t are independently 0, 1, 2, 3, or 4;

r is 0 or 1;

and/or a pharmaceutically acceptable salt, tautomer or stereoisomer thereof.

In an eighth aspect, the invention provides a compound of Formula (III) within the scope of the seventh aspect, wherein:

Z is —NH— or —CONH—;

X is —$(CR^8R^9)_m$—, optionally substituted heteroaryl or optionally substituted heterocyclyl,

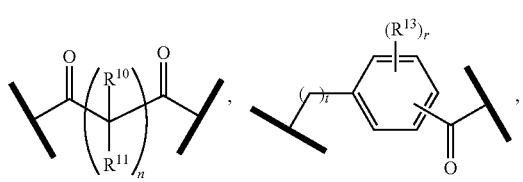

,

-continued

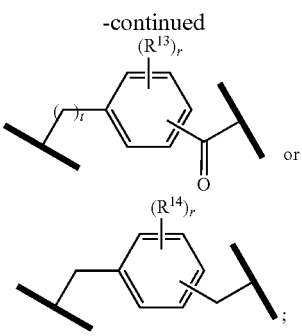

R¹ and R² are independently optionally substituted alkyl or optionally substituted thioalkyl;
R³ and R⁴ are independently optionally substituted alkyl, optionally substituted aryl or optionally substituted arylalkyl;
R⁵ is hydrogen or alkyl;
R⁶ is hydrogen;
R⁷ is hydrogen or alkyl;
R⁸ and R⁹ are independently optionally substituted alkyl;
or a pharmaceutically acceptable salt, tautomer or stereoisomer thereof.

In a ninth aspect, there is provided a compound of Formula (III) within the scope of the seventh and eighth aspect, wherein:
R¹ and R² are independently t-butyl or methylthio;
R³ and R⁴ are independently optionally substituted phenyl or 1,2,3,4-tetrahydronaphthalenyl;
or a pharmaceutically acceptable salt, tautomer or stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have BIR3 $IC_{50}$ values ≤0.40.
In another embodiment, the compounds of the invention have BIR3 $IC_{50}$ values ≤0.20.
In another embodiment, the compounds of the invention have BIR3 $IC_{50}$ values ≤0.10.
In another embodiment, the compounds of the invention have BIR3 $IC_{50}$ values ≤0.05.
In another embodiment, the compounds of the invention have BIR2 $IC_{50}$ values ≤3.00.
In another embodiment, the compounds of the invention have BIR2 $IC_{50}$ values ≤1.50.
In another embodiment, the compounds of the invention have BIR2 $IC_{50}$ values ≤0.50.
In another embodiment, the compounds of the invention have BIR2-3 $IC_{50}$ values ≤0.20.

II. Other Embodiments of the Invention

In another embodiment, there is provided a composition comprising one or more compounds of the present invention or a stereoisomer, a tautomer, a pharmaceutically acceptable salt, or a solvate thereof.

In another embodiment, there is provided a pharmaceutical composition comprising a pharmaceutically acceptable carrier and at least one of the compounds of the present invention or a stereoisomer, a tautomer, a pharmaceutically acceptable salt, or a solvate thereof.

In another embodiment, a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, there is provided a process for making a compound of the present invention or a stereoisomer, a tautomer, a pharmaceutically acceptable salt, or a solvate thereof.

In another embodiment, there is provided an intermediate for making a compound of the present invention or a stereoisomer, a tautomer, a pharmaceutically acceptable salt, or a solvate thereof.

In another embodiment, there is provided a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, there is provided a compound of the present invention for use in therapy.

In another embodiment, there is provided a combined preparation of a compound of the present invention and additional therapeutic agent(s) for simultaneous, separate or sequential use in therapy.

In another embodiment, there is provided a combined preparation of a compound of the present invention and additional therapeutic agent(s) for simultaneous, separate or sequential use in the treatment and/or prophylaxis of multiple diseases or disorders associated with the inhibition of apoptosis.

In another aspect, there is provided a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, there is provided a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, there is provided a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5)

solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

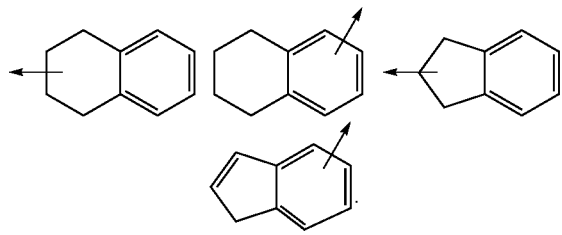

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heteroaryl" or "aromatic heterocyclic group" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As used herein, the term "heterocyclo", "heterocyclic" or "heterocyclyl" is intended to mean a 5-, 6- or 7-membered non-aromatic ring system containing from 1 to 4 heteroatoms selected from O, N or S. Examples of heterocycles include, but are not limited to, pyrrolidinyl, tetrahydrofuranyl, tetrahydropyranyl, piperidyl, pyrrolinyl, piperazinyl, imidazolinyl, morpholinyl, imidazolidinyl, pyrazolidinyl and pyrazolinyl.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWG include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6)

trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$ alkyl, $C_{1-6}$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_{1-6}$-alkoxycarbonyloxy-$C_{1-6}$-alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism, Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "therapeutically effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

Certain compounds of Formula I may generally be prepared according to the following Schemes 1 to 8. Tautomers and solvates (e.g., hydrates) of the compounds of Formula I are also within the scope of the present invention. Methods of solvation are generally known in the art. Accordingly, the compounds of the instant invention may be in the free or hydrate form, and may be obtained by methods exemplified by the following schemes.

The synthesis of key coupling partners 8, which can be used for the preparation of the heterodimeric compounds is outlined in Scheme 1. Fmoc-protected aminoproline 1 can be coupled to substituted amines 2 in the presence of coupling reagents, such as EDC and HOAt to afford amide intermediates 3. Removal of the N-Boc protecting group of 3 with, for example TFA followed by coupling of the resulting amine to various amino acids 4 provides protected dipeptides 5. Deprotection of 5 followed by coupling of the amine intermediate with various substituted amino acids 6 provides the protected peptides 7. Conversion of compounds 7 to the key intermediates 8 can be accomplished under basic conditions (e.g., piperidine).

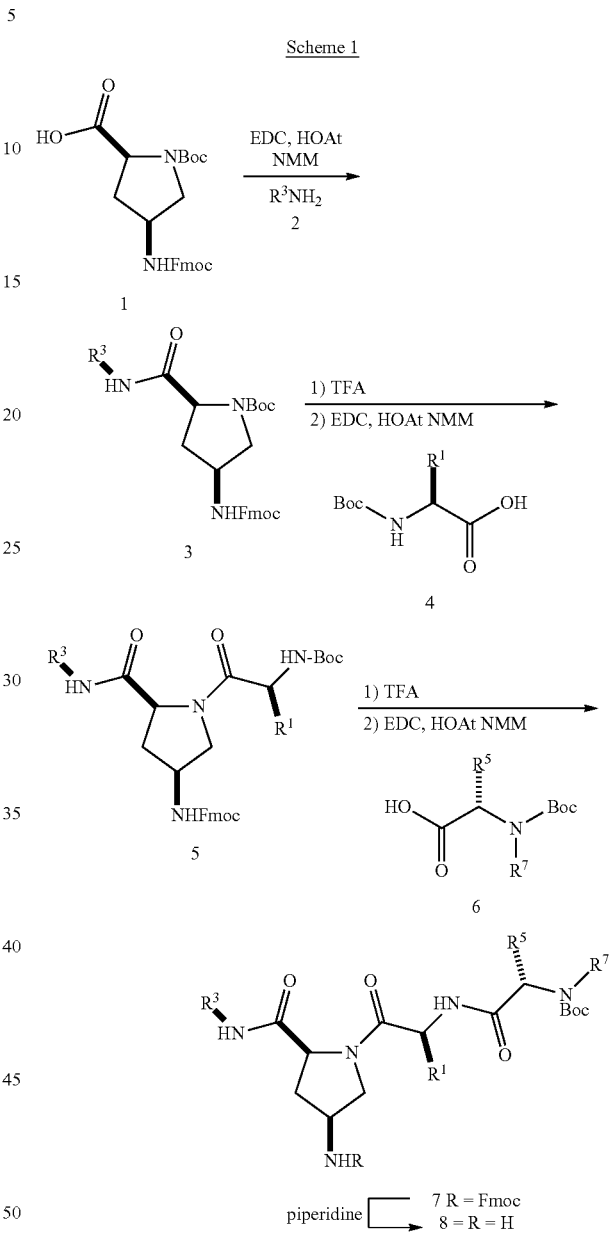

Heterodimeric amide analogs 22 can be prepared using the synthetic sequence outlined in Scheme 2. Benzylamine derivatives 11, derived from substituted amines 9 and methyl 4-(bromomethyl)benzoate (10), can be coupled to (S)-2-(tert-butoxycarbonyl)-1,2,3,4-tetrahydroisoquinoline-3-carboxylic acid (12) using standard amide bond forming conditions to afford intermediates 13. Removal of the N-Boc protecting group of 13 with, for example TFA followed by coupling of the intermediate amines 14 with amino acids 15 provides intermediates 16. Removal of the N-Boc protecting group of 16 followed by coupling of the requisite amines 17 with various amino acids 18 affords peptides 19. Base-promoted hydrolysis of ester 19 provides benzoic acids 20, which can be coupled with the key coupling partners 8 to furnish the heterodimers 21. Global deprotection of compounds 21 with, for example TFA provides the desired analogs 22.

Scheme 2

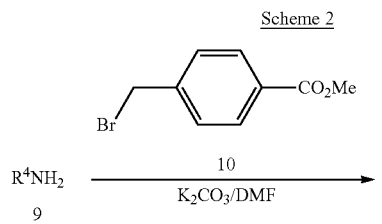

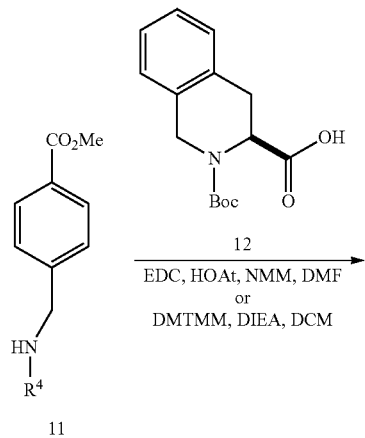

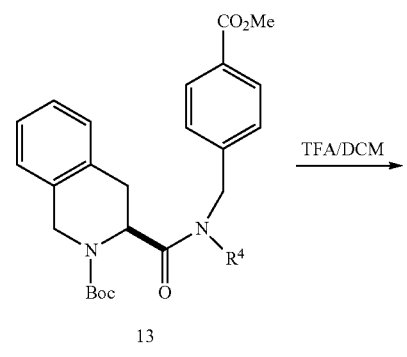

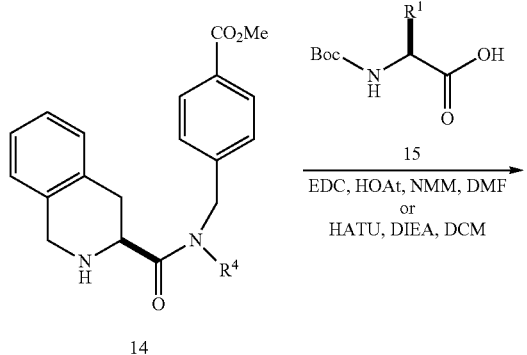

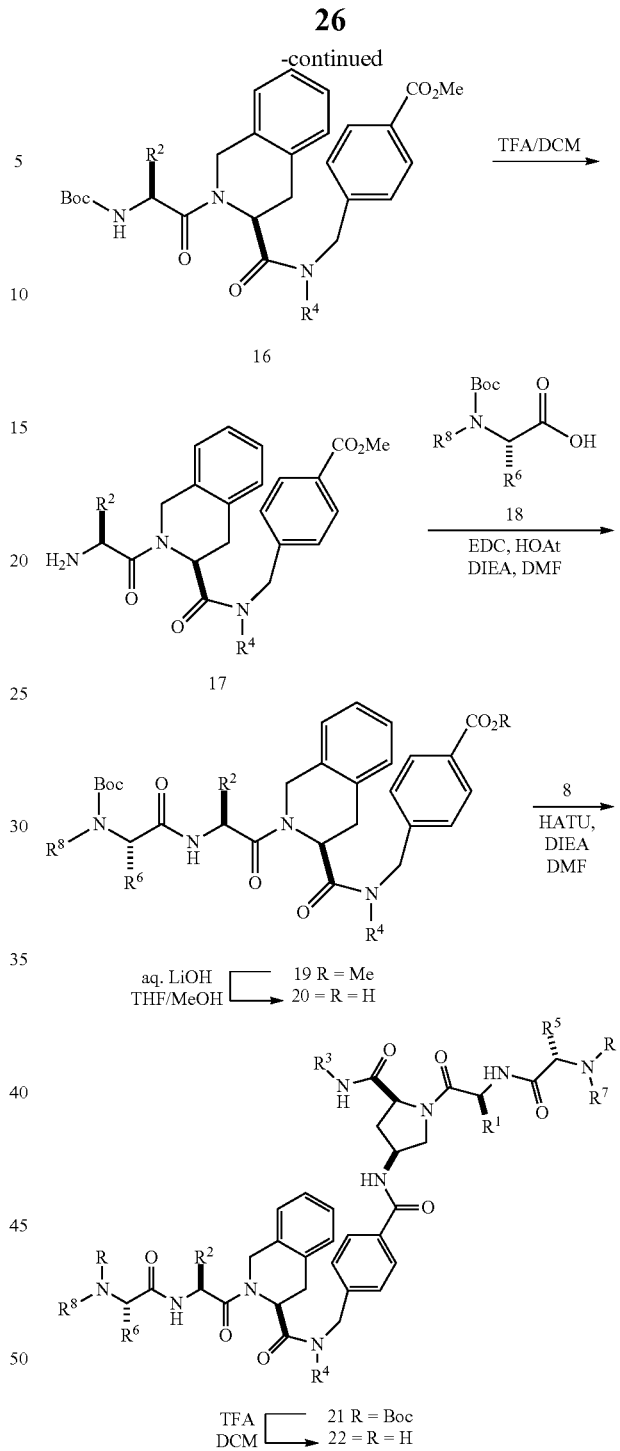

Alternatively, heterodimeric amide analogs 35 can be prepared according to the synthetic route illustrated in Scheme 3. Compounds 23, which can be obtained using similar chemistry as for the synthesis of compounds 13 (Scheme 2), can be hydrolyzed under basic conditions to afford acids 24. The coupling of 24 to proline derivative 25 can be accomplished using standard amide bond forming conditions to furnish intermediates 26. Hydrolysis of ester 26 followed by coupling of the resulting acids 27 with primary amines 2 affords compounds 28. Removal of the Cbz protecting group of 28 under hydrogenation conditions can furnish secondary amines 29. Removal of the N-Boc protecting group of compound 29 with, for example HCl followed by coupling of the intermediate amines with amino acid 30 provides intermediates 31. Removal of the N-Boc protecting groups of 31 followed by coupling of the resulting amines 32 with amino acid 33 provides intermediates 34. Global deprotection under acidic conditions affords the desired analogs 35.

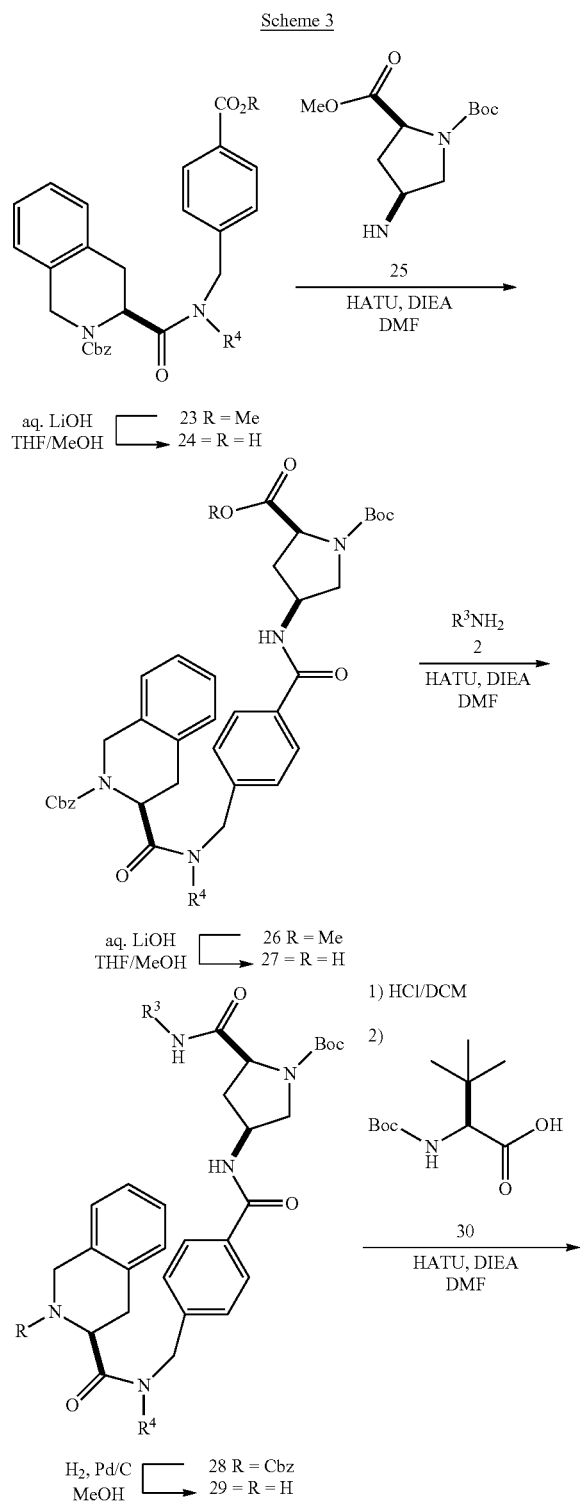

Scheme 3

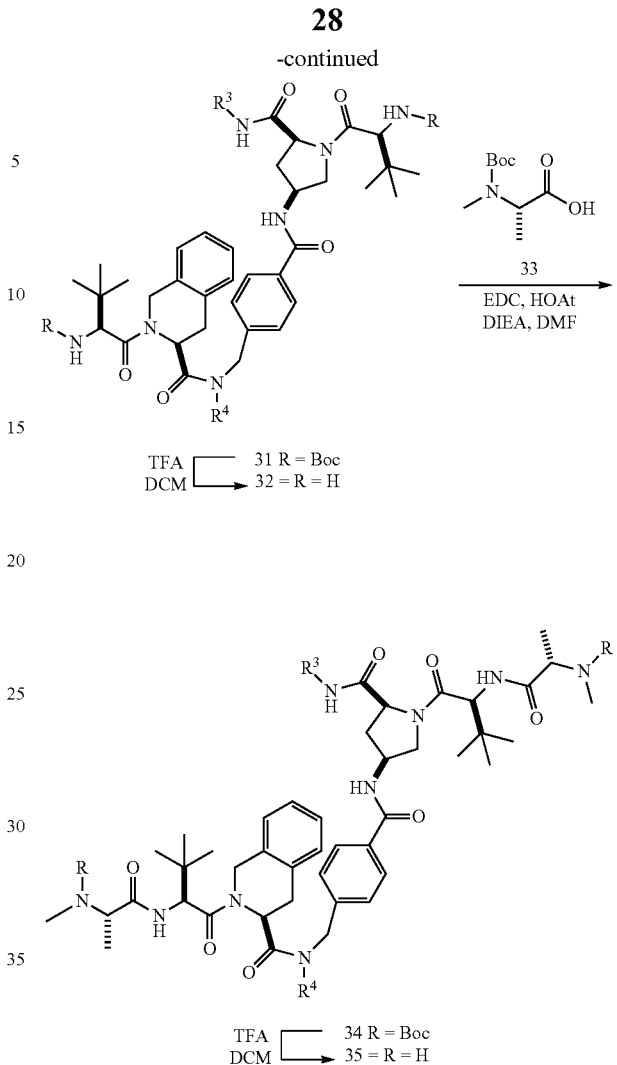

The required benzylamine derivatives 40 can be prepared using the synthetic route outlined in Scheme 4. (R)-tert-Butyl sulfinamide (36, Liu, G. et al., *J. Am. Chem. Soc.*, 119:9913-9914 (1997); Reddy, A. V. et al., *Syn. Comm.*, 39:1451-1456 (2009)) can be condensed with ketones 37 and the resulting imine can be reduced using, for example sodium borohydride at low temperature to provide intermediates 38. Removal of the chiral auxiliary on 38 under acidic conditions followed by reaction of the resulting secondary amine with methyl 4-(bromomethyl)benzoate (10) can furnish the necessary benzylamines 40.

Scheme 4

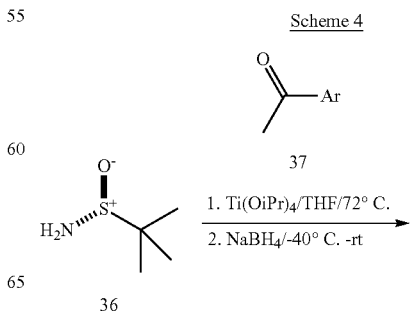

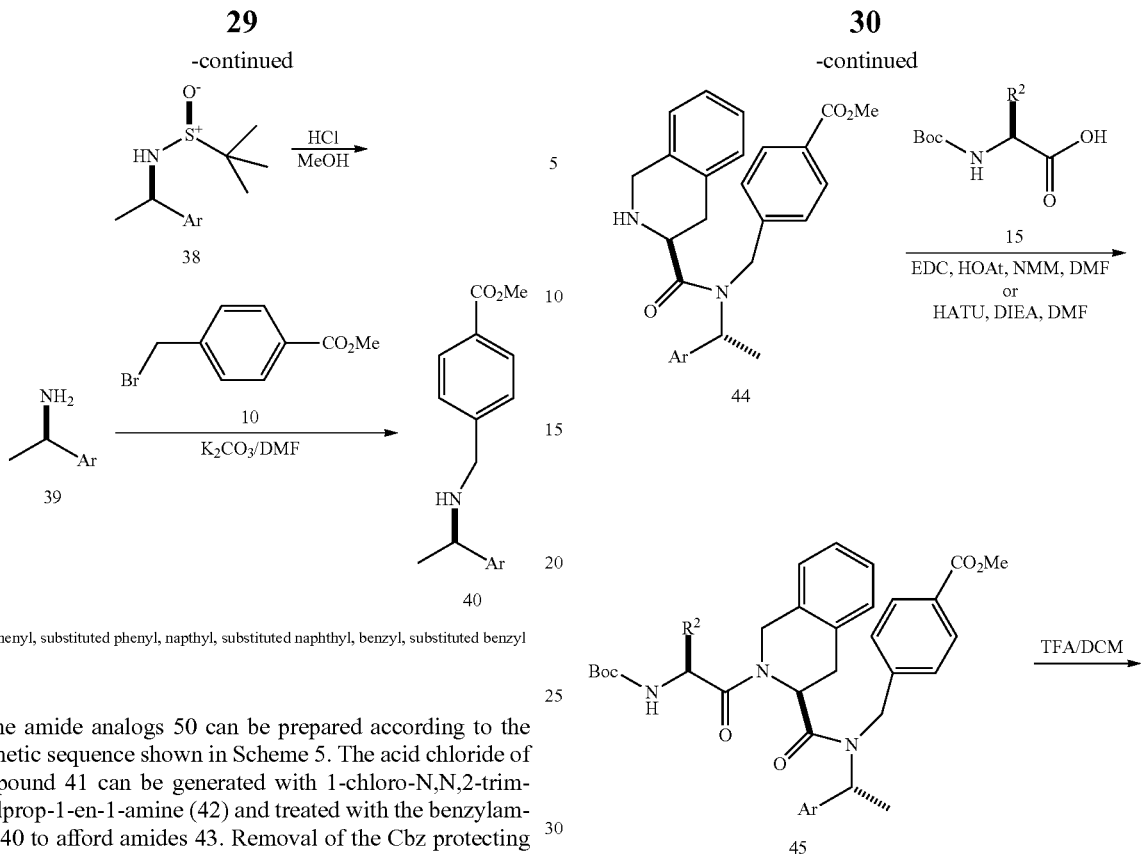

Ar = phenyl, substituted phenyl, napthyl, substituted naphthyl, benzyl, substituted benzyl The amide analogs 50 can be prepared according to the synthetic sequence shown in Scheme 5. The acid chloride of compound 41 can be generated with 1-chloro-N,N,2-trimethylprop-1-en-1-amine (42) and treated with the benzylamines 40 to afford amides 43. Removal of the Cbz protecting group of 43 under hydrogenation conditions or boron tribromide provides the secondary amines 44. Conversion of compounds 44 to the desired analogs 50 can be accomplished using the same chemistry as outlined in Scheme 3.

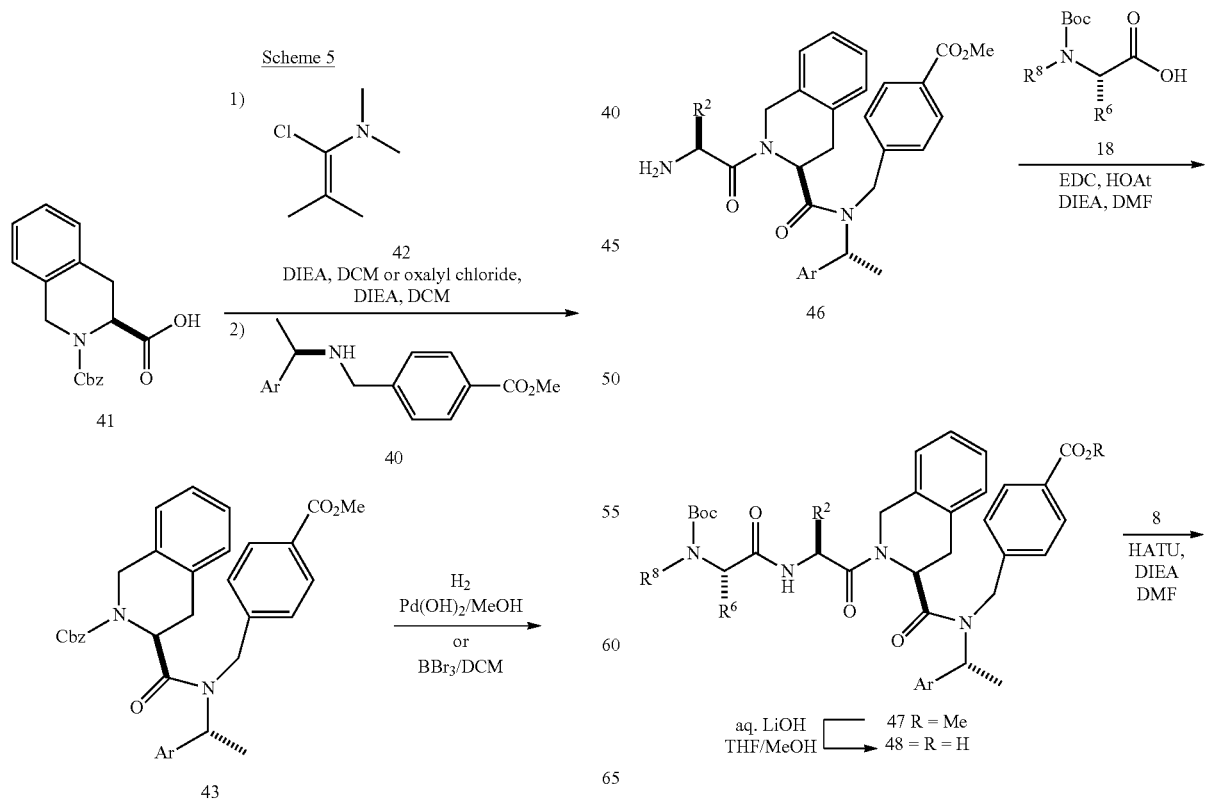

-continued

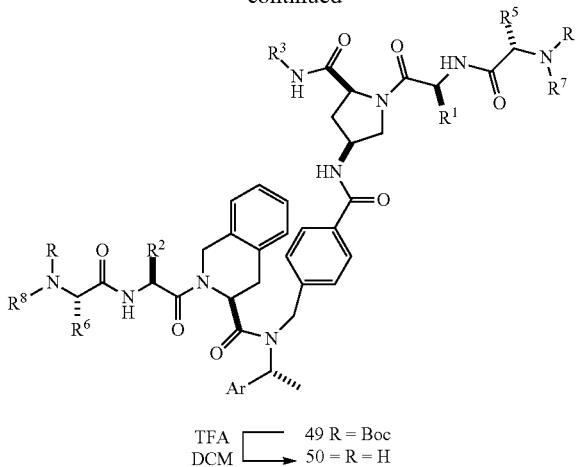

TFA, DCM: 49 R = Boc → 50 R = H

Ar = phenyl, substituted phenyl, naphthyl, substituted naphthyl, benzyl, substituted benzyl The amide analogs 63 can be prepared according to the synthetic sequence shown in Scheme 6. The acid chloride of compound 41 can be generated with 1-chloro-N,N,2-trimethylprop-1-en-1-amine (42) and treated with the secondary amine 51 to afford the indole intermediate 54. Reductive amination between benzylamine derivative 52 and indole aldehyde 53 provides the required indole amine starting material 51. Deprotonation of indole 54 with sodium hydride affords the sodium salt 55. The activated carbamate of peptides 8 can be generated with 4-nitrophenyl carbonochloridate (56) and treated with compound 55 to furnish intermediates 57. Removal of the Cbz protecting group of 57 under hydrogenation conditions provides the secondary amines 58, which can be coupled with various amino acids 59 to furnish intermediates 60. Cleavage of the Fmoc group of 60 with piperidine, followed by coupling of the amines 61 with amino acids 18 provides compounds 62. Global deprotection of 62 affords the desired analogs 63.

Scheme 6

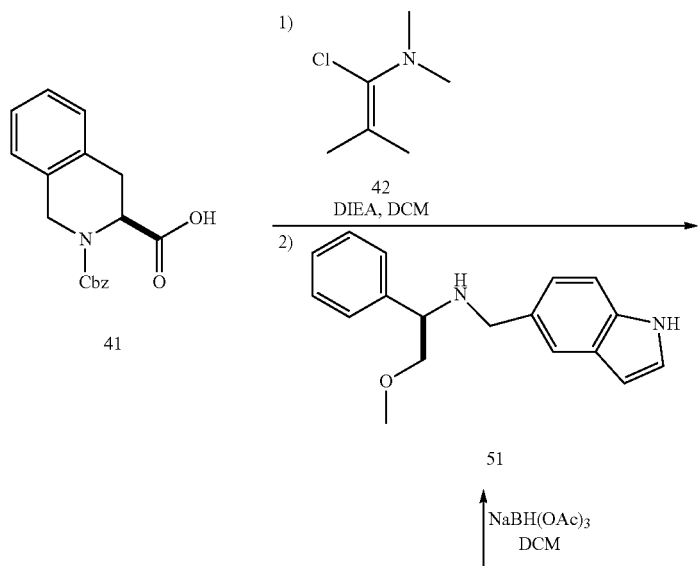

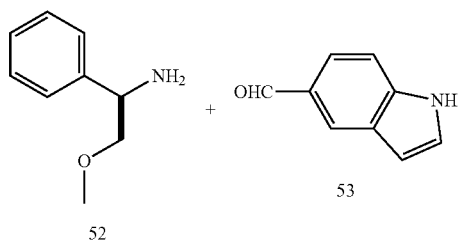

-continued
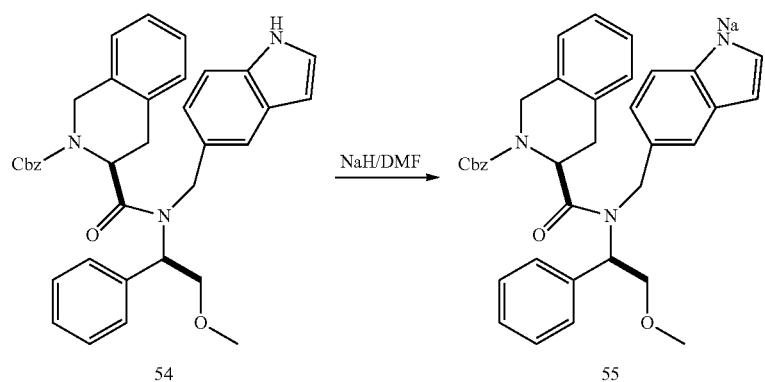
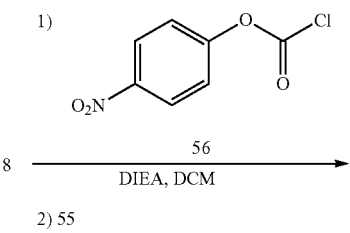
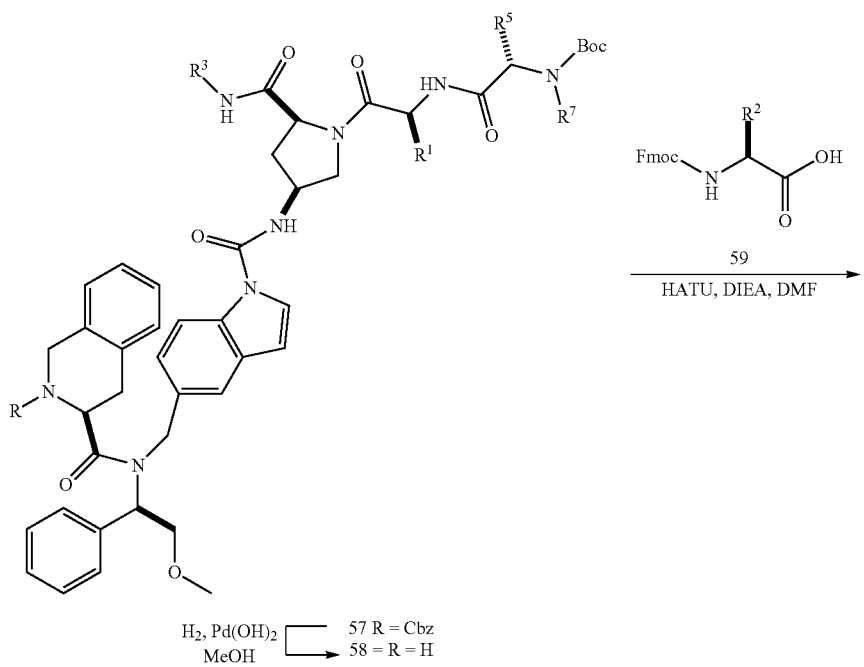

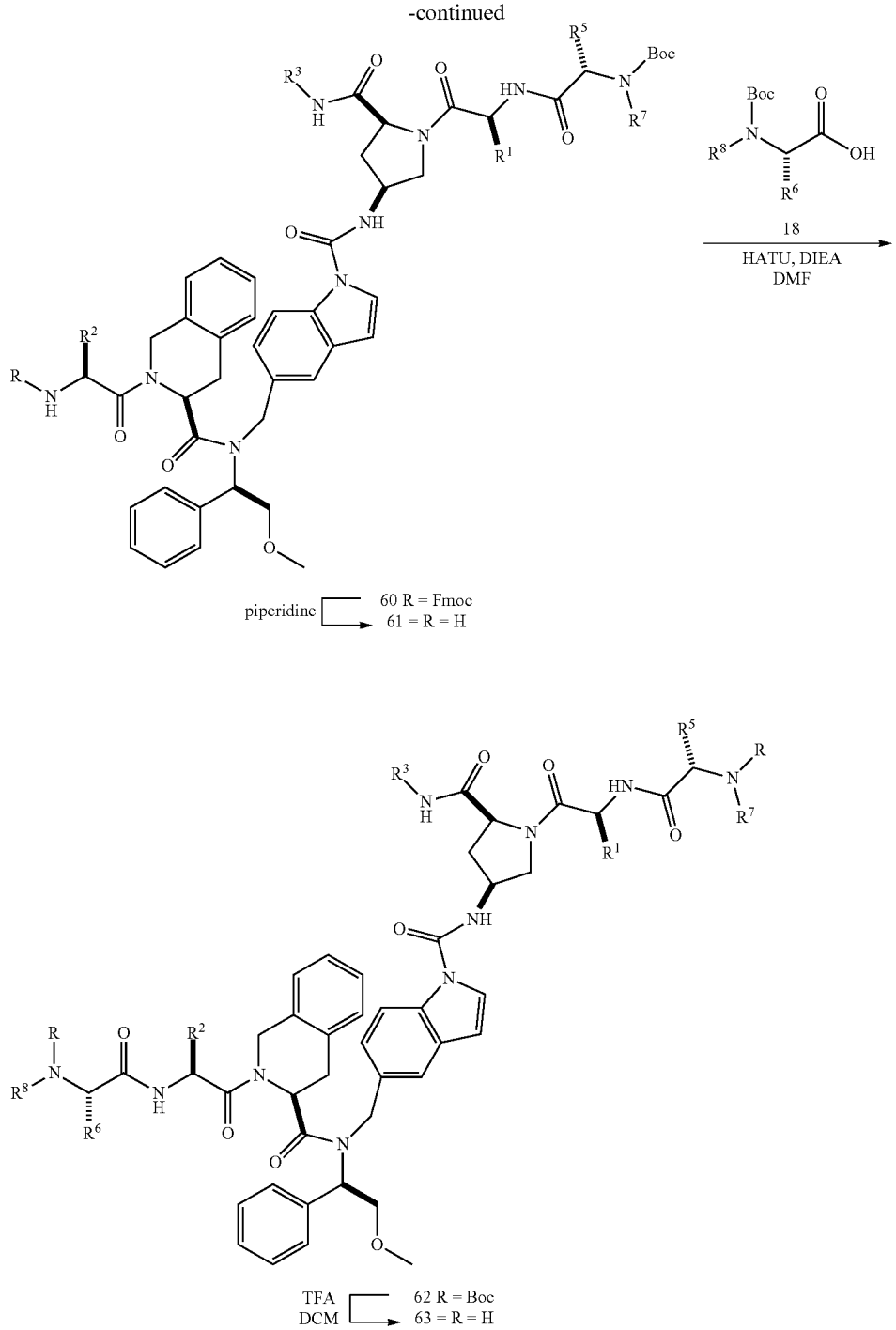

The terephthalamide analogs 75 can be prepared according to the synthetic sequence outlined in Scheme 7. Removal of the Boc protecting group of tetrahydroisoquinoline derivative 64 under acidic conditions provides the secondary amine 65, which can be coupled with various amino acids 15 to furnish intermediates 66. Deprotection of compounds 66 followed by coupling of the resulting amine 67 with amino acids 18 can provide intermediates 68. Oxidation of the primary alcohols 68 with, for example Dess-Martin periodinane, provides aldehydes 69. Compound 69 can undergo reductive amination with substituted amines 9 in the presence of sodium triacetoxyborohydride to afford peptides 70. Amide 72, derived from amine 70 and methyl 4-(chlorocarbonyl)benzoate (71) can be hydrolyzed under basic conditions to furnish benzoic acid derivatives 73. Coupling of compound 73 with peptides 8 followed by deprotection of the resulting intermediate 74 under acidic conditions affords the desired analogs 75.

Scheme 7

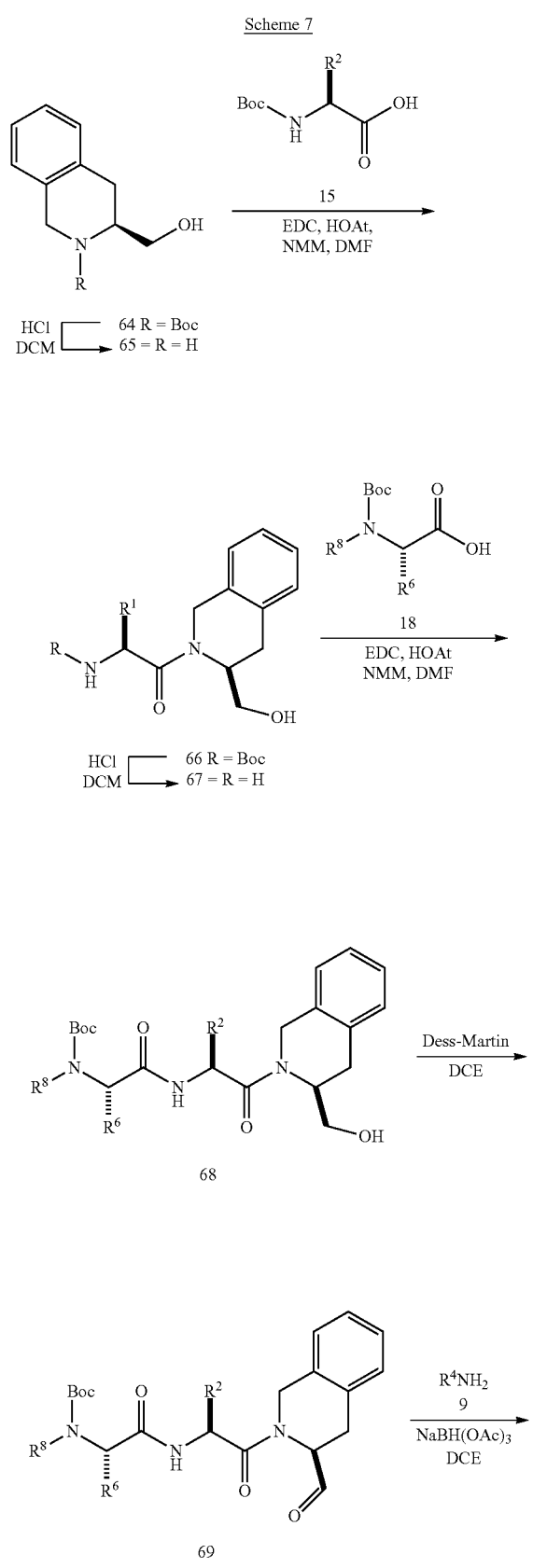

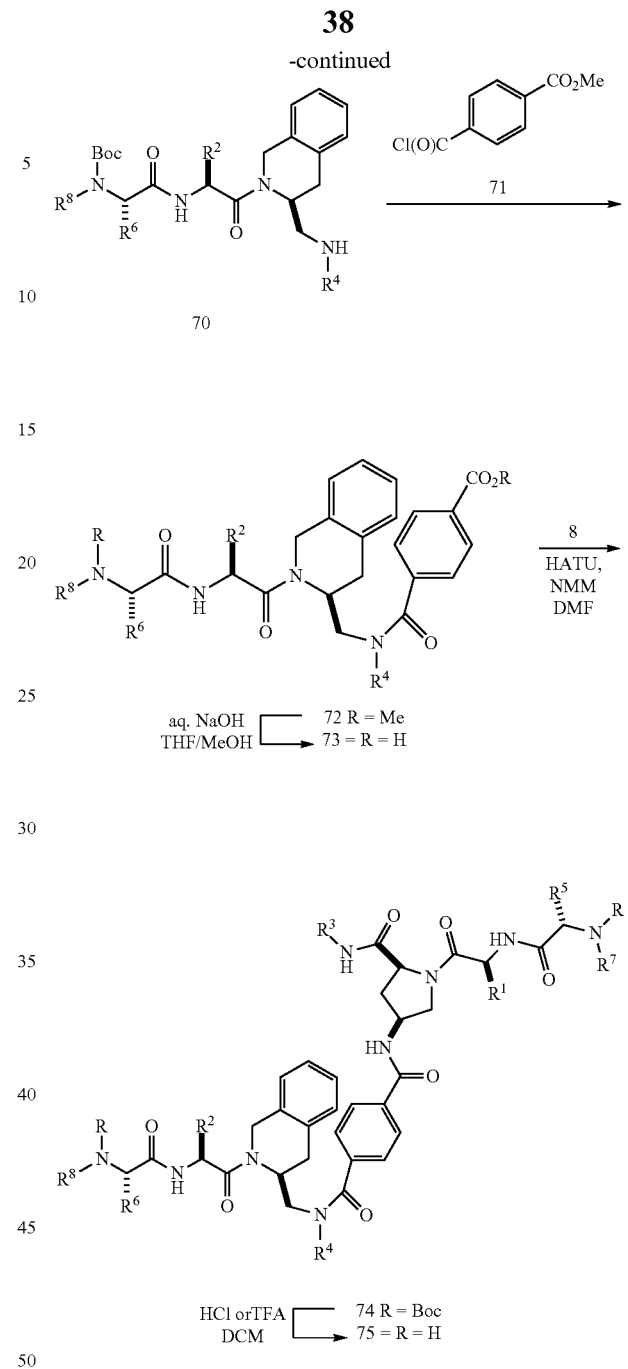

The amide analogs 85 can be prepared according to the synthetic sequence shown in Scheme 8. Intermediate 78, prepared in a similar manner as compound 54 (Scheme 6) was hydrolyzed under basic conditions to provide acid 79. Compound 79 was coupled to peptides 8 using conditions described previously to furnish amides 80. Removal of the Cbz protecting group of 80 under hydrogenation conditions provides the secondary amines 81, which can be coupled with various amino acids 59 to furnish intermediates 82. Cleavage of the Fmoc group of 82 with piperidine, followed by coupling of the resulting amine 83 with amino acids 18 provides compounds 84. Global deprotection of 84 affords the desired analogs 85.

Scheme 8
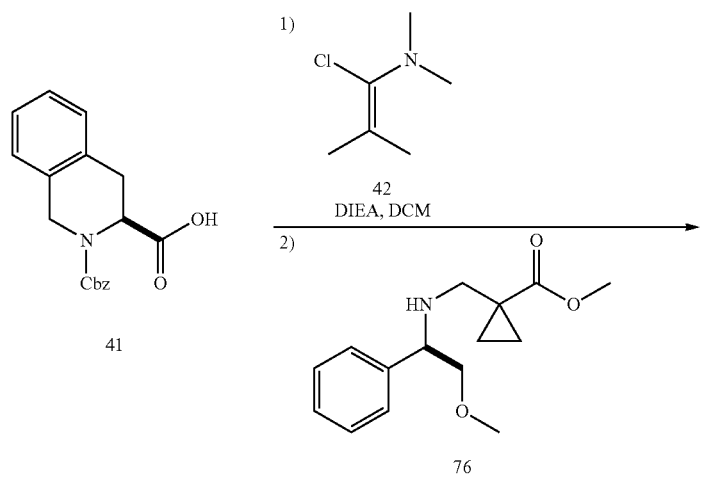
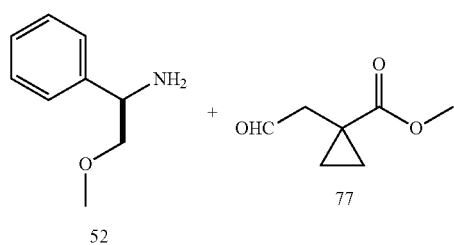
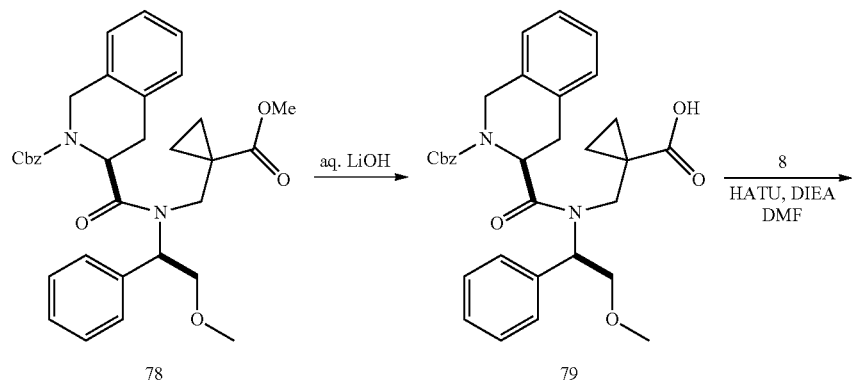

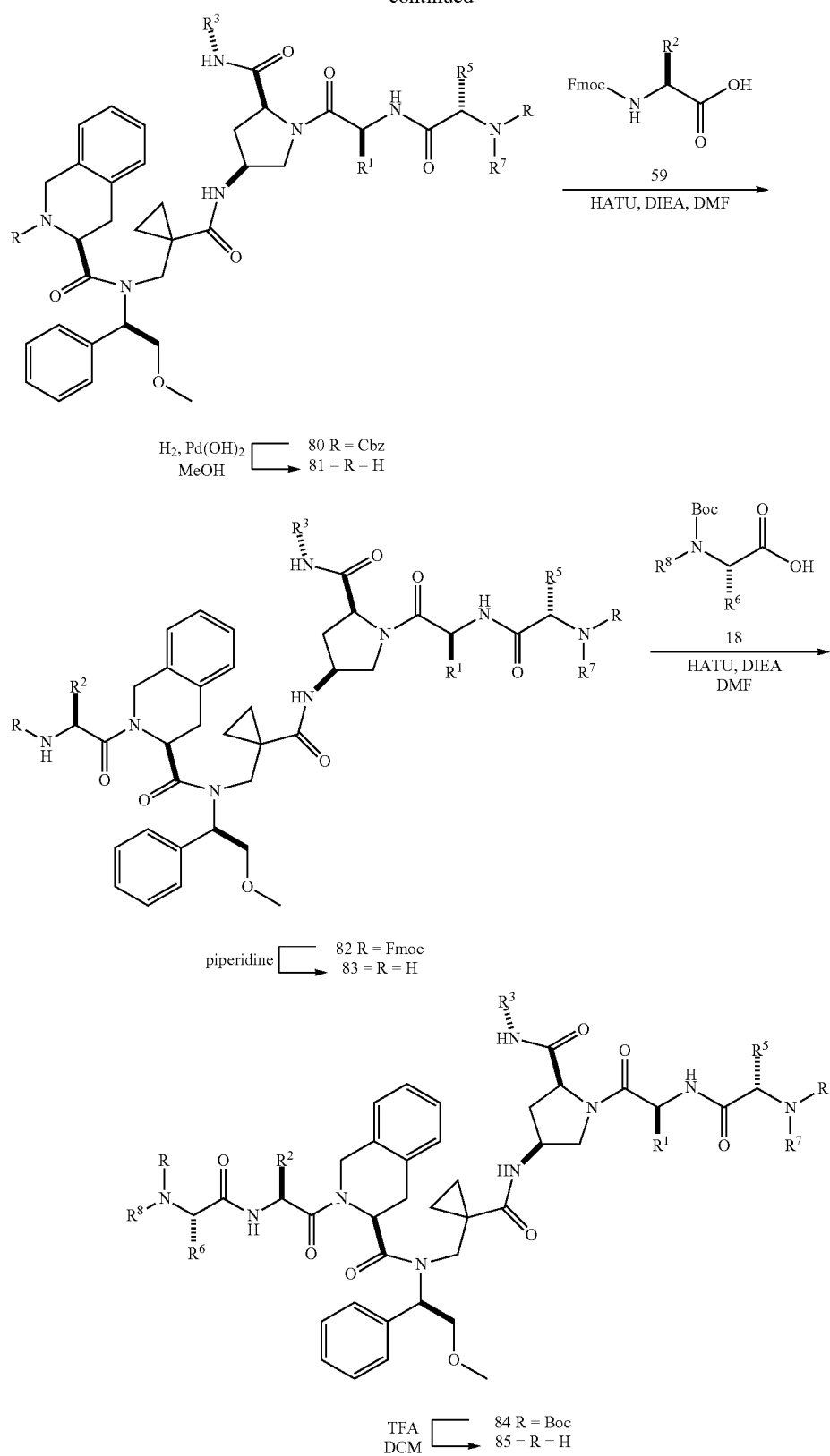

EXAMPLES

General Experimental

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked REDISEP® R$_f$ silica gel columns on a CombiFlash Companion machine.

Preparative Reverse Phase HPLC was performed with a linear gradient elution using H$_2$O/MeOH or H$_2$O/MeCN mixtures buffered with 0.1% trifluoroacetic acid or 10 mM NH$_4$OAc and detection at 220 nm on one of the following columns: Shimadzu Sunfire S10 30×250 mm (flow rate=40 mL/min), or C18 PHENOMENEX® Luna S5 ODS 21×100 mm (flow rate=20 mL/min), or YMC S5 ODS 20×100 mm (flow rate=20 mL/min) or Waters XBridge C18 19×250 mm (flow rate=20 mL/min). Preparative Supercritical Fluid Chromatography (SFC) was performed using 78% CO$_2$/MeOH buffered with 0.1% diethylamine and detection at 220 nm on a CHIRALPAK® AS-H IDS 25×3 cm column (flow rate=85 mL/min).

All final products were characterized by $^1$H NMR, RP HPLC and electrospray ionization (ESI) or atmospheric pressure ionization (API) mass spectrometry (MS). $^1$H NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

Abbreviations

Ac acetyl
AcOH acetic acid
Ac$_2$O acetic anhydride
ADDP 1,1'-(azodicarbonyl)dipiperidine
aq. aqueous
Bn benzyl
Boc t-butyl carbamate
Boc$_2$O di-t-butyl dicarbonate
Bu butyl
Bu$_4$NI tetrabutylammonium iodide
Cbz carboxybenzyl
CDI 1,1'-carbonyldiimidazole
conc. concentrated
DBU 1,8-diazabicyclo[5.4.0]undec-7-ene
DCE dichloroethane
DCM dichloromethane
DDQ 2,3-dichloro-5,6-dicyano-1,4-benzoquinone
DIAD diisopropyl azodicarboxylate
DIEA diisopropylethylamine
DMAP 4-N,N-dimethylaminopyridine
DMF dimethyl formamide
DMSO dimethyl sulfoxide
DMTMM 4-(4,6-dimethoxy-1,3,5-triazin-2-yl)-4-methylmorpholinium chloride
EDC 1-(dimethylaminopropyl)-3-ethylcarbodiimide hydrochloride
Et ethyl
EtOAc ethyl acetate
EtOH ethanol
Et$_2$O diethyl ether
Et$_3$N triethyl amine
h hour(s)
HATU O-(7-azabenzotriazol-1-yl)-N,N,N',N'-tetramethyluronium hexafluorophosphate
HNBu$_2$ dibutyl amine
H$_2$NNHBn 1-benzylhydrazine
HOAt 1-hydroxy-7-azabenzotriazole
HPLC high pressure liquid chromatography
i-PrOH isopropanol
i-Pr$_2$EtN di(isopropyl)ethylamine
KOAc potassium acetate
min minute(s)
m-CPBA m-chloro-3-chloroperbenzoic acid
Me methyl
MeCN acetonitrile
MeOH methanol
Me$_2$NH dimethyl amine
MTBE methyl tert-butyl ether
Na(OAc)$_3$BH sodium triacetoxyborohydride
NaSEt sodium ethanethiolate
NBS N-bromosuccinimide
n-BuLi n-butyl lithium
NCS N-chlorosuccinimide
NMM N-methylmorpholine
NMP n-methylpyrrolidinone
NMR nuclear magnetic resonance
OTBDPS tert-butyldiphenylsilyloxy
OTf trifluoromethylsulfonyloxy
Pd/C palladium on carbon
Pd(dppf)$_2$Cl$_2$ [1,1'-bis(diphenylphosphino)ferrocene]dichloropalladium(II)
Pd(OAc)$_2$ palladium acetate
Pd(PPh$_3$)$_4$ tetrakis(triphenylphosphine)palladium
Pd$_2$(dba)$_3$ tris(dibenzylideneacetone)dipalladium(0)
Ph phenyl
PhI(OAc)$_2$ phenyl iodoacetate
PhMe toluene
Ph$_2$TfN 1,1,1-trifluoro-N-phenyl-N-(trifluoromethyl)sulfonyl methanesulfonamide
PPh$_3$ triphenyl phosphorus
sat. saturated
SEM (trimethylsilyl)ethoxy)methyl
SEM-Cl (trimethylsilyl)ethoxy)methyl chloride
TBAF tetrabutylammonium fluoride
TBAI tetrabutylammonium iodide
TBSO tert-butyldimethylsilyloxy
t-Bu tertiary butyl
t-BuOH tertiary butanol
t-BuOK potassium tertiary-butoxide
tert-BuOH tertiary butanol
TFA trifluoroacetic acid
Tf$_2$O trifluoromethylsulfonic anhydride
THF tetrahydrofuran
TMS trimethylsilyl
THP tetrahydro-2H-pyran-2-yl
TMS-OTf trimethylsilyl triflate
TsO p-toluenesulfonyl

Example 1

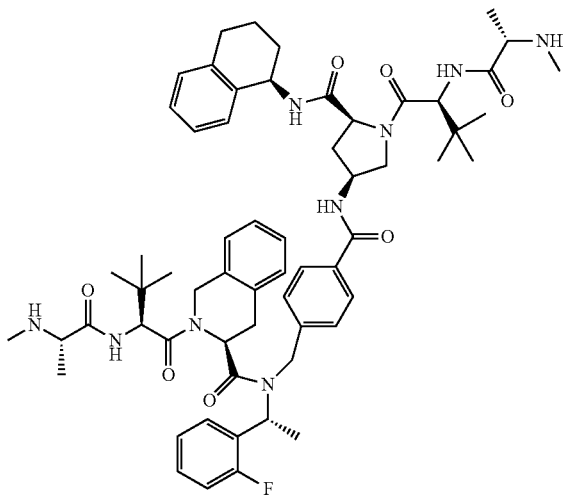

(S)-N-(4-(((3S,5S)-1-((S)-3,3-Dimethyl-2-((R)-2-(methylamino)propanamido)butanoyl)-5-(((R)-1,2,3,4-tetrahydronaphthalen-1-yl)carbamoyl)pyrrolidin-3-yl)carbamoyl)benzyl)-2-((S)-3,3-dimethyl-2-((S)-2-(methylamino)propanamido)butanoyl)-N-((R)-1-(2-fluorophenyl)ethyl)-1,2,3,4-tetrahydroisoquinoline-3-carboxamide

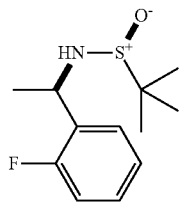 [SMILES: C[C@@H](N[S@@+]([O-])C(C)(C)C)c1ccccc1F]

A) N-((R)-1-(2-Fluorophenyl)ethyl)-2-methylpropane-2-sulfinamide

To a solution of 1-(2-fluorophenyl)ethanone (6.84 g, 49.5 mmol) in anhydrous THF (50 mL) at rt was added Ti(iOPr)$_4$ (25 mL) followed by solid (R)-tert-butyl sulfinamide (5.00 g, 41.3 mmol, source: Oakwood) under N$_2$ atm (Reference: *Syn. Comm.*, 39:1451-1456 (2009); *Tet. Lett.*, 40:6709-6712 (1999)). The reaction mixture was heated at 73° C. for 15 h, cooled to −70° C. and treated with NaBH$_4$ (1.6 g). The reaction mixture was stirred for 7 h, slowly warmed to −10° C. and slowly diluted with MeOH (20 mL) followed by EtOAc and brine. The solid that formed was filtered through a pad of CELITE®, washed with EtOAc and the filtrate was concentrated in vacuo to obtain 10.1 g of crude mixture of products. This material was purified by column chromatography (eluting with hexanes/EtOAc) to obtain the title compound (4.35 g, 43.3% yield) as a white solid. $^1$H NMR (CDCl$_3$) δ 7.38 (td, J=7.6, 1.8 Hz, 1H), 7.26-7.21 (m, 1H), 7.18-7.11 (m, 1H), 7.05 (ddd, J=10.6, 8.2, 1.2 Hz, 1H), 4.81 (dd, J=6.6, 5.3 Hz, 1H), 3.54 (d, J=4.4 Hz, 1H), 1.55 (d, J=6.6 Hz, 3H), 1.24 (s, 9H); MS(ESI$^+$) m/z 244.2 (M+H)$^+$.

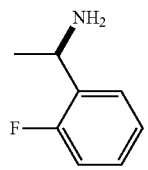

B) (R)-1-(2-Fluorophenyl)ethanamine

To a solution of N-((R)-1-(2-fluorophenyl)ethyl)-2-methylpropane-2-sulfinamide (4.35 g) in MeOH (20 mL) was added 4 N HCl in dioxane (15 mL) at rt. After 1.5 h, the reaction mixture was concentrated in vacuo and triturated with ether. The resulting solid was filtered, washed with ether and dried to obtain the title compound as a HCl salt (3.1 g, 17.7 mmol, 42.8% yield) as a white solid. $^1$H NMR (CD$_3$OD) δ 7.56-7.22 (m, 4H), 4.76 (q, J=7.0 Hz, 1H), 1.68 (d, J=7.0 Hz, 3H); MS(ESI$^+$) m/z 279.1 (M+H)$^+$.

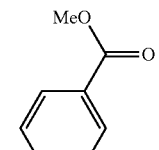

C) (R)-Methyl 4-(((1-(2-fluorophenyl)ethyl)amino)methyl)benzoate (R)-1-(2-Fluorophenyl)ethanamine, HCl salt (253 mg, 1.44 mmol) was dissolved in saturated aq. NaHCO$_3$ solution and the resulting suspension was extracted with ethyl acetate (twice). The organic layers were combined and dried over MgSO$_4$. The filtrate was concentrated in vacuo. To the residue was added DMF (6 mL), methyl 4-(bromomethyl)benzoate (300 mg, 1.31 mmol) and K$_2$CO$_3$ (452 mg, 3.27 mmol). The resulting suspension was stirred at rt for 3 h. The reaction mixture was diluted with ethyl acetate and brine. The organic layer was separated and dried over MgSO$_4$. The filtrate was concentrated in vacuo and the residue was purified by flash column chromatography (eluting with 25% EtOAc/hexanes) to afford the title compound as a colorless oil (0.30 g, 78%). $^1$H NMR (CDCl$_3$) δ 8.11-7.90 (m, 2H), 7.44 (td, J=7.6, 1.8 Hz, 1H), 7.38 (d, J=8.1 Hz, 2H), 7.27-7.20 (m, 1H), 7.18-7.11 (m, 1H), 7.04 (ddd, J=10.7, 8.0, 1.1 Hz, 1H), 4.15 (q, J=6.6 Hz, 1H), 3.91 (s, 3H), 3.78-3.62 (m, 2H), 1.67 (br. s., 1H), 1.42 (d, J=6.6 Hz, 3H); MS(ESI$^+$) m/z 288.2 (M+H)$^+$.

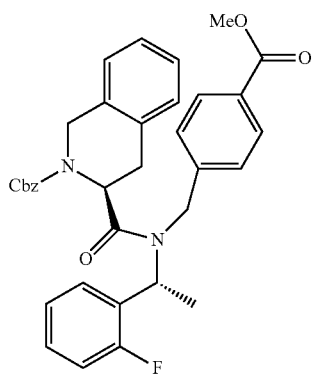 [SMILES: COC(=O)c1ccc(CN(C(=O)[C@@H]2Cc3ccccc3CN2C(=O)OCc2ccccc2)[C@H](C)c2ccccc2F)cc1]

D) (S)-Benzyl 3-(((R)-1-(2-fluorophenyl)ethyl)(4-(methoxycarbonyl)benzyl)carbamoyl)-3,4-dihydroisoquinoline-2(1H)-carboxylate To a solution of (S)-2-((benzyloxy)carbonyl)-1,2,3,4-tetrahydroisoquinoline-3-carboxylic acid (240 mg, 0.77 mmol) in DCM (5 mL) was added 1-chloro-N,N,2-trimethylprop-1-en-1-amine (0.10 mL, 0.77 mmol). The reaction mixture was stirred at rt for 15 min and treated with a solution of (R)-methyl 4-(((1-(2-fluorophenyl)ethyl)amino)methyl)benzoate (200 mg, 0.70 mmol) in DCM (1.5 ml) and DIEA (0.24 mL, 1.39 mmol). The reaction mixture was stirred at rt for 30 min. The reaction mixture was concentrated in vacuo and the residue was purified by flash column chromatography (eluting with 50% EtOAc/hexane) to afford the title compound as a white solid (0.37 g, 92%). $^1$H NMR (CDCl$_3$) δ 7.77-7.64 (m, 2H), 7.46-7.29 (m, 5H), 7.25-7.04 (m, 7H), 6.91-6.73 (m, 3H), 5.74-5.44 (m, 1H), 5.25 (s, 2H), 5.19-4.84 (m, 2H), 4.73-4.46 (m, 2H), 4.30 (d, J=15.8 Hz, 0.5H), 4.18-4.07 (m, 0.5H), 3.99-3.82 (m, 3H), 3.39-3.10 (m, 2H), 1.69 (d, J=7.0 Hz, 2H), 1.16 (d, J=6.8 Hz, 1H); MS(ESI$^+$) m/z 581.4 (M+H)$^+$.

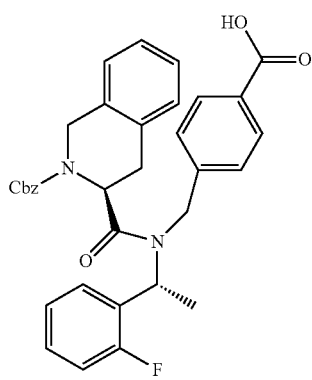 [SMILES: C[C@H](c1ccccc1F)N(Cc1ccc(C(=O)O)cc1)C(=O)[C@@H]1Cc2ccccc2CN1C(=O)OCc1ccccc1]

E) 4-(((S)-2-((Benzyloxy)carbonyl)-N-((R)-1-(2-fluorophenyl)ethyl)-1,2,3,4-tetrahydroisoquinoline-3-carboxamido)methyl)benzoic acid To a solution of (S)-benzyl 3-(((R)-1-(2-fluorophenyl)ethyl)(4-(methoxycarbonyl)benzyl)carbamoyl)-3,4-dihydroisoquinoline-2(1H)-carboxylate (0.37 g, 0.64 mmol) in THF (3 mL) and MeOH (2 mL) was added LiOH solution (3.19 mL, 6.37 mmol). The resulting mixture was stirred at rt overnight. The reaction mixture was acidified with 1 N HCl solution and the resulting mixture was extracted with ethyl acetate. The organic layer was separated, washed with brine and dried over MgSO$_4$. The filtrate was concentrated in vacuo to give the title compound as a white solid (345 mg, 95%). $^1$H NMR (DMSO-d$_6$) δ 7.55 (d, J=7.9 Hz, 2H), 7.48-7.10 (m, 12H), 6.98-6.66 (m, 3H), 5.74-5.30 (m, 2H), 5.25-5.06 (m, 2H), 4.86-4.39 (m, 3.5H), 4.11 (d, J=16.1 Hz, 0.5H), 3.86-3.72 (m, 0.5H), 3.28-3.17 (m, 1.5H), 1.64 (d, J=6.4 Hz, 1H), 1.37 (br. s., 1H), 1.27 (d, J=6.6 Hz, 1H); MS(ESI$^+$) m/z 567.4 (M+H)$^+$.

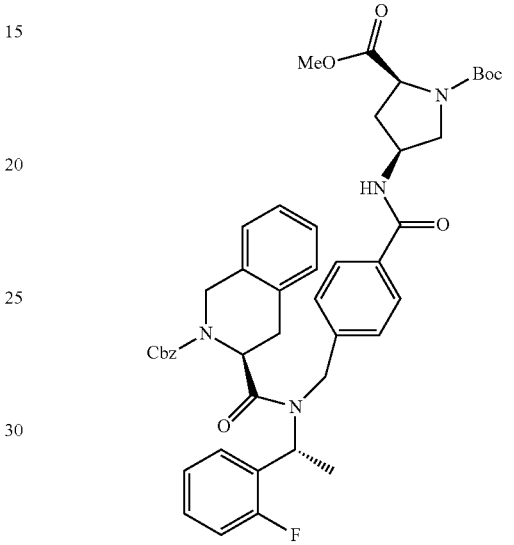

F) (2S,4S)-1-tert-Butyl 2-methyl 4-(4-(((S)-2-((benzyloxy)carbonyl)-N-((R)-1-(2-fluorophenyl)ethyl)-1,2,3,4-tetrahydroisoquinoline-3-carboxamido)methyl)benzamido)pyrrolidine-1,2-dicarboxylate To a solution of 4-(((S)-2-((benzyloxy)carbonyl)-N-((R)-1-(2-fluorophenyl)ethyl)-1,2,3,4-tetrahydroisoquinoline-3-carboxamido)methyl)benzoic acid (340 mg, 0.60 mmol) in DMF (4 mL) was added HATU (365 mg, 0.96 mmol), followed by a solution of (2S,4S)-1-tert-butyl 2-methyl 4-aminopyrrolidine-1,2-dicarboxylate, HCl (202 mg, 0.72 mmol) in DMF (1.5 mL) and DIEA (0.4 mL, 2.40 mmol). The reaction mixture was stirred at rt for 2 h and extracted with ethyl acetate. The organic layer was separated, washed with saturated aq. NHCO$_3$ solution and dried over MgSO$_4$. The filtrate was concentrated in vacuo and the residue was purified by flash column chromatography (eluting with 35% EtOAc/DCM) to afford the title compound as a white solid (0.42 g, 89%). $^1$H NMR (CD$_3$OD) δ 8.23 (br. s., 1H), 7.77-6.62 (m, 16H), 5.83-5.33 (m, 2H), 5.30-5.03 (m, 2H), 4.79-4.43 (m, 3H), 4.39-3.92 (m, 2H), 3.86-3.65 (m, 4.5H), 3.55-3.33 (m, 2.5H), 3.14-2.91 (m, 1H), 2.73-2.52 (m, 1H), 2.16-2.03 (m, 1H), 1.74 (d, J=6.6 Hz, 1H), 1.54-1.36 (m, 9H), 1.33-1.23 (m, 2H); MS(ESI$^+$) m/z 793.5 (M+H)$^+$.

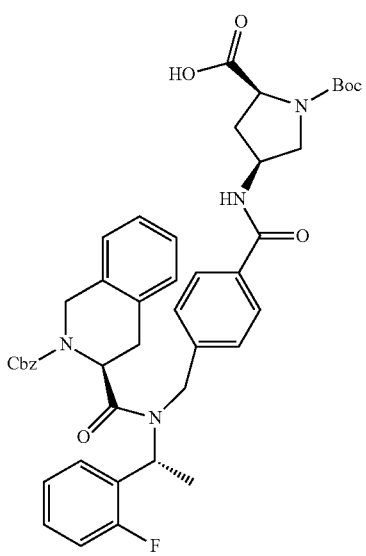 [SMILES: C[C@H](c1ccccc1F)N(Cc1ccc(C(=O)N[C@H]2C[C@@H](C(=O)O)N(C(=O)OC(C)(C)C)C2)cc1)C(=O)[C@@H]1Cc2ccccc2CN1C(=O)OCc1ccccc1]

G) (2S,4S)-4-(4-(((S)-2-((Benzyloxy)carbonyl)-N-((R)-1-(2-fluorophenyl)ethyl)-1,2,3,4-tetrahydroisoquinoline-3-carboxamido)methyl)benzamido)-1-(tert-butoxycarbonyl)pyrrolidine-2-carboxylic acid To a solution of (2S,4S)-1-tert-butyl 2-methyl 4-(4-(((S)-2-((benzyloxy)carbonyl)-N-((R)-1-(2-fluorophenyl)ethyl)-1,2,3,4-tetrahydroisoquinoline-3-carboxamido)methyl)benzamido)pyrrolidine-1,2-dicarboxylate (420 mg, 0.53 mmol) in THF (4 mL) and MeOH (2 mL) was added aq. LiOH solution (5.3 mL, 5.30 mmol). The suspension was stirred at rt for 2.5 h. To the reaction mixture was added 1 N HCl solution until the pH of the solution was 1. The resulting mixture was extracted with ethyl acetate. The organic layer was separated, washed with brine and dried over MgSO$_4$. The filtrate was concentrated in vacuo to give the title compound as a white solid (418 mg, 100%). $^1$H NMR (DMSO-d$_6$) δ 8.30-8.16 (m, 1H), 7.58-6.85 (m, 15H), 6.81-6.64 (m, 1H), 5.75 (s, 1H), 5.62-5.29 (m, 1H), 5.21 (s, 1H), 5.18-5.08 (m, 1H), 4.91-4.27 (m, 4H), 4.23-4.06 (m, 1H), 3.85-3.61 (m, 1H), 3.26-3.13 (m, 2H), 2.89-2.63 (m, 2H), 2.04-1.84 (m, 3H), 1.62 (d, J=6.4 Hz, 1H), 1.47-1.30 (m, 9H), 1.24 (d, J=6.6 Hz, 1H); MS(ESI$^+$) m/z 779.5 (M+H)$^+$.

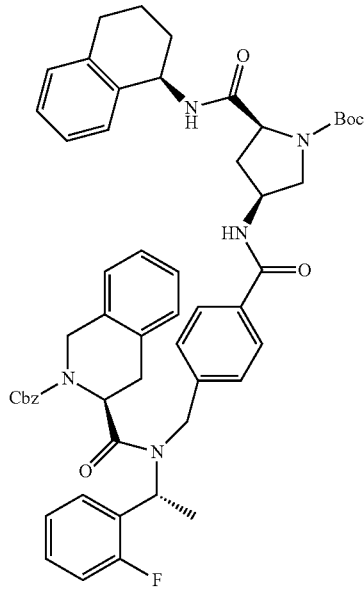 [SMILES: C[C@H](c1ccccc1F)N(Cc1ccc(C(=O)N[C@H]2C[C@@H](C(=O)N[C@@H]3CCCc4ccccc43)N(C(=O)OC(C)(C)C)C2)cc1)C(=O)[C@@H]1Cc2ccccc2CN1C(=O)OCc1ccccc1]

H) (S)-Benzyl 3-((4-(((3S,5S)-1-(tert-butoxycarbonyl)-5-(((R)-1,2,3,4-tetrahydronaphthalen-1-yl)carbamoyl)pyrrolidin-3-yl)carbamoyl)benzyl)((R)-1-(2-fluorophenyl)ethyl)carbamoyl)-3,4-dihydroisoquinoline-2(1H)-carboxylate To a solution of (2S,4S)-4-(4-(((S)-2-((benzyloxy)carbonyl)-N-((R)-1-(2-fluorophenyl)ethyl)-1,2,3,4-tetrahydroisoquinoline-3-carboxamido)methyl)benzamido)-1-(tert-butoxycarbonyl)pyrrolidine-2-carboxylic acid (415 mg, 0.53 mmol) in DMF (4 mL) was added HATU (304 mg, 0.80 mmol). The reaction mixture was stirred at rt for 5 min and treated with (R)-1,2,3,4-tetrahydronaphthalen-1-amine (86 mg, 0.59 mmol, source: ALFA AESAR®) dropwise followed by DIEA (0.19 mL, 1.07 mmol). The resulting mixture was stirred at rt for 2 h and diluted with ethyl acetate and brine. The organic layer was separated, washed with saturated aq. NaHCO$_3$ solution and dried over MgSO$_4$. The filtrate was concentrated in vacuo and the residue was purified by flash column chromatography (eluting with 40% EtOAc/DCM) to afford the title compound as a white solid (0.43 g, 89%). $^1$H NMR (CDCl$_3$) δ 9.08-8.67 (m, 1H), 8.01-7.57 (m, 3H), 7.47-7.27 (m, 5H), 7.25-6.73 (m, 13H), 5.72-5.42 (m, 1H), 5.27-4.82 (m, 4H), 4.77-4.11 (m, 5H), 3.71-3.49 (m, 2H), 3.36-2.99 (m, 1H), 2.89-2.66 (m, 2H), 2.54 (d, J=13.4 Hz, 1H), 2.27 (d, J=7.3 Hz, 1H), 2.19-2.03 (m, 1H), 1.98-1.69 (m, 4H), 1.65 (d, J=6.6 Hz, 2H), 1.51-1.22 (m, 10H), 1.10 (d, J=6.8 Hz, 1H); MS(ESI$^+$) m/z 908.6 (M+H)$^+$.

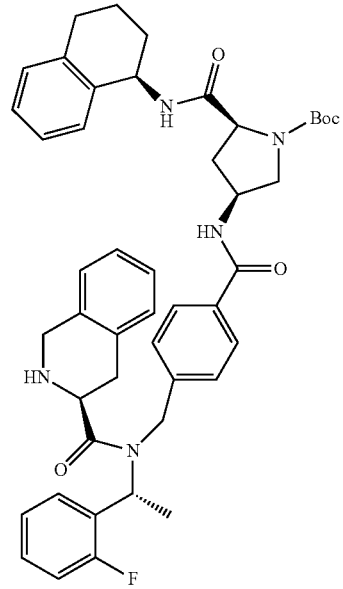 [SMILES: C[C@H](c1ccccc1F)N(Cc1ccc(C(=O)N[C@H]2C[C@@H](C(=O)N[C@@H]3CCCc4ccccc43)N(C(=O)OC(C)(C)C)C2)cc1)C(=O)[C@@H]1Cc2ccccc2CN1]

I) (2S,4S)-tert-Butyl 4-(4-(((S)-N-((R)-1-(2-fluorophenyl)ethyl)-1,2,3,4-tetrahydroisoquinoline-3-carboxamido)methyl)benzamido)-2-(((R)-1,2,3,4-tetrahydronaphthalen-1-yl)carbamoyl)pyrrolidine-1-carboxylate To a solution of (S)-benzyl 3-((4-(((3S,5S)-1-(tert-butoxycarbonyl)-5-(((R)-1,2,3,4-tetrahydronaphthalen-1-yl)carbamoyl)pyrrolidin-3-yl)carbamoyl)benzyl)((R)-1-(2-fluorophenyl)ethyl)carbamoyl)-3,4-dihydroisoquinoline-2(1H)-carboxylate (420 mg, 0.46 mmol) in MeOH (7 mL)

was added Pd—C (155 mg, 0.15 mmol). The reaction mixture was degassed under vacuum and back filled with H₂. The process was repeated twice and the reaction mixture was sealed under a blanket of hydrogen (balloon) for 3 h. The reaction mixture was filtered through a pad of CELITE® (rinsed with MeOH). The filtrate was concentrated in vacuo to give the title compound as a white solid (340 mg, 95%). ¹H NMR (CDCl₃) δ 9.07-8.72 (m, 1H), 7.96-7.55 (m, 3H), 7.30 (d, J=7.3 Hz, 2H), 7.23-6.67 (m, 10H), 5.36 (d, J=7.3 Hz, 1H), 5.16 (br. s., 1H), 4.91-4.39 (m, 5H), 4.34-4.12 (m, 1H), 3.71-3.48 (m, 2H), 3.44-3.27 (m, 1H), 2.93-2.70 (m, 2H), 2.64 (s, 1H), 2.52 (d, J=13.0 Hz, 1H), 2.27 (dd, J=13.8, 6.5 Hz, 1H), 2.20-2.02 (m, 2H), 1.94-1.72 (m, 3H), 1.69-1.48 (m, 3H), 1.43-1.17 (m, 9H); MS(ESI⁺) m/z 774.6 (M+H)⁺.

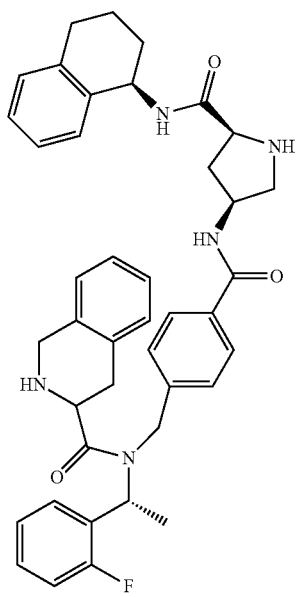 [SMILES: C[C@H](c1ccccc1F)N(Cc1ccc(C(=O)N[C@@H]2CN[C@H](C(=O)N[C@@H]3CCCc4ccccc43)C2)cc1)C(=O)C1Cc2ccccc2CN1]

J) (S)-N-((R)-1-(2-Fluorophenyl)ethyl)-N-(4-(((3S,5S)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide To a solution of (2S,4S)-tert-butyl 4-(4-(((S)-N-((R)-1-(2-fluorophenyl)ethyl)-1,2,3,4-tetrahydroisoquinoline-3-carboxamido)methyl)benzamido)-2-(((R)-1,2,3,4-tetrahydronaphthalen-1-yl)carbamoyl)pyrrolidine-1-carboxylate (330 mg, 0.43 mmol) in DCM (3 mL) was added HCl (4.0M solution in dioxane, 2.3 mL, 9.04 mmol). The reaction mixture was stirred at rt for 2 h and concentrated in vacuo to give the title compound as a white solid (2 HCl salt, 300 mg, 94%). ¹H NMR (CD₃OD) δ 7.73-7.49 (m, 3H), 7.38-7.04 (m, 11H), 6.97 (d, J=8.1 Hz, 1H), 6.86-6.76 (m, 1H), 5.96-5.52 (m, 1H), 5.10 (d, J=5.3 Hz, 1H), 5.04-4.85 (m, 2H), 4.71-4.46 (m, 3H), 4.44-4.23 (m, 3H), 3.73-3.58 (m, 2H), 3.54-3.46 (m, 1H), 2.87-2.59 (m, 3H), 2.27-2.16 (m, 1H), 1.95-1.74 (m, 3H), 1.74-1.58 (m, 3H), 1.25 (s, 1H); MS(ESI⁺) m/z 674.5 (M+H)⁺.

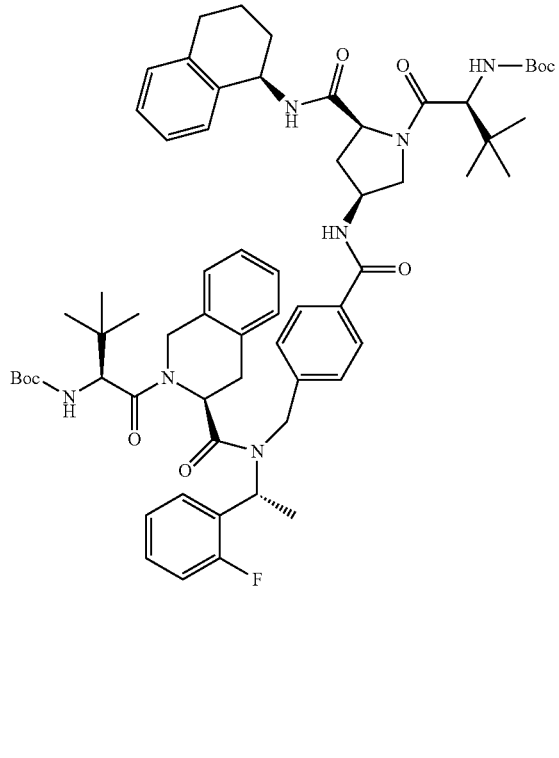 [SMILES: C[C@H](c1ccccc1F)N(Cc1ccc(C(=O)N[C@H]2C[C@@H](C(=O)N[C@@H]3CCCc4ccccc43)N(C(=O)[C@@H](NC(=O)OC(C)(C)C)C(C)(C)C)C2)cc1)C(=O)[C@@H]1Cc2ccccc2CN1C(=O)[C@@H](NC(=O)OC(C)(C)C)C(C)(C)C]

K) Intermediate I

To a solution of (S)-2-((tert-butoxycarbonyl)amino)-3,3-dimethylbutanoic acid (297 mg, 1.29 mmol) in DMF (2 mL) was added HATU (358 mg, 0.94 mmol). The reaction mixture was stirred at rt for 10 min and treated with a solution of (S)-N-((R)-1-(2-fluorophenyl)ethyl)-N-(4-(((3S,5S)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, 2 HCl (300 mg, 0.40 mmol) in DMF (3 mL) and DIEA (0.30 mL, 1.71 mmol). The resulting mixture was stirred at rt overnight and diluted with ethyl acetate and brine. The organic layer was separated, washed with saturated aq. NaHCO₃ solution and dried over MgSO₄. The filtrate was concentrated in vacuo and the residue was purified by flash column chromatography (eluting with 8% MeOH/DCM) to afford the title compound as a white solid (290 mg, 66%). ¹H NMR (CDCl₃) δ 9.26-8.98 (m, 1H), 7.99 (d, J=8.1 Hz, 0.5H), 7.81 (d, J=8.1 Hz, 1H), 7.73 (d, J=8.1 Hz, 1.5H), 7.45 (d, J=8.1 Hz, 0.5H), 7.40-7.29 (m, 1.5H), 7.26-7.12 (m, 6H), 7.11-6.94 (m, 4H), 6.92-6.80 (m, 1H), 6.02-5.68 (m, 1H), 5.55-5.30 (m, 1.5H), 5.27-4.91 (m, 4.5H), 4.88-4.53 (m, 5H), 4.44 (d, J=16.3 Hz, 0.5H), 4.22-3.80 (m, 3H), 3.17-2.93 (m, 0.5H), 2.90-2.68 (m, 4H), 2.61-2.45 (m, 1H), 2.40-2.23 (m, 1H), 2.11-1.96 (m, 1H), 1.76-1.53 (m, 3H), 1.40 (m, 18H), 1.16-0.90 (m, 9H), 0.82-0.68 (m, 9H); MS(ESI⁺) m/z 1100.8 (M+H)⁺.

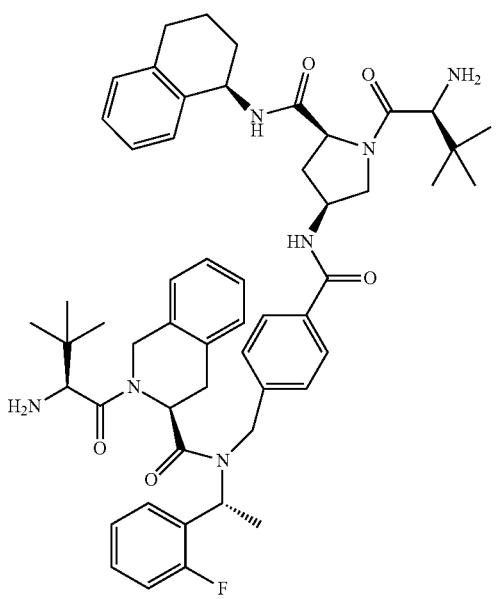 [SMILES: C[C@H](c1ccccc1F)N(Cc1ccc(C(=O)N[C@H]2C[C@@H](C(=O)N[C@@H]3CCCc4ccccc43)N(C(=O)[C@@H](N)C(C)(C)C)C2)cc1)C(=O)[C@@H]1Cc2ccccc2CN1C(=O)[C@@H](N)C(C)(C)C]

L) (S)-2-((S)-2-Amino-3,3-dimethylbutanoyl)-N-(4-(((3S,5S)-1-((R)-2-amino-3,3-dimethylbutanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)ethyl)-1,2,3,4-tetrahydroisoquinoline-3-carboxamide To a solution of the above Intermediate I (290 mg, 0.26 mmol) in DCM (5 mL) was added TFA (1.3 mL, 16.87 mmol). The reaction mixture was stirred at rt for 1 h and concentrated in vacuo to give the title compound as a white solid (2 TFA salt, 285 mg, 96%). $^1$H NMR (CD$_3$OD) δ 9.27-9.04 (m, 1H), 8.77-8.59 (m, 1H), 7.86 (d, J=8.1 Hz, 0.5H), 7.67 (d, J=8.4 Hz, 1.5H), 7.59-7.47 (m, 1H), 7.21-7.21 (m, 1H), 7.45-7.20 (m, 5H), 7.19-6.83 (m, 7H), 5.98-5.81 (m, 1H), 5.22-4.87 (m, 3H), 4.76-4.42 (m, 5H), 4.13-3.71 (m, 3H), 3.16-2.88 (m, 2H), 2.86-2.55 (m, 3H), 2.18-1.75 (m, 5H), 1.73-1.57 (m, 3H), 1.35-1.26 (m, 1H), 1.23-1.05 (m, 18H); MS(ESI$^+$) m/z 901.8 (M+H)$^+$.

was added EDC (167 mg, 0.87 mmol), 3H-[1,2,3]-triazolo[4,5-b]pyridin-3-ol (74 mg, 0.55 mmol) and a solution of (S)-2-((S)-2-amino-3,3-dimethylbutanoyl)-N-(4-(((3S,5S)-1-((S)-2-amino-3,3-dimethylbutanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)ethyl)-1,2,3,4-tetrahydroisoquinoline-3-carboxamide, 2 TFA (280 mg, 0.25 mmol) in DMF (4 mL) followed by DIEA (0.43 mL, 2.48 mmol). The resulting mixture was stirred at rt for 1.5 h and diluted with ethyl acetate and brine. The organic layer was separated, washed successively with saturated aq. NaHCO$_3$ solution, 1N HCl solution and brine. The organic layer was separated and dried over MgSO$_4$. The filtrate was concentrated in vacuo and the residue was purified by preparative HPLC. Fractions containing the product were combined, concentrated, and lyophilized to give the title compound as a white solid (250 mg, 79%). $^1$H NMR (CDCl$_3$) δ 9.17-8.83 (m, 1H), 7.99 (d, J=8.4 Hz, 0.5H), 7.91 (d, J=8.6 Hz, 0.5H), 7.72 (d, J=8.4 Hz, 1H), 7.49-6.69 (m, 14H), 6.03-5.72 (m, 1H), 5.29-4.89 (m, 4H), 4.86-4.28 (m, 8H), 4.14-3.79 (m, 2H), 3.17-2.87 (m, 2H), 2.84-2.70 (m, 8H), 2.54 (d, J=13.9 Hz, 2H), 2.37-2.21 (m, 1H), 2.11-1.80 (m, 4H), 1.75-1.54 (m, 3H), 1.50-1.45 (m, 17H), 1.36-1.21 (m, 6H), 1.12-0.86 (m, 9H), 0.78-0.64 (m, 9H); MS(ESI$^+$) m/z 1270.8 (M+H)$^+$.

N) c(S)-N-(4-(((3S,5S)-1-((S)-3,3-Dimethyl-2-((R)-2-(methylamino)propanamido)butanoyl)-5-(((R)-1,2,3,4-tetrahydronaphthalen-1-yl)carbamoyl)pyrrolidin-3-yl)carbamoyl)benzyl)-2-((S)-3,3-dimethyl-2-((S)-2-(methylamino)propanamido)butanoyl)-N-((R)-1-(2-fluorophenyl)ethyl)-1,2,3,4-tetrahydroisoquinoline-3-carboxamide To a solution of the above Intermediate II (220 mg, 0.17 mmol) in DCM (4 mL) were added TFA (1.4 mL, 18.17 mmol). The reaction mixture was stirred at rt for 1 h and concentrated in vacuo. The residue was purified by preparative HPLC. Fractions containing the product were combined, concentrated, and lyophilized to give the title compound as a white solid (2 TFA salt, 185 mg, 81%). $^1$H NMR (CD$_3$OD) δ 8.57 (d, J=8.6 Hz, 0.5H), 7.96-7.80 (m, 0.5H), 7.73-7.59 (m, 1.5H), 7.56-7.46 (m, 1H), 7.42 (d, J=7.7 Hz, 1H), 7.39-6.84 (m, 11.5H), 5.98-5.80 (m, 1H), 5.26-4.97 (m, 4H), 4.78-4.49 (m, 6H), 4.22-3.76 (m, 4H), 3.16-3.04 (m, 1H), 2.97-2.71 (m, 3H), 2.70-2.46 (m, 7H), 2.17-1.74 (m, 5H), 1.70 (d, J=6.8 Hz, 2H), 1.62-1.51 (m, 1H), 1.47 (d, J=6.8 Hz, 3H), 1.41-1.26 (m, 3H), 1.19-0.97 (m, 18H); MS(ESI$^+$) m/z 1070.8 (M+H)$^+$.

Example 2

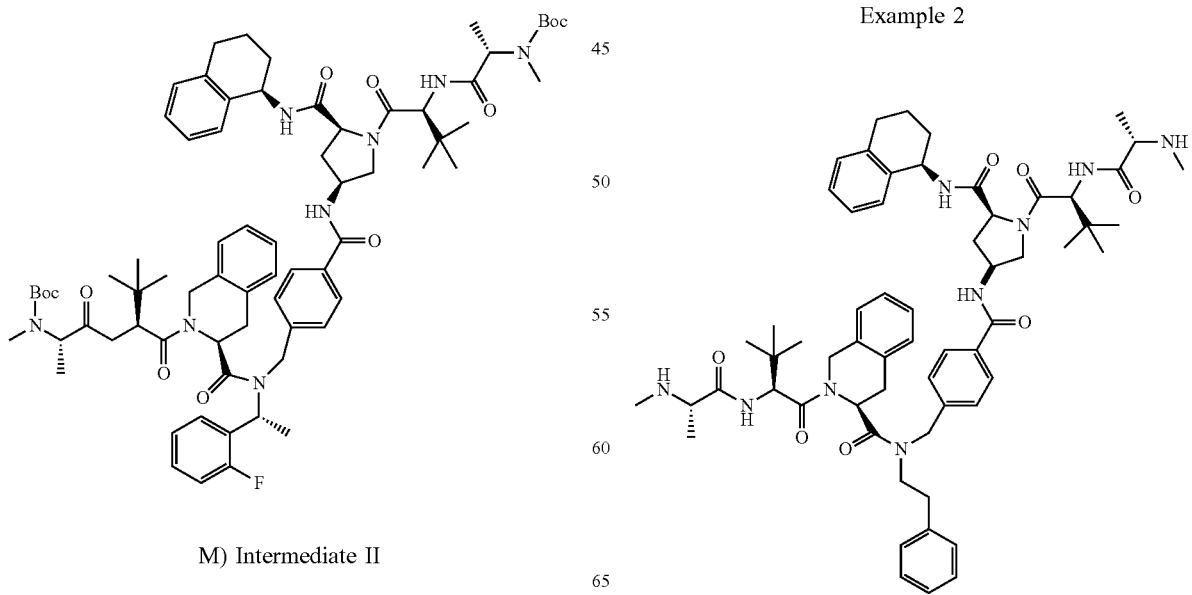

M) Intermediate II

To a solution of (S)-2-((tert-butoxycarbonyl)(methyl)amino)propanoic acid (151 mg, 0.75 mmol) in DMF (2 mL)

(S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-phenethyl-1,2,3,4-tetrahydroisoquinoline-3-carboxamide

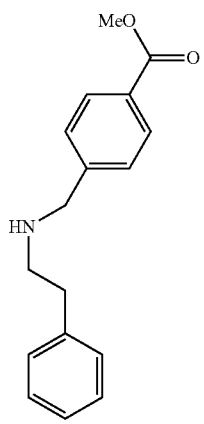 [SMILES: COC(=O)c1ccc(CNCCc2ccccc2)cc1]

A) Methyl 4-((phenethylamino)methyl)benzoate

To a solution of 2-(cyclohexa-1,5-dien-1-yl)ethanamine (565 mg, 4.58 mmol) in DMF (12 mL) was added methyl 4-(bromomethyl)benzoate (750 mg, 3.27 mmol) and K$_2$CO$_3$ (905 mg, 6.55 mmol). The suspension was stirred at rt for 2 h and diluted with ethyl acetate and brine. The organic layer was separated, washed with brine and dried over MgSO$_4$. The filtrate was concentrated in vacuo and the residue was purified by flash column chromatography (eluting with 60% EtOAc/hexane) to afford the title compound as a white solid (0.55 g, 62%). $^1$H NMR (CDCl$_3$) δ 7.99 (d, J=8.4 Hz, 2H), 7.36 (d, J=8.4 Hz, 2H), 7.33-7.28 (m, 2H), 7.25-7.18 (m, 3H), 3.92 (s, 3H), 3.87 (s, 2H), 2.95-2.80 (m, 4H); MS(ESI$^+$) m/z 270.3 (M+H)$^+$.

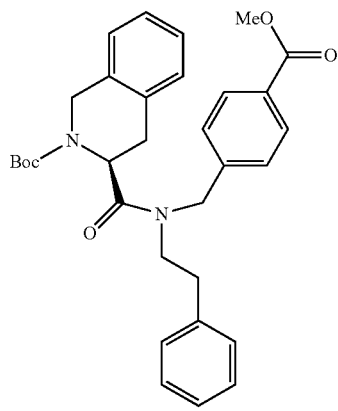 [SMILES: COC(=O)c1ccc(CN(CCc2ccccc2)C(=O)[C@@H]2Cc3ccccc3CN2C(=O)OC(C)(C)C)cc1]

B) (S)-tert-Butyl 3-((4-(methoxycarbonyl)benzyl)(phenethyl)carbamoyl)-3,4-dihydroisoquinoline-2(1H)-carboxylate To a solution of (S)-2-(tert-butoxycarbonyl)-1,2,3,4-tetrahydroisoquinoline-3-carboxylic acid (111 mg, 0.40 mmol) in DMF (3 mL) were sequentially added EDC (96 mg, 0.50 mmol), 3H-[1,2,3]-triazolo[4,5-b]pyridin-3-ol (46 mg, 0.33 mmol), a solution of methyl 4-((phenethylamino)methyl)benzoate (90 mg, 0.33 mmol) in DMF (2 mL) and 4-methylmorpholine (0.09 mL, 0.84 mmol). The reaction mixture was stirred at rt for 1 h and diluted with ethyl acetate and brine. The organic layer was separated, washed successively with saturated aq. NaHCO$_3$ solution, brine, 1 N HCl solution. The organic layer was dried over MgSO$_4$ and the filtrate was concentrated in vacuo. The residue was purified by flash column chromatography (eluting with 30% EtOAc/hexane) to afford the title compound as a white solid (0.15 g, 85%). $^1$H NMR (CDCl$_3$) δ 8.12-7.88 (m, 2H), 7.37-7.29 (m, 3H), 7.24-7.05 (m, 8H), 5.25-4.92 (m, 1H), 4.83-4.43 (m, 3H), 3.94 (s, 2H), 3.91 (s, 3H), 3.58-3.41 (m, 1H), 3.01-2.74 (m, 4H), 1.53-1.41 (m, 9H); MS(ESI$^+$) m/z 529.4 (M+H)$^+$.

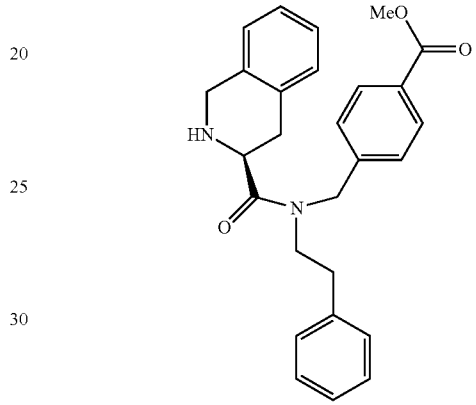

C) (S)-Methyl 4-((N-phenethyl-1,2,3,4-tetrahydroisoquinoline-3-carboxamido)methyl)benzoate To a solution of (S)-tert-butyl 3-((4-(methoxycarbonyl)benzyl)(phenethyl)carbamoyl)-3,4-dihydroisoquinoline-2(1H)-carboxylate (150 mg, 0.28 mmol) in DCM (2 mL) was added TFA (0.8 mL, 0.28 mmol). The reaction mixture was stirred at rt for 1.5 h and concentrated in vacuo to give the title compound as a white solid (TFA salt, 154 mg, 100%). $^1$H NMR (DMSO-d$_6$) δ 8.06-7.81 (m, 2H), 7.58-7.41 (m, 2H), 7.37-7.13 (m, 9H), 4.97-4.56 (m, 3H), 4.36 (d, J=10.1 Hz, 2H), 3.86 (s, 3H), 3.82-3.52 (m, 2H), 3.23-2.73 (m, 4H); MS(ESI$^+$) m/z 429.4 (M+H)$^+$.

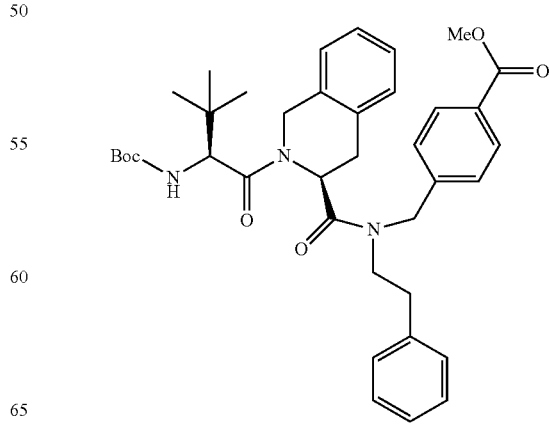

D) Methyl 4-(((S)-2-((S)-2-((tert-butoxycarbonyl)amino)-3,3-dimethylbutanoyl)-N-phenethyl-1,2,3,4-tetrahydroisoquinoline-3-carboxamido)methyl)benzoate To a solution of N-(tert-butoxycarbonyl)-L-tert-leucine (107 mg, 0.46 mmol) in DMF (2 mL) were added EDC (114 mg, 0.60 mmol), 3H-[1,2,3]-triazolo[4,5-b]pyridin-3-ol (45 mg, 0.33 mmol), a solution of (S)-methyl 4-((N-phenethyl-1,2,3,4-tetrahydroisoquinoline-3-carboxamido)methyl)benzoate, FA (180 mg, 0.33 mmol) in DMF (2 mL) and 4-methylmorpholine (0.22 mL, 1.99 mmol). The resulting reaction mixture was stirred at rt for 3 h and diluted with ethyl acetate and brine. The organic layer was separated, washed successively with saturated aq. NaHCO$_3$ solution, brine, and 1 N HCl solution. The organic layer was dried over MgSO$_4$ and the filtrated was concentrated in vacuo. The residue was purified by flash column chromatography (eluting with 30% EtOAc/hexane) to afford the title compound as a white solid (0.20 g, 94%). MS(ESI$^+$) m/z 642.6 (M+H)$^+$.

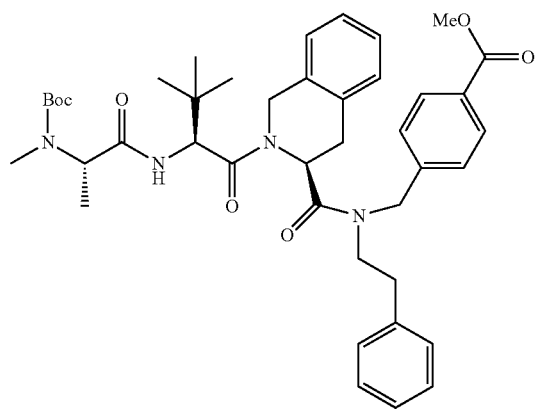

F) Methyl 4-(((S)-2-((S)-2-((S)-2-((tert-butoxycarbonyl)(methyl)amino)propanamido)-3,3-dimethylbutanoyl)-N-phenethyl-1,2,3,4-tetrahydroisoquinoline-3-carboxamido)methyl)benzoate To a solution of (S)-2-((tert-butoxycarbonyl)(methyl)amino)propanoic acid (88 mg, 0.44 mmol) in DMF (2 mL) were added EDC (89 mg, 0.46 mmol), 3H-[1,2,3]-triazolo[4,5-b]pyridin-3-ol (39 mg, 0.29 mmol), a solution of methyl 4-(((S)-2-((S)-2-amino-3,3-dimethylbutanoyl)-N-phenethyl-1,2,3,4-tetrahydroisoquinoline-3-carboxamido)methyl)benzoate, TFA (190 mg, 0.29 mmol) in DMF (2 mL) and 4-methylmorpholine (0.19 mL, 1.74 mmol). The reaction mixture was stirred at rt for 1 h and diluted with ethyl acetate and brine. The organic layer was separated, washed successively with saturated aq. NaHCO$_3$ solution, and brine, and dried over MgSO$_4$. The filtrate was concentrated in vacuo and the residue was purified by flash column chromatography (eluting with 30% EtOAc/hexane) to afford the title compound as a white solid (0.15 g, 71%). $^1$H NMR (CDCl$_3$) δ 8.05 (d, J=8.0 Hz, 0.5H), 7.95 (d, J=8.3 Hz, 1.5H), 7.44-6.85 (m, 11H), 5.15-4.98 (m, 2H), 4.89 (d, J=15.5 Hz, 2H), 4.74-4.61 (m, 2H), 4.50-4.27 (m, 1H), 3.95 (s, 1H), 3.91 (s, 2H), 3.07-2.90 (m, 3H), 2.81 (s, 3H), 2.67-2.55 (m, 1H), 2.05 (s, 2H), 1.55-1.43 (m, 9H), 1.34-1.21 (m, 3H), 1.13-0.89 (m, 9H); MS(ESI$^+$) m/z 727.6 (M+H)$^+$.

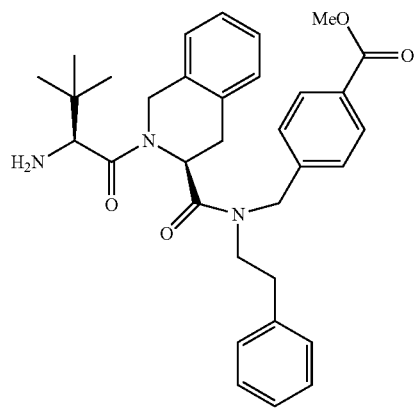 [SMILES: COC(=O)c1ccc(CN(CCc2ccccc2)C(=O)[C@@H]2Cc3ccccc3CN2C(=O)[C@@H](N)C(C)(C)C)cc1]

E) Methyl 4-(((S)-2-((S)-2-amino-3,3-dimethylbutanoyl)-N-phenethyl-1,2,3,4-tetrahydroisoquinoline-3-carboxamido)methyl)benzoate To a solution of methyl 4-(((S)-2-((S)-2-((tert-butoxycarbonyl)amino)-3,3-dimethylbutanoyl)-N-phenethyl-1,2,3,4-tetrahydroisoquinoline-3-carboxamido)methyl)benzoate (200 mg, 0.31 mmol) in DCM (3 mL) was added TFA (1.0 mL, 13 mmol). The reaction mixture was stirred at rt for 4 h and concentrated in vacuo to give the title compound as a colorless oily solid (TFA salt, 190 mg, 93%). $^1$H NMR (DMSO-d$_6$) δ 8.09-7.91 (m, 3H), 7.88 (d, J=8.4 Hz, 1H), 7.60-6.99 (m, 9H), 5.21-5.07 (m, 1H), 4.91-4.70 (m, 1H), 4.57-4.38 (m, 1H), 4.17 (d, J=1.3 Hz, 1H), 3.89-3.76 (m, 1H), 3.66-3.43 (m, 1H), 3.12-3.02 (m, 1H), 2.90-2.78 (m, 1H), 1.13 (s, 1H), 1.08 (s, 4H), 0.99 (d, J=1.8 Hz, 2H), 0.96 (s, 9H); MS(ESI$^+$) m/z 542.5 (M+H)$^+$.

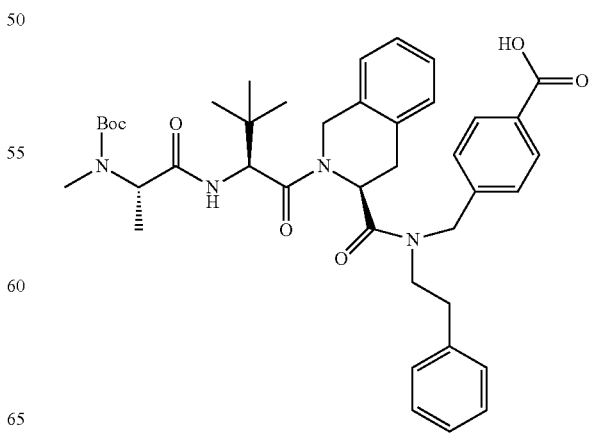

G) 4-(((S)-2-((S)-2-((S)-2-((tert-Butoxycarbonyl)(methyl)amino)propanamido)-3,3-dimethylbutanoyl)-N-phenethyl-1,2,3,4-tetrahydroisoquinoline-3-carboxamido)methyl)benzoic acid To a solution of methyl 4-(((S)-2-((S)-2-((S)-2-((tert-butoxycarbonyl)(methyl)amino)propanamido)-3,3-dimethylbutanoyl)-N-phenethyl-1,2,3,4-tetrahydroisoquinoline-3-carboxamido)methyl)benzoate (150 mg, 0.21 mmol) in THF (1 mL) and MeOH (1 mL) was added a solution of NaOH (50 mg, 1.24 mmol) in water (1 mL). The resulting reaction mixture was stirred at rt for 4.5 h. To the mixture was added 1 N HCl solution until the pH was 2. The resulting mixture was extracted with ethyl acetate. The organic layer was separated and dried over MgSO$_4$. The filtrate was concentrated in vacuo to give the title compound as a white solid (135 mg, 92%). $^1$H NMR (DMSO-d$_6$) δ 7.99-7.75 (m, 2H), 7.54-6.99 (m, 11H), 5.11-4.67 (m, 4H), 4.60-4.34 (m, 3H), 3.94-3.42 (m, 1H), 3.09-2.88 (m, 1H), 2.85-2.61 (m, 5H), 1.99 (s, 1H), 1.91 (s, 2H), 1.38 (br. s., 9H), 1.21-1.09 (m, 2H), 1.05-0.87 (m, 9H); MS(ESI$^+$) m/z 713.6 (M+H)$^+$.

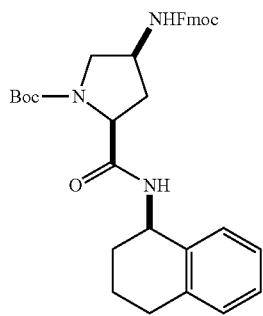

H) (2S,4S)-tert-Butyl 4-((((9H-fluoren-9-yl)methoxy)carbonyl)amino)-2-((R)-1,2,3,4-tetrahydronaphthalen-1-yl)carbamoyl)pyrrolidine-1-carboxylate To a solution of (2S,4S)-Boc-4-(Fmoc-amino)-proline (Chem-Impex, 6.00 g, 13.3 mmol) in DMF (20 mL) at 0° C. were added EDC (3.05 g, 15.9 mmol), HOAt (2.17 g, 15.9 mmol) and NMM (4.38 mL, 39.8 mmol). The reaction mixture was stirred at ice bath temperature for 20 min then treated with a solution of (R)-1,2,3,4-tetrahydronaphthalen-1-amine (ALFA AESAR®, 2.15 g, 14.6 mmol) in DMF (2 mL). The reaction mixture was stirred at rt for 1 h and cold water (100 mL) was added to the reaction mixture. The solid that formed was collected by filtration and washed with cold water (100 mL). The solid was dissolved in CH$_2$Cl$_2$ (200 mL) and the organic solution was washed with 5% aq. citric acid solution and brine, dried over MgSO$_4$, and filtered. The filtrate was concentrated in vacuo. The residue was dissolved in CH$_2$Cl$_2$ and purified by flash column chromatography (gradient elution from 10 to 30% EtOAc in CH$_2$Cl$_2$) provided the title compound (6.70 g, 87%) as a light tan solid. $^1$H NMR (400 MHz, CDCl$_3$) δ 7.79 (d, J=7.5 Hz, 2H), 7.67 (d, J=7.3 Hz, 2H), 7.42 (td, J=7.2, 4.0 Hz, 2H), 7.37-7.03 (m, 6H), 5.22 (br. s., 1H), 4.57-4.23 (m, 5H), 3.68-3.49 (m, 2H), 2.91-2.74 (m, 2H), 2.52 (d, J=13.4 Hz, 1H), 2.35-2.21 (m, 1H), 2.14 (d, J=5.1 Hz, 1H), 1.97-1.80 (m, 3H), 1.44 (s, 9H); MS(ESI$^+$) m/z 582.2 (M+H)$^+$.

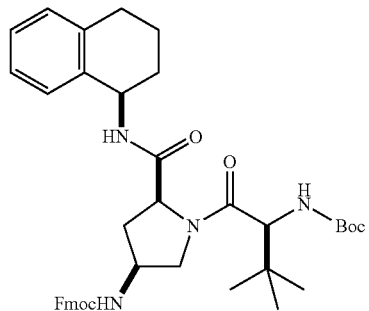

I) tert-Butyl ((S)-3,3-dimethyl-1-(2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate To a solution of (2S,4S)-tert-butyl 4-((((9H-fluoren-9-yl)methoxy)carbonyl)amino)-2-(((R)-1,2,3,4-tetrahydronaphthalen-1-yl)carbamoyl)pyrrolidine-1-carboxylate (6.70 g, 11.5 mmol) in CH$_2$Cl$_2$ (50 mL) at rt was added TFA (15 mL) dropwise. The reaction mixture was stirred at rt for 2 h, and then concentrated in vacuo. The residue was dissolved in CH$_2$Cl$_2$ (200 mL) and washed with aq. K$_2$HPO$_4$ solution (50 mL). The organic layer was dried over MgSO$_4$, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 100%), which was used directly in the next step.

To a solution of (S)-2-((tert-butoxycarbonyl)amino)-3,3-dimethylbutanoic acid (3.19 g, 13.8 mmol) in DMF (20 mL) at 0° C. were added EDC (3.31 g, 17.3 mmol), HOAt (2.35 g, 17.3 mmol) and NMM (3.80 mL, 34.5 mmol). The reaction mixture was stirred at ice bath temperature for 20 min, then treated with a suspension of (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 11.5 mmol) in DMF (5 mL). The reaction mixture was stirred at rt for 1 h and cold water (200 mL) was added to the reaction mixture. The solid that formed was collected by filtration and washed with of cold water (100 mL). The solid was dissolved in CH$_2$Cl$_2$ (200 mL). The organic solution was washed with aq. NaHCO$_3$ solution, 5% aq. citric acid solution and brine, dried over MgSO$_4$ and filtered. The filtrate was concentrated in vacuo. The residue was dissolved in CH$_2$Cl$_2$ and purified using flash column chromatography (gradient elution from 10 to 30% EtOAc in CH$_2$Cl$_2$) provided the title compound (7.10 g, 89%) as a light tan solid. MS(ESI$^+$) m/z 695.5 (M+H)$^+$.

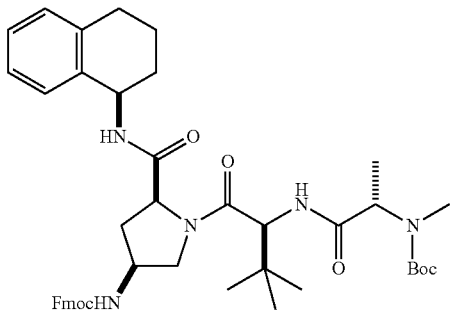

J) tert-Butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate (7.10 g, 10.2 mmol) in CH₂Cl₂ (50 mL) at rt was added TFA (15 mL) dropwise. The reaction mixture was stirred at rt for 2 h, and then concentrated in vacuo. The residue was dissolved in CH₂Cl₂ (200 mL) and washed with aq. K₂HPO₄ solution (50 mL). The organic layer was dried over MgSO₄, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (6.08 g, 100%), which was used directly in the next step.

To a solution of (S)-2-((tert-butoxycarbonyl)(methyl)amino)propanoic acid (Chem-Impex, 2.49 g, 12.3 mmol) in DMF (20 mL) at 0° C. were added EDC (2.94 g, 15.3 mmol), HOAt (2.09 g, 15.3 mmol) and NMM (2.81 mL, 25.6 mmol). The reaction mixture was stirred at ice bath temperature for 20 min, and then treated with a solution of (9H-fluoren-9-yl)methyl ((3S,5S)-5-(((R)-1,2,3,4-tetrahydronaphthalen-1-yl)carbamoyl)pyrrolidin-3-yl)carbamate (6.45 g, 10.2 mmol) in DMF (5 mL). The reaction mixture was stirred at rt for 2 h and then cold water (200 mL) was added to the reaction mixture. The solid that formed was collected by filtration and washed with cold water (100 mL). The solid was dissolved in CH₂Cl₂ (200 mL). The organic solution was washed with aq. NaHCO₃ solution, 5% aq. citric acid solution and brine, dried over MgSO₄, and filtered. The filtrate was concentrated in vacuo. The residue was dissolved in CH₂Cl₂ and purified by flash column chromatography (gradient elution from 10 to 40% EtOAc in CH₂Cl₂) provided the title compound (6.14 g, 77%) as a light tan solid. MS(ESI⁺) m/z 780.5 (M+H)⁺.

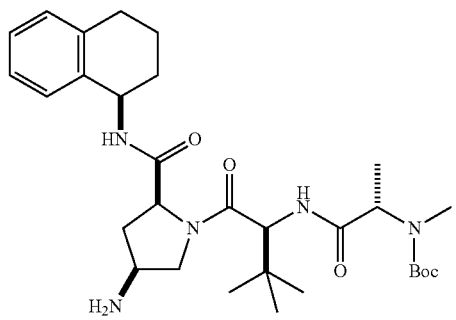

K) tert-Butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (6.14 g, 7.87 mmol) in CH₂Cl₂ (40 mL) was added piperidine (4.67 mL, 47.2 mmol) dropwise. The reaction mixture was stirred at rt for 2 h and concentrated in vacuo. The residue was washed with methanol and the resulting solid was removed by filtration. The filtrate was concentrated in vacuo and purified by flash column chromatography (gradient elution from 0 to 10% MeOH/CH₂Cl₂) to give the title compound (3.48 g, 79%) as a light tan solid. MS(ESI⁺) m/z 558.4 (M+H)⁺.

L) (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-phenethyl-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-N-phenethyl-1,2,3,4-tetrahydroisoquinoline-3-carboxamido)methyl)benzoic acid (40 mg, 0.056 mmol) in DMF (2 mL) were added HATU (28 mg, 0.073 mmol), tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (38 mg, 0.067 mmol), and DIEA (0.03 mL, 0.17 mmol). The reaction mixture was stirred at rt for 1 h and diluted with ethyl acetate and brine. The organic layer was washed successively with saturated aq. NaHCO₃ solution and 1 N HCl solution. The organic layer was dried over MgSO₄ and the filtrate was concentrated in vacuo to give a light brown oil.

To the above crude oil (40 mg, 0.032 mmol) in DCM (2 mL) was added TFA (0.8 mL, 10 mmol). The reaction mixture was stirred at rt for 1 h. The reaction mixture was concentrated in vacuo and the residue was purified by preparative HPLC. Fractions containing the desired product were combined, concentrated, and lyophilized to give the title compound as a white solid (2 TFA salt, 29 mg, 40%). MS(ESI⁺) m/z 1053.7 (M+H)⁺.

Example 3

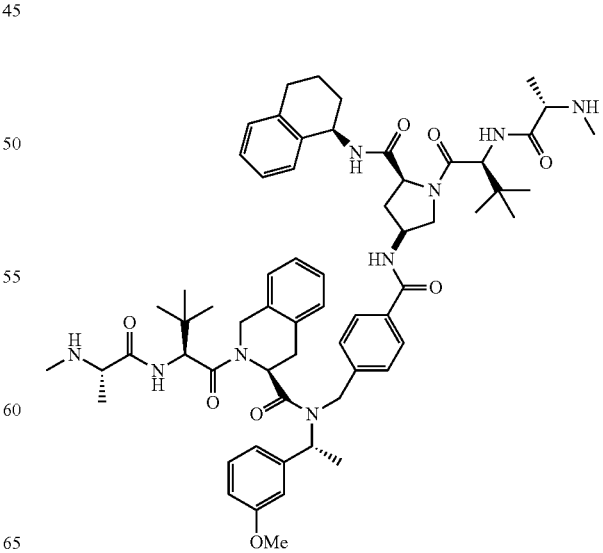

(S)-2-((S)-3,3-Dimethyl-2-((S)-2-(methylamino)
propanamido)butanoyl)-N-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)benzyl)-N-
((R)-1-(3-methoxyphenyl)ethyl)-1,2,3,4-
tetrahydroisoquinoline-3-carboxamide

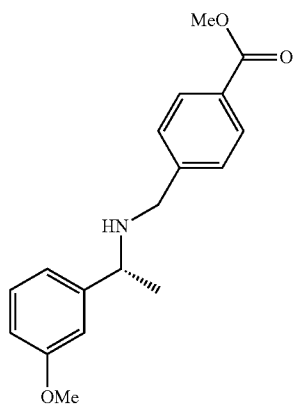 [SMILES: COC(=O)c1ccc(CN[C@H](C)c2cccc(OC)c2)cc1]

A) (R)-Methyl 4-(((1-(3-methoxyphenyl)ethyl)
amino)methyl)benzoate

To a solution of methyl 4-(bromomethyl)benzoate (0.50 g, 2.2 mmol) in DMF (10 mL) was added (R)-1-(3-methoxyphenyl)ethanamine (0.38 g, 2.5 mmol) and K$_2$CO$_3$ (0.60 g, 4.4 mmol). The reaction mixture was stirred at rt for 2 h and diluted with ethyl acetate and water. The organic layer was separated, washed with brine, and dried over MgSO$_4$. The filtrate was concentrated in vacuo and the residue was purified by flash chromatography (eluting with 20% EtOAc/DCM) to afford the title compound as a white solid (0.52 g, 79%). $^1$H NMR (CDCl$_3$) δ 7.99 (d, J=8.4 Hz, 2H), 7.37 (d, J=8.6 Hz, 2H), 7.30-7.22 (m, 1H), 7.00-6.90 (m, 2H), 6.81 (ddd, J=8.3, 2.5, 1.1 Hz, 1H), 3.92 (s, 3H), 3.83 (s, 3H), 3.80-3.74 (m, 1H), 3.75-3.61 (m, 2H), 1.38 (d, J=6.6 Hz, 3H); MS(ESI$^+$) m/z 300.3 (M+H)$^+$.

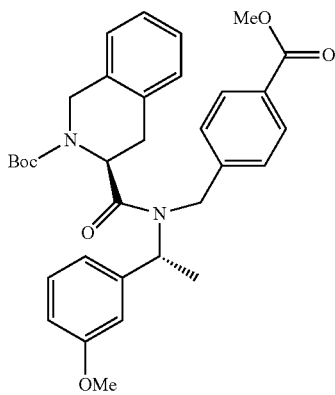

B) (S)-tert-Butyl 3-((4-(methoxycarbonyl)benzyl)
((R)-1-(3-methoxyphenyl)ethyl)carbamoyl)-3,4-
dihydroisoquinoline-2(1H)-carboxylate To a solution of (S)-2-(tert-butoxycarbonyl)-1,2,3,4-tetrahydroisoquinoline-3-carboxylic acid (296 mg, 1.07 mmol) in DCE (8 mL) were added 4-(4,6-dimethoxy[1.3.5]triazin-2-yl)-4-methylmorpholinium chloride hydrate (333 mg, 1.20 mmol, source: Oakwood), a solution of (R)-methyl 4-(((1-(3-methoxyphenyl)ethyl)amino)methyl)benzoate (200 mg, 0.67 mmol) in DCE (2 mL) and DIEA (0.23 mL, 1.34 mmol). The reaction mixture was stirred at rt overnight and diluted with DCM and brine. The organic layer was separated and concentrated in vacuo. The residue was dissolved in MeOH and filtered. The filtrate was purified by preparative HPLC. Fractions containing the product were combined, concentrated, and lyophilized to give the title compound as a white solid (175 mg, 46%). $^1$H NMR (CDCl$_3$) δ 8.05 (d, J=7.9 Hz, 1H), 7.84 (d, J=8.4 Hz, 1H), 7.40-7.28 (m, 1H), 7.24-6.69 (m, 8H), 6.12 (d, J=7.5 Hz, 0.5H), 5.54 (d, J=6.8 Hz, 0.5H), 5.42-5.06 (m, 1H), 4.96-4.63 (m, 2H), 4.61-4.41 (m, 1H), 4.34-4.01 (m, 1H), 3.99-3.85 (m, 3H), 3.80 (d, J=2.0 Hz, 3H), 3.18-2.82 (m, 2H), 1.67-1.33 (m, 12H), 1.31-1.15 (m, 1H); MS(ESI$^+$) m/z 559.5 (M+H)$^+$.

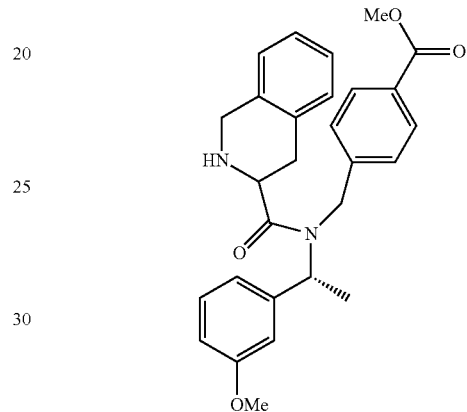

C) Methyl 4-(((S)-N-((R)-1-(3-methoxyphenyl)
ethyl)-1,2,3,4-tetrahydroisoquinoline-3-carbox-
amido)methyl)benzoate To a solution of (S)-tert-butyl 3-((4-(methoxycarbonyl)benzyl)((R)-1-(3-methoxyphenyl)ethyl)carbamoyl)-3,4-dihydroisoquinoline-2(1H)-carboxylate (170 mg, 0.30 mmol) in DCE (3 mL) was added HCl (4.0 N solution in dioxane, 3.0 mL, 12 mmol). The reaction mixture was stirred at rt for 1.5 h and concentrated in vacuo to give the title compound as a HCl salt (127 mg, 99%). The residue was directly used in the next step without purification. MS(ESI$^+$) m/z 459.4 (M+H)$^+$.

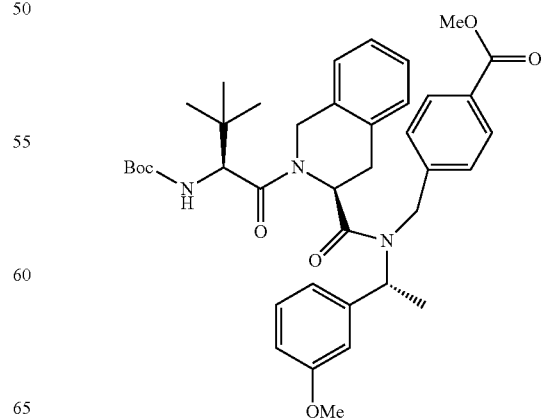

D) Methyl 4-(((S)-2-((S)-2-((tert-butoxycarbonyl)amino)-3,3-dimethylbutanoyl)-N-((R)-1-(3-methoxyphenyl)ethyl)-1,2,3,4-tetrahydroisoquinoline-3-carboxamido)methyl)benzoate To a solution of (S)-2-((tert-butoxycarbonyl)amino)-3,3-dimethylbutanoic acid (127 mg, 0.55 mmol) in DMF (2 mL) were added EDC (117 mg, 0.61 mmol), 3H-[1,2,3]-triazolo[4,5-b]pyridin-3-ol (42 mg, 0.31 mmol), a solution of methyl 4-(((S)-N-((R)-1-(3-methoxyphenyl)ethyl)-1,2,3,4-tetrahydroisoquinoline-3-carboxamido)methyl)benzoate, HCl (151 mg, 0.31 mmol) in DMF (2 mL) and 4-methylmorpholine (0.27 mL, 2.44 mmol). The reaction mixture was stirred at rt for 18 h and diluted with ethyl acetate and brine. The organic layer was separated, washed with saturated aq. NaHCO₃ solution, and dried over MgSO₄. The filtrate was concentrated in vacuo and the residue was purified by flash column chromatography (eluting with 20% EtOAc/DCM) to afford the title compound as a white solid (0.18 g, 86%). $^1$H NMR (CDCl₃) δ 8.06 (d, J=8.4 Hz, 1H), 7.90 (d, J=8.4 Hz, 1H), 7.44-7.28 (m, 3H), 7.25-7.12 (m, 3H), 7.04-6.70 (m, 4H), 6.14 (d, J=7.0 Hz, 0.5H), 5.65-5.26 (m, 1.5H), 5.16 (d, J=17.4 Hz, 1H), 5.10-4.90 (m, 1H), 4.82-4.41 (m, 2H), 4.36-4.19 (m, 1H), 3.98-3.86 (m, 3H), 3.84-3.76 (m, 3H), 2.99 (dd, J=14.6, 10.2 Hz, 1H), 2.62 (dd, J=15.0, 5.5 Hz, 0.5H), 2.45 (dd, J=14.9, 5.2 Hz, 0.5H), 1.58-1.56 (m, 1H), 1.41 (d, J=13.2 Hz, 9H), 1.14-1.00 (m, 11H); MS(ESI⁺) m/z 672.6 (M+H)⁺.

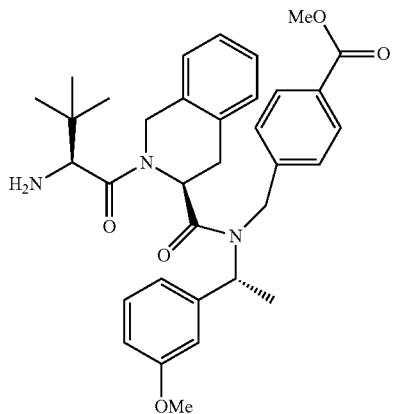 [SMILES: COC(=O)c1ccc(CN(C(=O)[C@@H]2Cc3ccccc3CN2C(=O)[C@@H](N)C(C)(C)C)[C@H](C)c2cccc(OC)c2)cc1]

E) Methyl 4-(((S)-2-((S)-2-amino-3,3-dimethylbutanoyl)-N-((R)-1-(3-methoxyphenyl)ethyl)-1,2,3,4-tetrahydroisoquinoline-3-carboxamido)methyl)benzoate To a solution of methyl 4-(((S)-2-((S)-2-((tert-butoxycarbonyl)amino)-3,3-dimethylbutanoyl)-N-((R)-1-(3-methoxyphenyl)ethyl)-1,2,3,4-tetrahydroisoquinoline-3-carboxamido)methyl)benzoate (176 mg, 0.26 mmol) in DCM (3 mL) was added TFA (1 mL, 12.98 mmol). The reaction mixture was stirred at rt for 1 h and concentrated in vacuo to give the title compound TFA salt (175 mg, 99%). The residue was directly used in the next step without purification. MS(ESI⁺) m/z 572.5 (M+H)⁺.

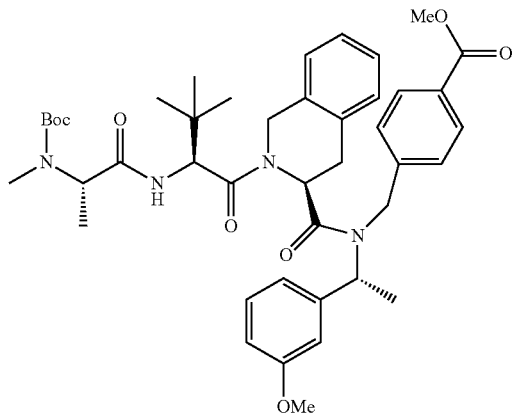 [SMILES: COC(=O)c1ccc(CN(C(=O)[C@@H]2Cc3ccccc3CN2C(=O)[C@@H](NC(=O)[C@H](C)N(C)C(=O)OC(C)(C)C)C(C)(C)C)[C@H](C)c2cccc(OC)c2)cc1]

F) Methyl 4-(((S)-2-((S)-2-((S)-2-((tert-butoxycarbonyl)(methyl)amino)propanamido)-3,3-dimethylbutanoyl)-N-((R)-1-(3-methoxyphenyl)ethyl)-1,2,3,4-tetrahydroisoquinoline-3-carboxamido)methyl)benzoate To a solution of (S)-2-((tert-butoxycarbonyl)(methyl)amino)propanoic acid (67 mg, 0.33 mmol) in DMF (2 mL) were added EDC (98 mg, 0.51 mmol), 3H-[1,2,3]-triazolo[4,5-b]pyridin-3-ol (35 mg, 0.26 mmol), a solution of methyl 4-(((S)-2-((S)-2-amino-3,3-dimethylbutanoyl)-N-((R)-1-(3-methoxyphenyl)ethyl)-1,2,3,4-tetrahydroisoquinoline-3-carboxamido)methyl)benzoate, TFA (175 mg, 0.26 mmol) in DMF (2 mL) and 4-methylmorpholine (0.17 mL, 1.53 mmol). The resulting reaction mixture was stirred at rt for 2 h and the reaction mixture was diluted with ethyl acetate and brine. The organic layer was separated, washed with saturated aq NaHCO₃ solution and brine. The organic layer was separated and dried over MgSO₄. The filtrate was concentrated in vacuo and the residue was purified by flash column chromatography (eluting with 20% EtOAc/DCM) to afford the title compound as a white solid (0.13 g, 68%). $^1$H NMR (CDCl₃) δ 8.06 (d, J=8.4 Hz, 1H), 7.89 (d, J=8.1 Hz, 1H), 7.42-7.28 (m, 2H), 7.25-7.09 (m, 2H), 7.04-6.63 (m, 5H), 6.22-5.48 (m, 1H), 5.21-4.90 (m, 4H), 4.75-4.53 (m, 2H), 4.47-4.18 (m, 2H), 4.01-3.86 (m, 3H), 3.82 (s, 3H), 2.98 (d, J=10.3 Hz, 1H), 2.82 (d, J=11.7 Hz, 3H), 2.68-2.31 (m, 1H), 1.62 (d, J=7.3 Hz, 1H), 1.56-1.43 (m, 9H), 1.35-1.23 (m, 4H), 1.07 (d, J=19.6 Hz, 10H); MS(ESI⁺) m/z 757.8 (M+H)⁺.

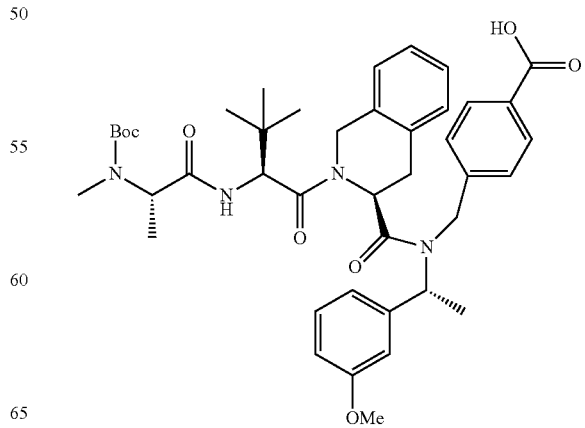

G) 4-(((S)-2-((S)-2-((S)-2-((tert-Butoxycarbonyl)(methyl)amino)propanamido)-3,3-dimethylbutanoyl)-N-((R)-1-(3-methoxyphenyl)ethyl)-1,2,3,4-tetrahydroisoquinoline-3-carboxamido)methyl)benzoic acid To a solution of methyl 4-(((S)-2-((S)-2-((S)-2-((tert-butoxycarbonyl)(methyl)amino)propanamido)-3,3-dimethylbutanoyl)-N-((R)-1-(3-methoxyphenyl)ethyl)-1,2,3,4-tetrahydroisoquinoline-3-carboxamido)methyl)benzoate (130 mg, 0.17 mmol) in THF (2 mL) and MeOH (1 mL) was added aq. NaOH solution (1.00 mL, 6.00 mmol). The reaction mixture was stirred at rt for 4 h and acidified with 1 N HCl solution. The resulting mixture was extracted with ethyl acetate (twice). The organic layer was separated, combined, and dried over $MgSO_4$. The filtrate was concentrated in vacuo to give the title compound as a white solid (105 mg, 90%). $^1$H NMR (CDCl$_3$) δ 8.12 (d, J=8.4 Hz, 0.5H), 7.96 (d, J=8.4 Hz, 1.5H), 7.48-7.30 (m, 2.5H), 7.25-7.10 (m, 2.5H), 7.05-6.62 (m, 4.5H), 6.13 (d, J=7.0 Hz, 0.5H), 5.57 (d, J=7.0 Hz, 0.5H), 5.22-4.92 (m, 3.5H), 4.78-4.55 (m, 2H), 4.47-4.19 (m, 1H), 3.83 (s, 3H), 3.10-2.93 (m, 1H), 2.88-2.73 (m, 3H), 2.64 (dd, J=14.9, 5.4 Hz, 0.5H), 2.42 (d, J=11.9 Hz, 0.5H), 1.67-1.55 (m, 3H), 1.54-1.43 (m, 9H), 1.36-1.24 (m, 4H), 1.16-0.95 (m, 9H); MS(ESI$^+$) m/z 743.8 (M+H)$^+$.

H) (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(3-methoxyphenyl)ethyl)-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-N-((R)-1-(3-methoxyphenyl)ethyl)-1,2,3,4-tetrahydroisoquinoline-3-carboxamido)methyl)benzoic acid (42 mg, 0.057 mmol) in DMF (1 mL) were added HATU (30 mg, 0.079 mmol), tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 41 mg, 0.073 mmol) and DIEA (0.02 mL, 0.11 mmol). The reaction mixture was stirred at rt for 1 h and diluted with ethyl acetate and brine. The organic layer was separated, washed with brine, and dried over $MgSO_4$. The filtrate was concentrated in vacuo and the residue was used in the next step without purification.

To a solution of the above residue (70 mg, 0.055 mmol) in DCM (2 mL) was added TFA (1.00 mL, 12.98 mmol). The reaction mixture was stirred at rt for 1 h and concentrated in vacuo. The residue was purified by preparative HPLC. Fractions containing the product were combined, concentrated, and lyophilized to give the title compound as a white solid (2 TFA salt, 54 mg, 74%). MS(ESI$^+$) m/z 1083.0 (M+H)$^+$.

Example 4

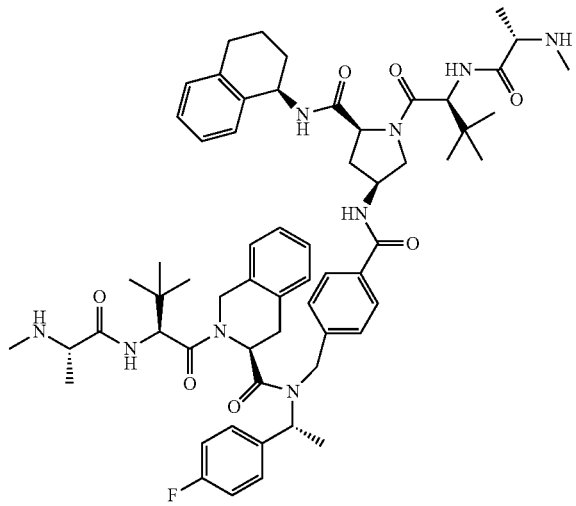

(S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(4-fluorophenyl)ethyl)-1,2,3,4-tetrahydroisoquinoline-3-carboxamide

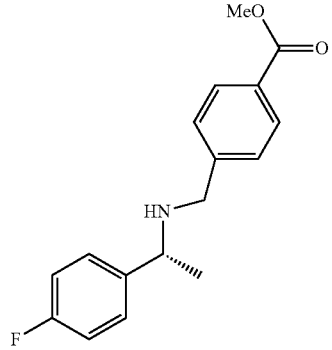 [SMILES: COC(=O)c1ccc(CN[C@H](C)c2ccc(F)cc2)cc1]

A) (R)-Methyl 4-(((1-(4-fluorophenyl)ethyl)amino)methyl)benzoate

To a solution of methyl 4-(bromomethyl)benzoate (320 mg, 1.40 mmol) in DMF (10 mL) were added (R)-1-(4-fluorophenyl)ethanamine (233 mg, 1.68 mmol, source: Synquest) and $K_2CO_3$ (386 mg, 2.79 mmol). The resulting reaction mixture was stirred at rt for 1 h and the reaction mixture was diluted with ethyl acetate and brine. The organic layer was separated and dried over $MgSO_4$. The filtrate was concentrated in vacuo to give the title compound as a colorless oil (400 mg, 100%). $^1$H NMR (CDCl$_3$) δ 7.99 (d, J=8.1 Hz, 2H), 7.39-7.28 (m, 4H), 7.10-6.97 (m, 2H), 3.92 (s, 3H), 3.85-3.57 (m, 3H), 1.36 (d, J=6.6 Hz, 3H); MS(ESI$^+$) m/z 288.1 (M+H)$^+$.

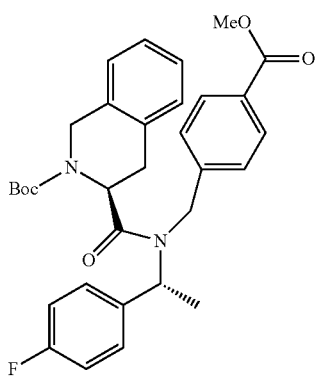

B) (S)-tert-Butyl 3-(((R)-1-(4-fluorophenyl)ethyl)(4-(methoxycarbonyl)benzyl)carbamoyl)-3,4-dihydroisoquinoline-2(1H)-carboxylate To a suspension of (S)-2-(tert-butoxycarbonyl)-1,2,3,4-tetrahydroisoquinoline-3-carboxylic acid (247 mg, 0.89 mmol) and 4-(4,6-dimethoxy[1,3,5]triazin-2-yl)-4-methylmorpholinium chloride hydrate (277 mg, 1.00 mmol, source: Oakwood) in DCM (6 mL) were added a solution of (R)-methyl 4-(((1-(4-fluorophenyl)ethyl)amino)methyl)benzoate (160 mg, 0.56 mmol) in DCM (2 mL) and 4-methylmorpholine (0.12 mL, 1.11 mmol). The reaction mixture was stirred at rt for over the weekend. The reaction mixture was diluted with DCM and brine. The organic layer was separated and concentrated in vacuo and the residue was purified by preparative HPLC. Fractions containing the desired product were combined, concentrated, and lyophilized to give the title compound as a white solid (80 mg, 26%). $^1$H NMR (CDCl$_3$) δ 8.06 (d, J=7.7 Hz, 1H), 7.84 (d, J=8.1 Hz, 1H), 7.44-7.30 (m, 2H), 7.25-6.76 (m, 8H), 5.60-5.32 (m, 1H), 5.22-5.09 (m, 0.5H), 4.89-4.41 (m, 2.5H), 4.29-4.04 (m, 1H), 3.99-3.84 (m, 3H), 3.12-2.82 (m, 2H), 2.71-2.41 (m, 2H), 1.62-1.44 (m, 11H), 1.32-1.11 (m, 1H); MS(ESI$^+$) m/z 547.4 (M+H)$^+$.

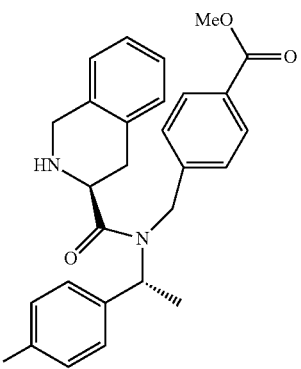

C) Methyl 4-(((S)-N-((R)-1-(4-fluorophenyl)ethyl)-1,2,3,4-tetrahydroisoquinoline-3-carboxamido)methyl)benzoate To a solution of (S)-tert-butyl 3-(((R)-1-(4-fluorophenyl)ethyl)(4-(methoxycarbonyl)benzyl)carbamoyl)-3,4-dihydroisoquinoline-2(1H)-carboxylate (80 mg, 0.15 mmol) in DCM (3.5 mL) was added HCl (4.0 M solution in dioxane, 1.5 mL, 6.00 mmol). The reaction mixture was stirred at rt for 2.5 h and concentrated in vacuo to give the title compound as a white solid (TFA salt, 70 mg, 99%). MS(ESI$^+$) m/z 447.3 (M+H)$^+$.

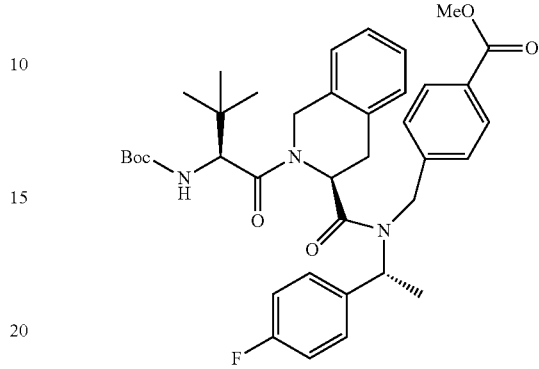

D) Methyl 4-(((S)-2-((S)-2-((tert-butoxycarbonyl)amino)-3,3-dimethylbutanoyl)-N-((R)-1-(4-fluorophenyl)ethyl)-1,2,3,4-tetrahydroisoquinoline-3-carboxamido)methyl)benzoate To a solution of (S)-2-((tert-butoxycarbonyl)amino)-3,3-dimethylbutanoic acid (44 mg, 0.19 mmol) in DMF (1 mL) were added EDC (39 mg, 0.20 mmol), 3H-[1,2,3]-triazolo[4,5-b]pyridin-3-ol (18 mg, 0.14 mmol), a solution of methyl 4-(((S)-N-((R)-1-(4-fluorophenyl)ethyl)-1,2,3,4-tetrahydroisoquinoline-3-carboxamido)methyl)benzoate, HCl (65 mg, 0.14 mmol) in DMF (1 mL) and 4-methylmorpholine (0.09 mL, 0.81 mmol). The reaction mixture was stirred at rt overnight and diluted with ethyl acetate and brine. The organic layer was separated and concentrated in vacuo and the resulting residue was purified by preparative HPLC. Fractions containing the product were combined, concentrated, and lyophilized to give the title compound as a white solid (52 mg, 58%). $^1$H NMR (CDCl$_3$) δ 8.07 (d, J=8.1 Hz, 1H), 7.89 (d, J=8.4 Hz, 1H), 7.45-7.34 (m, 2H), 7.24-7.08 (m, 5H), 7.04-6.81 (m, 2H), 6.77-6.11 (m, 1H), 5.65-5.27 (m, 1H), 5.22-4.87 (m, 2H), 4.82-4.53 (m, 2H), 4.43-4.15 (m, 1H), 4.01-3.87 (m, 3H), 3.10-2.92 (m, 1.5H), 2.69-2.39 (m, 1.5H), 1.59 (dd, J=18.2, 7.2 Hz, 3H), 1.45-1.34 (m, 9H), 1.16-1.01 (m, 9H); MS(ESI$^+$) m/z 660.4 (M+H)$^+$.

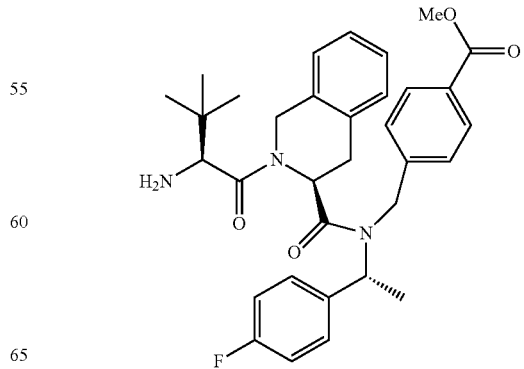

E) Methyl 4-(((S)-2-((S)-2-amino-3,3-dimethylbutanoyl)-N-((R)-1-(4-fluorophenyl)ethyl)-1,2,3,4-tetrahydroisoquinoline-3-carboxamido)methyl)benzoate To a solution of methyl 4-(((S)-2-((S)-2-((tert-butoxycarbonyl)amino)-3,3-dimethylbutanoyl)-N-((R)-1-(4-fluorophenyl)ethyl)-1,2,3,4-tetrahydroisoquinoline-3-carboxamido)methyl)benzoate (52 mg, 0.079 mmol) in DCM (1.5 mL) was added TFA (0.3 mL, 3.89 mmol). The reaction mixture was stirred at rt for 0.8 h and concentrated in vacuo to give the title compound as a white solid (TFA salt, 52 mg, 98%). MS(ESI$^+$) m/z 560.4 (M+H)$^+$.

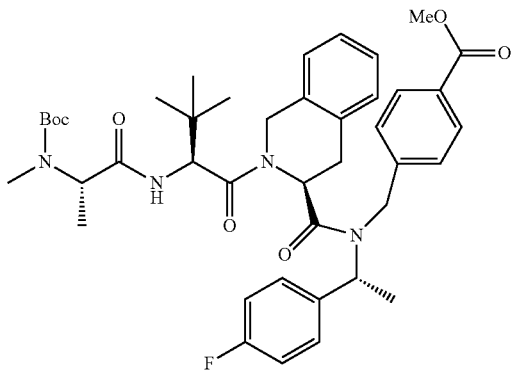 [SMILES: COC(=O)c1ccc(CN(C(=O)[C@@H]2Cc3ccccc3CN2C(=O)[C@@H](NC(=O)[C@H](C)N(C)C(=O)OC(C)(C)C)C(C)(C)C)[C@H](C)c2ccc(F)cc2)cc1]

F) Methyl 4-(((S)-2-((S)-2-((S)-2-((tert-butoxycarbonyl)(methyl)amino)propanamido)-3,3-dimethylbutanoyl)-N-((R)-1-(4-fluorophenyl)ethyl)-1,2,3,4-tetrahydroisoquinoline-3-carboxamido)methyl)benzoate To a solution of (S)-2-((tert-butoxycarbonyl)(methyl)amino)propanoic acid (19 mg, 0.091 mmol) in DMF (1 mL) were added EDC (22 mg, 0.11 mmol), 3H-[1,2,3]-triazolo[4,5-b]pyridin-3-ol (10 mg, 0.076 mmol), a solution of methyl 4-(((S)-2-((S)-2-amino-3,3-dimethylbutanoyl)-N-((R)-1-(4-fluorophenyl)ethyl)-1,2,3,4-tetrahydroisoquinoline-3-carboxamido)methyl)benzoate, TFA (51 mg, 0.076 mmol) in DMF (1 mL) and 4-methylmorpholine (0.05 mL, 0.45 mmol). The resulting reaction mixture was stirred at rt for 1 h and diluted with ethyl acetate and brine. The organic layer was separated and concentrated in vacuo. The residue was purified by preparative HPLC. Fractions containing the product were combined and concentrated to give the title compound as a white solid (50 mg, 88%). MS(ESI$^+$) m/z 745.6 (M+H)$^+$.

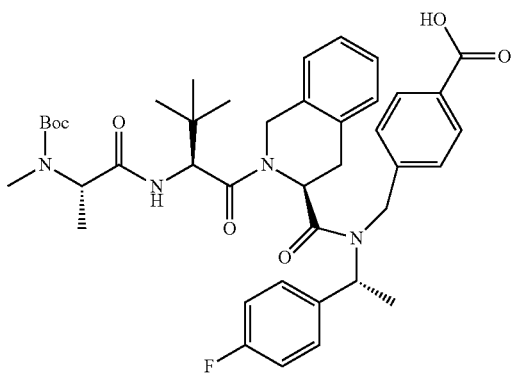 [SMILES: C[C@H](c1ccc(F)cc1)N(Cc1ccc(C(=O)O)cc1)C(=O)[C@@H]1Cc2ccccc2CN1C(=O)[C@@H](NC(=O)[C@H](C)N(C)C(=O)OC(C)(C)C)C(C)(C)C]

G) 4-(((S)-2-((S)-2-((S)-2-((tert-Butoxycarbonyl)(methyl)amino)propanamido)-3,3-dimethylbutanoyl)-N-((R)-1-(4-fluorophenyl)ethyl)-1,2,3,4-tetrahydroisoquinoline-3-carboxamido)methyl)benzoic acid To a solution of methyl 4-(((S)-2-((S)-2-((S)-2-((tert-butoxycarbonyl)(methyl)amino)propanamido)-3,3-dimethylbutanoyl)-N-((R)-1-(4-fluorophenyl)ethyl)-1,2,3,4-tetrahydroisoquinoline-3-carboxamido)methyl)benzoate (50 mg, 0.067 mmol) in THF (1 mL) and MeOH (0.5 mL) was added aq. LiOH solution (1.4 mL, 2.80 mmol). The reaction mixture was stirred at rt overnight and treated with 1 N HCl solution to adjust the pH to 1. The resulting mixture was extracted with ethyl acetate. The organic layer was separated and dried over MgSO$_4$. The filtrate was concentrated in vacuo to give the title compound as a white solid (42 mg, 86%). MS(ESI$^+$) m/z 731.6 (M+H)$^+$.

H) (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(4-fluorophenyl)ethyl)-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-N-((R)-1-(4-fluorophenyl)ethyl)-1,2,3,4-tetrahydroisoquinoline-3-carboxamido)methyl)benzoic acid (42 mg, 0.057 mmol) in DMF (1.5 mL) were added HATU (31 mg, 0.08 mmol), tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 41 mg, 0.073 mmol), and 4-methylmorpholine (0.02 mL, 0.17 mmol). The reaction mixture was stirred at rt for 1 h and concentrated in vacuo. The residue was purified by preparative HPLC. Fractions containing the product were combined, and concentrated to give white solid.

To a solution of the above intermediate (42 mg, 0.033 mmol) in DCM (1.5 mL) was added TFA (0.3 mL, 3.89 mmol). The reaction mixture was stirred at rt for 65 min and concentrated in vacuo. The residue was lyophilized to give the title compound as a white solid (39 mg, 51%). MS(ESI$^+$) m/z 1070.8 (M+H)$^+$.

Example 5

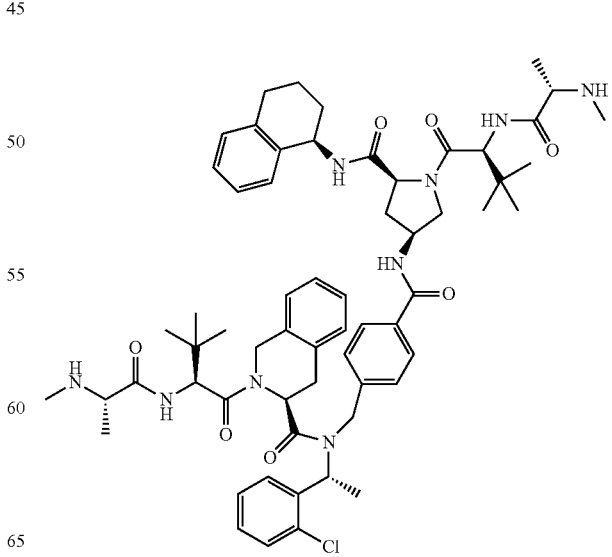

(S)-N-((R)-1-(2-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide

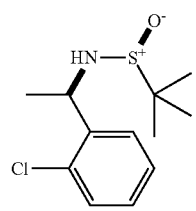 [SMILES: C[C@@H](N[S@@+]([O-])C(C)(C)C)c1ccccc1Cl]

A) N-((R)-1-(2-Chlorophenyl)ethyl)-2-methylpropane-2-sulfinamide

To a solution of 1-(2-chlorophenyl)ethanone (3.36 mL, 25.90 mmol) in THF (35 mL) were added tetraisopropoxytitanium (15.2 mL, 51.7 mmol, source: Aldrich) and 2-methylpropane-2-sulfinamide (3.76 g, 31.0 mmol, source: Oakwood) under nitrogen. The reaction mixture was heated at 71° C. for 16 h, cooled to rt, and then to −40° C. with dry ice-isopropanol cooling bath. To the reaction mixture was added NaBH$_4$ (3.92 g, 103 mmol) portionwise, and the resulting reaction mixture was stirred at −40° C. for 1.5 h and then at rt for 1.5 h. The mixture was then treated with ~10 mL of MeOH dropwise at dry ice bath temperature until gas evolution ceased. Water was then added to the resulting mixture with rapid stirring. The resulting suspension was filtered through a CELITE® pad and the solid was washed with ethyl acetate. The filtrates were combined and extracted with ethyl acetate. The organic layer was separated and dried over MgSO$_4$. The filtrate was concentrated in vacuo and the resulting residue was purified by flash column chromatography (eluting with 40% EtOAc/hexane) to afford the title compound as a white solid (1.1 g, 17%). $^1$H NMR (CDCl$_3$) δ 7.46 (dd, J=7.7, 1.8 Hz, 1H), 7.37 (dd, J=7.9, 1.3 Hz, 1H), 7.32-7.28 (m, 1H), 7.25-7.18 (m, 1H), 5.01 (dd, J=6.6, 4.2 Hz, 1H), 3.57 (d, J=3.5 Hz, 1H), 1.53 (d, J=6.6 Hz, 3H), 1.25 (s, 9H); MS(ESI$^+$) m/z 260.2 (M+H)$^+$.

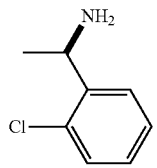

B) (R)-1-(2-Chlorophenyl)ethanamine

To a solution of N-((R)-1-(2-chlorophenyl)ethyl)-2-methylpropane-2-sulfinamide (1.09 g, 4.20 mmol) in MeOH (8 mL) was added HCl (4.0 M solution in dioxane, 3 mL, 12.00 mmol) and the resulting mixture was stirred at rt for 1 h. The reaction mixture was concentrated in vacuo and the residue was treated with Et$_2$O. The solid that crashed out was filtered and dissolved in ethyl acetate and saturated aq. NaHCO$_3$ solution. The organic layer was separated, combined (twice), and dried over MgSO$_4$. The filtrate was concentrated in vacuo to give the title compound as a colorless oil (0.56 g, 86%). $^1$H NMR (CDCl$_3$) δ 7.53 (dd, J=7.8, 1.7 Hz, 1H), 7.34 (dd, J=7.8, 1.2 Hz, 1H), 7.30-7.24 (m, 1H), 7.21-7.10 (m, 1H), 4.55 (q, J=6.6 Hz, 1H), 1.40 (d, J=6.6 Hz, 3H); MS(ESI$^+$) m/z 311.0 (2M+H)$^+$.

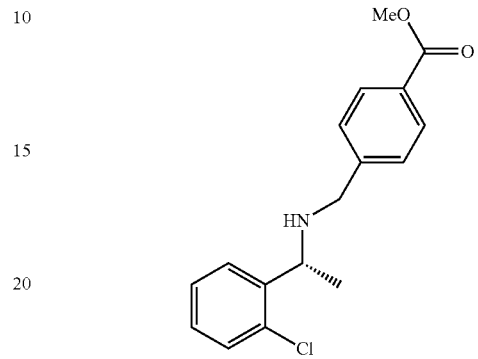

C) (R)-Methyl 4-(((1-(2-chlorophenyl)ethyl)amino)methyl)benzoate

To a solution of (R)-1-(2-chlorophenyl)ethanamine (285 mg, 1.83 mmol) in DMF (7 mL) were added methyl 4-(bromomethyl)benzoate (365 mg, 1.59 mmol) and K$_2$CO$_3$ (352 mg, 2.55 mmol). The reaction mixture was stirred at rt for 2 h and diluted with ethyl acetate and brine. The organic layer was separated, washed with brine and dried over MgSO$_4$. The filtrate was concentrated in vacuo and the residue was purified by flash column chromatography (eluting with 20% EtOAc/hexane) to afford the title compound as a white solid (0.48 g, 99%). $^1$H NMR (CDCl$_3$) δ 7.99 (d, J=8.4 Hz, 2H), 7.59 (dd, J=7.7, 1.8 Hz, 1H), 7.42-7.33 (m, 3H), 7.30 (td, J=7.5, 1.2 Hz, 1H), 7.25-7.13 (m, 1H), 4.34 (q, J=6.5 Hz, 1H), 3.92 (s, 3H), 3.77-3.63 (m, 2H), 1.37 (d, J=6.6 Hz, 3H); MS(ESI$^+$) m/z 304.2 (M+H)$^+$.

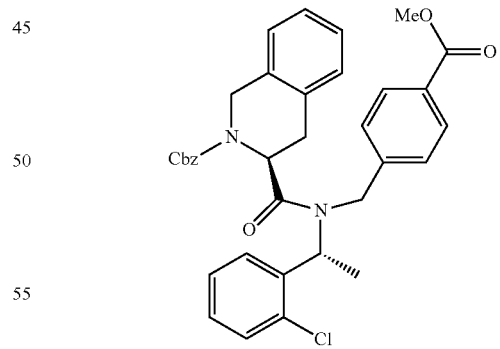

D) (S)-Benzyl 3-(((R)-1-(2-chlorophenyl)ethyl)(4-(methoxycarbonyl)benzyl)carbamoyl)-3,4-dihydroisoquinoline-2(1H)-carboxylate To a solution of (S)-2-((benzyloxy)carbonyl)-1,2,3,4-tetrahydroisoquinoline-3-carboxylic acid (203 mg, 0.65 mmol, source: Chem-Impex International) in DCM (4.00 mL) was added 1-chloro-N,N,2-trimethylprop-1-en-1-amine (0.11 mL, 0.82 mmol, source: Aldrich). The reaction mixture was stirred at rt for 15 min and treated with a solution of (R)-methyl 4-(((1-(2-chlorophenyl)ethyl)amino)methyl)benzoate (165 mg, 0.54 mmol) in DCM (2 mL) followed by DIEA (0.19 mL, 1.09 mmol). The resulting reaction mixture was stirred at rt for 1 h and concentrated in vacuo. The residue was purified by preparative HPLC. Fractions containing the desired product were combined, concentrated, and lyophilized to give the title compound as a white solid (310 mg, 94%). $^1$H NMR (CDCl$_3$) δ 8.08-7.71 (m, 2H), 7.48-6.83 (m, 15H), 5.98-5.75 (m, 1H), 5.47-4.34 (m, 8H), 4.02-3.76 (m, 3H), 3.13-2.59 (m, 2H), 1.71-1.38 (m, 2H), 1.09 (d, J=6.8 Hz, 1H); MS(ESI$^+$) m/z 597.3 (M+H)$^+$.

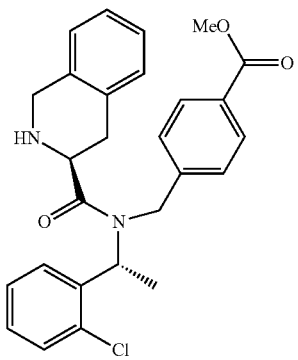 [SMILES: COC(=O)c1ccc(CN(C(=O)[C@@H]2Cc3ccccc3CN2)[C@H](C)c2ccccc2Cl)cc1]

E) Methyl 4-(((S)-N-((R)-1-(2-chlorophenyl)ethyl)-1,2,3,4-tetrahydroisoquinoline-3-carboxamido)methyl)benzoate To a solution of (S)-benzyl 3-(((R)-1-(2-chlorophenyl)ethyl)(4-(methoxycarbonyl)benzyl)carbamoyl)-3,4-dihydroisoquinoline-2(1H)-carboxylate (180 mg, 0.30 mmol) in DCE (4 mL) was added BBr$_3$ (0.17 mL, 1.81 mmol) at ice bath temperature under nitrogen. The reaction mixture was stirred at ice bath temperature for 1 h and warmed to rt. The reaction mixture was treated with MeOH and the resulting mixture was concentrated in vacuo. The residue was purified by preparative HPLC. Fractions containing the product were combined, concentrated in vacuo to give the title compound as a white solid (TFA salt, 122 mg, 70%). $^1$H NMR (DMSO-d$_6$) δ 7.73 (dd, J=8.4, 2.0 Hz, 2H), 7.67-7.38 (m, 1.5H), 7.35-7.09 (m, 7.5H), 7.06 (d, J=8.4 Hz, 1H), 5.93-5.52 (m, 1H), 4.87-4.23 (m, 5H), 3.82 (d, J=3.5 Hz, 3H), 3.32-2.93 (m, 2H), 1.66-1.45 (m, 3H); MS(ESI$^+$) m/z 463.3 (M+H)$^+$.

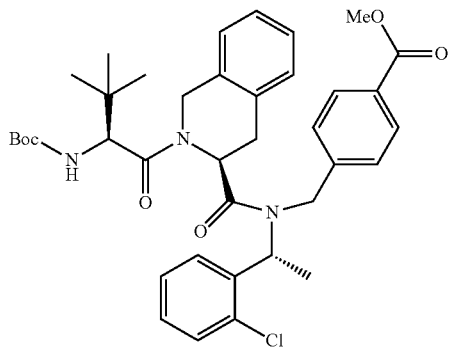 [SMILES: COC(=O)c1ccc(CN(C(=O)[C@@H]2Cc3ccccc3CN2C(=O)[C@@H](NC(=O)OC(C)(C)C)C(C)(C)C)[C@H](C)c2ccccc2Cl)cc1]

F) Methyl 4-(((S)-2-((S)-2-((tert-butoxycarbonyl)amino)-3,3-dimethylbutanoyl)-N-((R)-1-(2-chlorophenyl)ethyl)-1,2,3,4-tetrahydroisoquinoline-3-carboxamido)methyl)benzoate To a solution of (S)-2-((tert-butoxycarbonyl)amino)-3,3-dimethylbutanoic acid (60 mg, 0.26 mmol) in DMF (2 mL) were added EDC (60 mg, 0.31 mmol), 3H-[1,2,3]-triazolo[4,5-b]pyridin-3-ol (28 mg, 0.21 mmol), a solution of methyl 4-(((S)-N-((R)-1-(2-chlorophenyl)ethyl)-1,2,3,4-tetrahydroisoquinoline-3-carboxamido)methyl)benzoate, TFA (120 mg, 0.21 mmol) in DMF (2 mL) and 4-methylmorpholine (0.14 mL, 1.25 mmol). The reaction mixture was stirred at rt for 16 h and diluted with ethyl acetate and brine. The organic layer was separated and washed with saturated aq. NaHCO$_3$ solution and brine, successively. The organic layer was separated and dried over MgSO$_4$. The filtrate was concentrated in vacuo and the resulting residue was purified by flash column chromatography (eluting with 15% EtOAc/DCM) to afford the title compound as a white solid (0.11 g, 78%). $^1$H NMR (CDCl$_3$) δ 8.16-7.83 (m, 2H), 7.50-7.29 (m, 5H), 7.25-7.09 (m, 3H), 6.91-6.69 (m, 1H), 6.08-5.86 (m, 1H), 5.57-5.23 (m, 2H), 5.05-4.69 (m, 3H), 4.68-4.42 (m, 2H), 4.01-3.81 (m, 3H), 3.03-2.81 (m, 1H), 2.63-2.30 (m, 1H), 1.69-1.50 (m, 3H), 1.46-1.35 (m, 9H), 1.14-0.85 (m, 9H); MS(ESI$^+$) m/z 676.5 (M+H)$^+$.

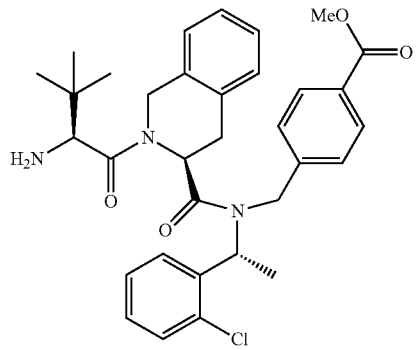 [SMILES: COC(=O)c1ccc(CN(C(=O)[C@@H]2Cc3ccccc3CN2C(=O)[C@@H](N)C(C)(C)C)[C@H](C)c2ccccc2Cl)cc1]

G) Methyl 4-(((S)-2-((S)-2-amino-3,3-dimethylbutanoyl)-N-((R)-1-(2-chlorophenyl)ethyl)-1,2,3,4-tetrahydroisoquinoline-3-carboxamido)methyl)benzoate To a solution of methyl 4-(((S)-2-((S)-2-((tert-butoxycarbonyl)amino)-3,3-dimethylbutanoyl)-N-((R)-1-(2-chlorophenyl)ethyl)-1,2,3,4-tetrahydroisoquinoline-3-carboxamido)methyl)benzoate (105 mg, 0.16 mmol) in DCM (2 mL) was added TFA (0.40 mL, 5.19 mmol). The reaction mixture was stirred at rt for 1 h and concentrated in vacuo to give the title compound as a white solid (TFA salt, 109 mg, 100%). $^1$H NMR (DMSO-d$_6$) δ 8.17-7.90 (brm, 2H), 7.88-7.76 (m, 2H), 7.66-7.31 (m, 6H), 7.28-7.02 (m, 3H), 6.61 (d, J=6.8 Hz, 1H), 6.03-5.83 (m, 1H), 5.32-4.72 (m, 3H), 4.64-4.31 (m, 3H), 3.87-3.76 (m, 3H), 3.06-2.61 (m, 1H), 1.90 (dd, J=14.4, 4.7 Hz, 1H), 1.52-1.39 (m, 3H), 1.14-0.96 (m, 9H); MS(ESI$^+$) m/z 576.4 (M+H)$^+$.

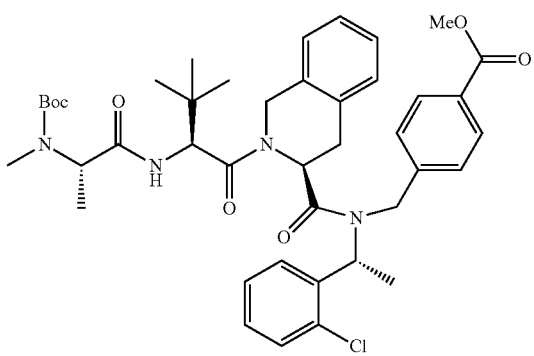 [SMILES: COC(=O)c1ccc(CN(C(=O)[C@@H]2Cc3ccccc3CN2C(=O)[C@@H](NC(=O)[C@H](C)N(C)C(=O)OC(C)(C)C)C(C)(C)C)[C@H](C)c2ccccc2Cl)cc1]

H) Methyl 4-(((S)-2-((S)-2-((S)-2-((tert-butoxycarbonyl)(methyl)amino)propanamido)-3,3-dimethylbutanoyl)-N-((R)-1-(2-chlorophenyl)ethyl)-1,2,3,4-tetrahydroisoquinoline-3-carboxamido)methyl)benzoate To a solution of (S)-2-((tert-butoxycarbonyl)(methyl)amino)propanoic acid (41 mg, 0.20 mmol) in DMF (2 mL) were added EDC (48 mg, 0.25 mmol), 3H-[1,2,3]-triazolo[4,5-b]pyridin-3-ol (21 mg, 0.16 mmol), a solution of methyl 4-(((S)-2-((S)-2-amino-3,3-dimethylbutanoyl)-N-((R)-1-(2-chlorophenyl)ethyl)-1,2,3,4-tetrahydroisoquinoline-3-carboxamido)methyl)benzoate, TFA (107 mg, 0.16 mmol) in DMF (2 mL) and 4-methylmorpholine (0.10 mL, 0.93 mmol). The reaction mixture was stirred at rt for 1-2 h and diluted with ethyl acetate and brine. The organic layer was separated and washed with saturated aq. NaHCO$_3$ solution and brine, successively. The organic layer was separated and dried over MgSO$_4$. The filtrate was concentrated in vacuo to give the title compound as a white solid (100 mg, 85%). The product was used directly in the next step without purification. MS(ESI$^+$) m/z 761.5 (M+H)$^+$.

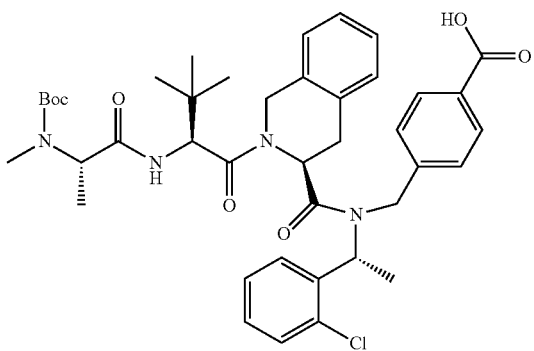 [SMILES: C[C@H](c1ccccc1Cl)N(Cc1ccc(C(=O)O)cc1)C(=O)[C@@H]1Cc2ccccc2CN1C(=O)[C@@H](NC(=O)[C@H](C)N(C)C(=O)OC(C)(C)C)C(C)(C)C]

I) 4-(((S)-2-((S)-2-((S)-2-((tert-Butoxycarbonyl)(methyl)amino)propanamido)-3,3-dimethylbutanoyl)-N-((R)-1-(2-chlorophenyl)ethyl)-1,2,3,4-tetrahydroisoquinoline-3-carboxamido)methyl)benzoic acid To a solution of methyl 4-(((S)-2-((S)-2-((S)-2-((tert-butoxycarbonyl)(methyl)amino)propanamido)-3,3-dimethylbutanoyl)-N-((R)-1-(2-chlorophenyl)ethyl)-1,2,3,4-tetrahydroisoquinoline-3-carboxamido)methyl)benzoate (100 mg, 0.13 mmol) in THF (2 mL) and MeOH (1 mL) was added 2 M LiOH solution (1.6 mL, 3.20 mmol). The reaction mixture was stirred at rt for 3 h and acidified with 1N HCl solution to adjust the pH to 1. The resulting mixture was extracted with ethyl acetate. The organic layer was concentrated in vacuo and the resulting residue was purified by preparative HPLC. Fractions containing the product were combined, and concentrated to give the title compound as a white solid (100 mg, 100%). $^1$H NMR (DMSO-d$_6$) δ 7.89-7.69 (m, 2H), 7.61-7.41 (m, 3.5H), 7.36-7.07 (m, 6H), 6.66 (d, J=5.9 Hz, 0.5H), 6.00-5.67 (m, 1H), 5.20-4.77 (m, 3.5H), 4.72-4.40 (m, 3.5H), 2.94-2.68 (m, 3H), 2.69-2.60 (m, 1H), 2.14-1.98 (m, 1H), 1.50-1.33 (m, 12H), 1.17-1.07 (m, 3H), 1.03-0.87 (m, 9H); MS(ESI$^+$) m/z 747.5 (M+H)$^+$.

J) (S)-N-((R)-1-(2-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-N-((R)-1-(2-chlorophenyl)ethyl)-1,2,3,4-tetrahydroisoquinoline-3-carboxamido)methyl)benzoic acid (105 mg, 0.14 mmol) in DMF (2 mL) were added HATU (75 mg, 0.20 mmol), tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 94 mg, 0.17 mmol) and 4-methylmorpholine (0.05 mL, 0.42 mmol). The reaction mixture was stirred at rt for 1 h and diluted with ethyl acetate and brine. The organic layer was separated and dried over MgSO$_4$. The filtrate was concentrated in vacuo.

To a solution of the above crude product (110 mg, 0.085 mmol) in DCM (3 mL) was added TFA (0.6 mL, 7.79 mmol). The reaction mixture was stirred at rt for 1.5 h and concentrated in vacuo. The residue was purified by preparative HPLC. Fractions containing the product were combined and concentrated in vacuo. The residue was extracted with ethyl acetate and saturated aq. NaHCO$_3$ solution. The organic layer was separated and concentrated in vacuo. The residue was dissolved in DCM and treated with 0.5 mL of 4N HCl solution in dioxane with stirring. The mixture was concentrated in vacuo to give the title compound as a white solid (2 HCl salt, 74 mg, 50%). MS(ESI$^+$) m/z 1086.7 (M+H)$^+$.

Example 6

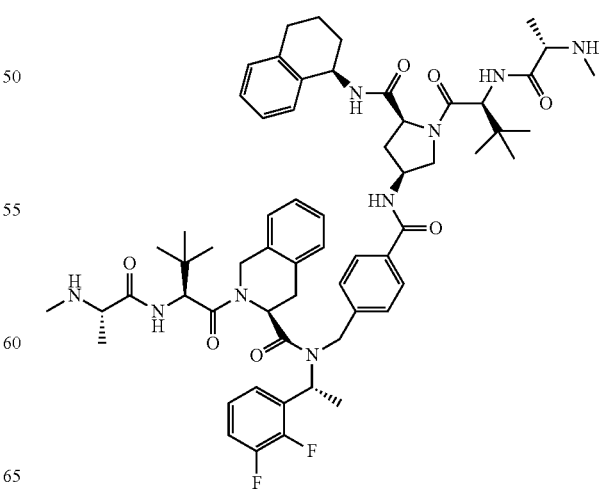

(S)-N-((R)-1-(2,3-Difluorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide and the solid was filtered off. The white solid was extracted with ethyl acetate and saturated aq. NaHCO$_3$ solution. The organic layer was separated and dried over MgSO$_4$. The filtrate was concentrated in vacuo to give the title compound as a colorless oil (1.0 g, 79%). $^1$H NMR (DMSO-d$_6$) δ 7.42-7.34 (m, 1H), 7.29-7.09 (m, 2H), 4.27 (q, J=6.6 Hz, 1H), 1.91 (br. s., 2H), 1.26 (d, J=6.8 Hz, 3H); MS(ESI$^+$) m/z 315.0 (2M+H)$^+$.

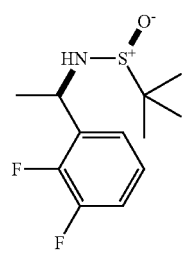 [SMILES: C[C@@H](N[S@@+]([O-])C(C)(C)C)c1cccc(F)c1F]

A) N-((R)-1-(2,3-Difluorophenyl)ethyl)-2-methylpropane-2-sulfinamide

To a solution of 1-(2,3-difluorophenyl)ethanone (4.00 g, 25.60 mmol, source: ALFA AESAR®) in THF (40 mL) were added tetraisopropoxytitanium (15.0 mL, 51.2 mmol) and (R)-tert-butyl sulfinamide (4.35 g, 35.9 mmol) under nitrogen. The reaction mixture was heated to 74° C. for 24 h, cooled to room temperature then cooled to −40° C. with dry ice-isopropanol cooling bath. The reaction mixture was treated with NaBH$_4$ (3.39 g, 90.0 mmol) portionwise and the mixture was stirred at −40° C. for 2 h. About 10 mL of MeOH was added dropwise to the solution at dry ice bath temperature until gas evolution ceased. Water was then added to the mixture with rapid stirring. The resulting suspension was filtered through a CELITE® pad and the solid was washed with ethyl acetate. The filtrate was combined, extracted with ethyl acetate twice. The organic layers were combined and dried over MgSO$_4$. The filtrate was concentrated in vacuo and the resulting residue was purified by flash column chromatography (eluting with 40% EtOAc/hexane) to afford the title compound as a white solid (2.1 g, 31%). $^1$H NMR (CDCl$_3$) δ 7.17-7.01 (m, 3H), 4.81 (dd, J=6.6, 5.7 Hz, 1H), 3.54 (d, J=5.3 Hz, 1H), 1.56 (d, J=6.6 Hz, 3H), 1.24 (s, 9H); MS(ESI$^+$) m/z 262.1 (M+H)$^+$.

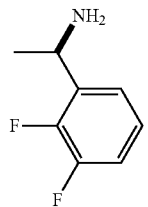

B) (R)-1-(2,3-Difluorophenyl)ethanamine

To a solution of N-((R)-1-(2,3-difluorophenyl)ethyl)-2-methylpropane-2-sulfinamide (2.1 g, 8.0 mmol) in DCM (8 mL) was added HCl (4.0 M solution in dioxane, 6.0 mL, 24 mmol) with stirring. After 5 min, a solid appeared. The reaction mixture was stirred at rt for 2 more hours and concentrated in vacuo. The residue was triturated with ether

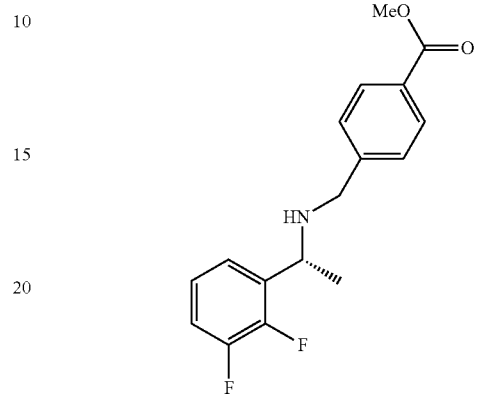

C) (R)-Methyl 4-(((1-(2,3-difluorophenyl)ethyl)amino)methyl)benzoate

To a solution of (R)-1-(2,3-difluorophenyl)ethanamine (0.31 g, 2.0 mmol) in DMF (8 mL) were added methyl 4-(bromomethyl)benzoate (0.42 g, 1.8 mmol) and K$_2$CO$_3$ (0.41 g, 2.9 mmol). The resulting suspension was stirred at rt for 1 h and diluted with ethyl acetate and brine. The organic layer was separated, washed with brine, and dried over MgSO$_4$. The filtrate was concentrated in vacuo to give the title compound as a white solid (0.59 g, 99%). $^1$H NMR (CDCl$_3$) δ 7.99 (d, J=8.4 Hz, 2H), 7.38 (d, J=8.6 Hz, 2H), 7.25-7.18 (m, 1H), 7.12-6.99 (m, 2H), 4.18 (q, J=6.6 Hz, 1H), 3.79-3.61 (m, 2H), 1.43 (d, J=6.8 Hz, 3H); MS(ESI$^+$) m/z 306.3 (M+H)$^+$.

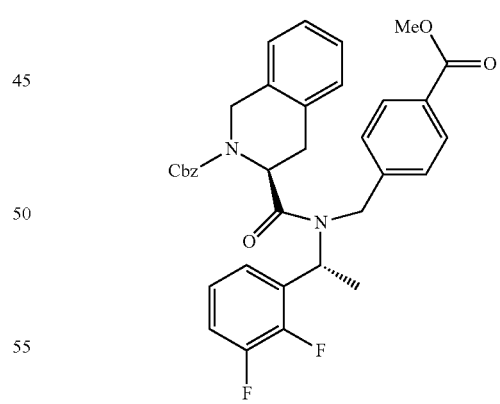

D) (S)-Benzyl 3-(((R)-1-(2,3-difluorophenyl)ethyl)(4-(methoxycarbonyl)benzyl)carbamoyl)-3,4-dihydroisoquinoline-2(1H)-carboxylate To a solution of (S)-2-((benzyloxy)carbonyl)-1,2,3,4-tetrahydroisoquinoline-3-carboxylic acid (208 mg, 0.67 mmol) in DCM (4 mL) was added 1-chloro-N,N,2-trimethylprop-1-en-1-amine (0.11 mL, 0.84 mmol). The reaction mixture was stirred at rt for 10 min and treated with a solution of (R)-methyl 4-(((1-(2,3-difluorophenyl)ethyl)amino)methyl)benzoate (170 mg, 0.56 mmol) in DCM (1 mL) followed by DIEA (0.19 mL, 1.11 mmol). The resulting reaction mixture was stirred at rt for 0.5 h and concentrated in vacuo. The residue was purified by flash column chromatography (eluting with 10% EtOAc/DCM) to afford the title compound as a white solid (0.27 g, 81%). $^1$H NMR (CDCl$_3$) δ 8.15-7.85 (m, 1H), 7.79-7.66 (m, 2H), 7.54-7.31 (m, 5H), 7.26-6.75 (m, 8H), 5.83-5.44 (m, 1H), 5.38-4.81 (m, 4H), 4.73-4.24 (m, 3H), 3.94 (d, J=8.6 Hz, 1H), 3.89 (s, 2H), 3.38-2.72 (m, 2H), 2.05 (s, 1H), 1.69 (d, J=6.8 Hz, 1H), 1.55-1.43 (m, 1H); MS(ESI$^+$) m/z 599.3 (M+H)$^+$.

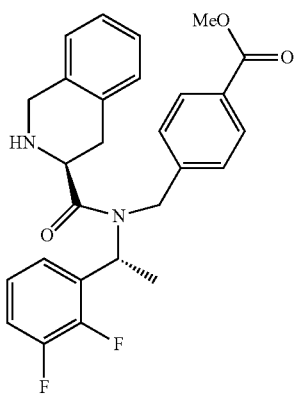 [SMILES: COC(=O)c1ccc(CN(C(=O)[C@@H]2Cc3ccccc3CN2)[C@H](C)c2cccc(F)c2F)cc1]

E) Methyl 4-(((S)-N-((R)-1-(2,3-difluorophenyl)ethyl)-1,2,3,4-tetrahydroisoquinoline-3-carboxamido)methyl)benzoate To a solution of (S)-benzyl 3-(((R)-1-(2,3-difluorophenyl)ethyl)(4-(methoxycarbonyl)benzyl)carbamoyl)-3,4-dihydroisoquinoline-2(1H)-carboxylate (270 mg, 0.45 mmol) in MeOH (8 mL) was added Pd—C (63 mg, 0.090 mmol). The reaction mixture was degassed under vacuum and stirred under H$_2$ balloon for 2 h. The reaction mixture was filtered through a CELITE® pad (MeOH). The filtrate was concentrated in vacuo to give the title compound as a white solid (205 mg, 98%). $^1$H NMR (DMSO-d$_6$) δ 7.83-7.65 (m, 1.5H), 7.39-6.96 (m, 9.5H), 5.95-5.63 (m, 0.5H), 4.91-4.62 (m, 1.5H), 4.40-3.99 (m, 3H), 3.82 (s, 3H), 3.17 (d, J=5.1 Hz, 2H), 3.07-2.88 (m, 1H), 1.73-1.45 (m, 3H); MS(ESI$^+$) m/z 465.3 (M+H)$^+$.

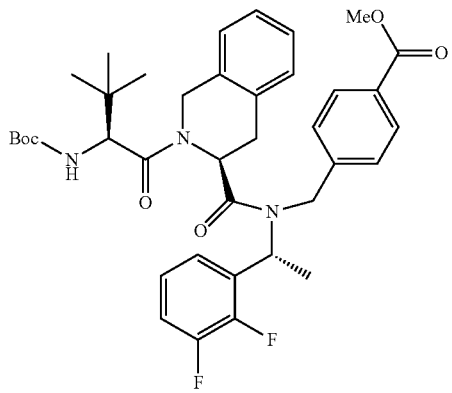 [SMILES: COC(=O)c1ccc(CN(C(=O)[C@@H]2Cc3ccccc3CN2C(=O)[C@@H](NC(=O)OC(C)(C)C)C(C)(C)C)[C@H](C)c2cccc(F)c2F)cc1]

F) Methyl 4-(((S)-2-((S)-2-((tert-butoxycarbonyl)amino)-3,3-dimethylbutanoyl)-N-((R)-1-(2,3-difluorophenyl)ethyl)-1,2,3,4-tetrahydroisoquinoline-3-carboxamido)methyl)benzoate To a solution of (S)-2-((tert-butoxycarbonyl)amino)-3,3-dimethylbutanoic acid (139 mg, 0.60 mmol) in DMF (2 mL) were added methyl 4-(((S)-N-((R)-1-(2,3-difluorophenyl)ethyl)-1,2,3,4-tetrahydroisoquinoline-3-carboxamido)methyl)benzoate (200 mg, 0.43 mmol), EDC (132 mg, 0.69 mmol), 3H-[1,2,3]-triazolo[4,5-b]pyridin-3-ol (59 mg, 0.43 mmol), a solution of DMF (2 mL) and 4-methylmorpholine (0.14 mL, 1.29 mmol). The reaction mixture was stirred at rt overnight and diluted with brine. The resulting mixture was extracted with ethyl acetate. The combined organic layers were separated and washed with saturated aq. NaHCO$_3$ solution and brine, successively. The organic layer was separated and dried over MgSO$_4$. The filtrate was concentrated in vacuo and the residue was purified by flash chromatography (eluting with 30% EtOAc/hexane) to afford the title compound as a white solid (0.24 g, 79%). $^1$H NMR (CDCl$_3$) δ 8.09 (d, J=8.1 Hz, 1H), 7.84 (d, J=8.1 Hz, 1H), 7.43 (d, J=8.1 Hz, 1H), 7.32-7.23 (m, 2H), 7.23-6.74 (m, 6H), 6.03-5.68 (m, 1H), 5.54-5.20 (m, 2H), 5.07-4.89 (m, 1H), 4.84-4.36 (m, 3H), 3.96-3.89 (m, 3H), 3.78-3.51 (m, 1H), 3.20-2.80 (m, 2H), 1.78-1.54 (m, 2H), 1.48-1.33 (m, 9H), 1.09 (d, J=14.3 Hz, 5H), 1.01-0.81 (m, 4H); MS(ESI$^+$) m/z 678.5 (M+H)$^+$.

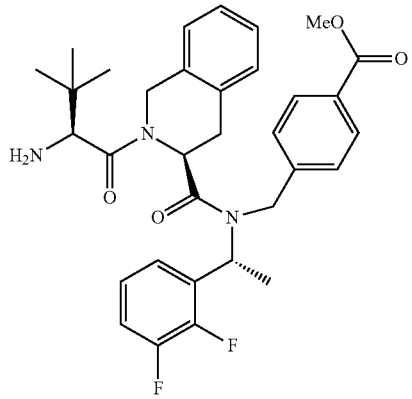 [SMILES: COC(=O)c1ccc(CN(C(=O)[C@@H]2Cc3ccccc3CN2C(=O)[C@@H](N)C(C)(C)C)[C@H](C)c2cccc(F)c2F)cc1]

G) Methyl 4-(((S)-2-((S)-2-amino-3,3-dimethylbutanoyl)-N-((R)-1-(2,3-difluorophenyl)ethyl)-1,2,3,4-tetrahydroisoquinoline-3-carboxamido)methyl)benzoate To a solution of methyl 4-(((S)-2-((S)-2-((tert-butoxycarbonyl)amino)-3,3-dimethylbutanoyl)-N-((R)-1-(2,3-difluorophenyl)ethyl)-1,2,3,4-tetrahydroisoquinoline-3-carboxamido)methyl)benzoate (235 mg, 0.35 mmol) in DCM (3 mL) was added TFA (0.70 mL, 9.09 mmol). The reaction mixture was stirred at rt for 1 h, concentrated in vacuo, and dried under vacuum overnight to give the title compound as a white solid (TFA salt, 235 mg, 96%). $^1$H NMR (DMSO-d$_6$) δ 7.91-7.69 (m, 2H), 7.58-7.25 (m, 6H), 7.24-6.93 (m, 3H), 5.89 (d, J=6.6 Hz, 0.5H), 5.27-4.84 (m, 1.5H), 4.68-4.35 (m, 3H), 4.26-4.13 (m, 0.5H), 3.89-3.77 (m, 3H), 3.70-3.43 (m, 0.5H), 3.13-2.77 (m, 1H), 1.70-1.45 (m, 2H), 1.14-1.02 (m, 9H), 1.00-0.93 (m, 3H); MS(ESI$^+$) m/z 578.4 (M+H)$^+$.

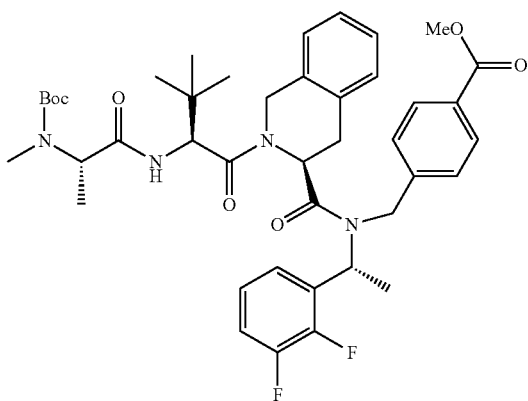 [SMILES: COC(=O)c1ccc(CN(C(=O)[C@@H]2Cc3ccccc3CN2C(=O)[C@@H](NC(=O)[C@H](C)N(C)C(=O)OC(C)(C)C)C(C)(C)C)[C@H](C)c2cccc(F)c2F)cc1]

H) Methyl 4-(((S)-2-((S)-2-((S)-2-((tert-butoxycarbonyl)(methyl)amino)propanamido)-3,3-dimethylbutanoyl)-N-((R)-1-(2,3-difluorophenyl)ethyl)-1,2,3,4-tetrahydroisoquinoline-3-carboxamido)methyl)benzoate To a solution of (S)-2-((tert-butoxycarbonyl)(methyl)amino)propanoic acid (90 mg, 0.44 mmol) in DMF (2 mL) were added EDC (104 mg, 0.54 mmol), 3H-[1,2,3]-triazolo[4,5-b]pyridin-3-ol (46 mg, 0.34 mmol), a solution of methyl 4-(((S)-2-((S)-2-amino-3,3-dimethylbutanoyl)-N-((R)-1-(2,3-difluorophenyl)ethyl)-1,2,3,4-tetrahydroisoquinoline-3-carboxamido)methyl)benzoate, TFA (235 mg, 0.34 mmol) in DMF (2 mL) and 4-methylmorpholine (0.22 mL, 2.04 mmol). The reaction mixture was stirred at rt for 1 h and diluted with ethyl acetate and brine. The organic layer was separated and washed with saturated aq. NaHCO₃ solution and brine, successively. The organic layer was separated and dried over MgSO₄. The filtrate was concentrated in vacuo and the residue was purified by flash column chromatography (eluting with 35% EtOAc/hexane) to afford the title compound as a white solid (0.18 g, 69%). ¹H NMR (CD₃OD) δ 8.07-7.72 (m, 2H), 7.53 (d, J=8.1 Hz, 0.5H), 7.38-6.99 (m, 8.5H), 5.91 (d, J=6.8 Hz, 1H), 5.19-4.91 (m, 3H), 4.76-4.53 (m, 4H), 3.97-3.79 (m, 3H), 3.17-2.63 (m, 5H), 1.79-1.56 (m, 3H), 1.53-1.28 (m, 13H), 1.15-0.94 (m, 9H); MS(ESI⁺) m/z 763.6 (M+H)⁺.

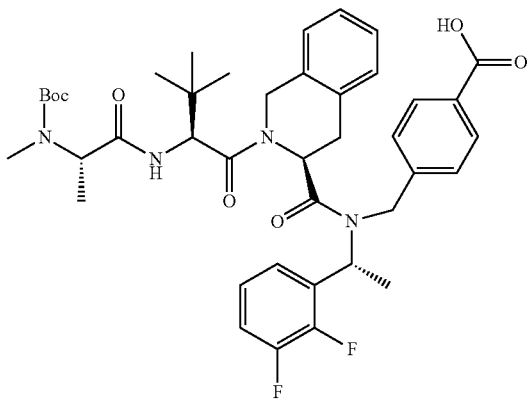 [SMILES: C[C@H](c1cccc(F)c1F)N(Cc1ccc(C(=O)O)cc1)C(=O)[C@@H]1Cc2ccccc2CN1C(=O)[C@@H](NC(=O)[C@H](C)N(C)C(=O)OC(C)(C)C)C(C)(C)C]

I) 4-(((S)-2-((S)-2-((S)-2-((tert-Butoxycarbonyl)(methyl)amino)propanamido)-3,3-dimethylbutanoyl)-N-((R)-1-(2,3-difluorophenyl)ethyl)-1,2,3,4-tetrahydroisoquinoline-3-carboxamido)methyl)benzoic acid To a solution of methyl 4-(((S)-2-((S)-2-((S)-2-((tert-butoxycarbonyl)(methyl)amino)propanamido)-3,3-dimethylbutanoyl)-N-((R)-1-(2,3-difluorophenyl)ethyl)-1,2,3,4-tetrahydroisoquinoline-3-carboxamido)methyl)benzoate (180 mg, 0.24 mmol) in THF (1 mL) and MeOH (1 mL) was added aq. LiOH solution (1 mL, 4.00 mmol). The reaction mixture was stirred at rt overnight and treated with 1 N HCl solution to adjust the pH of the solution to 1. The residue was extracted with ethyl acetate and the organic layer was separated and dried over MgSO₄. The filtrate was concentrated in vacuo to give the title compound as a white solid (175 mg, 99%). ¹H NMR (DMSO-d₆) δ 7.90 (d, J=8.1 Hz, 0.5H), 7.67 (d, J=8.4 Hz, 1.5H), 7.48-6.88 (m, 9H), 5.89-5.76 (m, 1H), 5.16-4.77 (m, 2H), 4.70-4.33 (m, 3H), 3.08-2.81 (m, 2H), 2.78-2.68 (m, 3H), 1.91 (s, 3H), 1.71-1.45 (m, 2H), 1.41 (br. s., 9H), 1.19-1.11 (m, 3H), 1.05-0.84 (m, 9H); MS(ESI⁺) m/z 749.5 (M+H)⁺.

J) (S)-N-((R)-1-(2,3-Difluorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-N-((R)-1-(2,3-difluorophenyl)ethyl)-1,2,3,4-tetrahydroisoquinoline-3-carboxamido)methyl)benzoic acid (70 mg, 0.093 mmol) in DMF (2 mL) were added HATU (57 mg, 0.15 mmol), followed by tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 57 mg, 0.10 mmol) and DIEA (0.03 mL, 0.19 mmol). The resulting reaction mixture was stirred at rt for 1 h and diluted with ethyl acetate and brine. The organic layer was separated and concentrated in vacuo. The residue was purified by preparative HPLC. Fractions containing the product were combined and concentrated in vacuo.

To a solution of the above product (45 mg, 0.035 mmol) in DCM (2 mL) was added TFA (0.5 mL, 6.49 mmol). The reaction mixture was stirred at rt for 1 h and concentrated in vacuo. The residue was lyophilized to give the title compound as a white solid (2 TFA salt, 38 mg, 30%). MS(ESI⁺) m/z 1088.7 (M+H)⁺.

Example 7

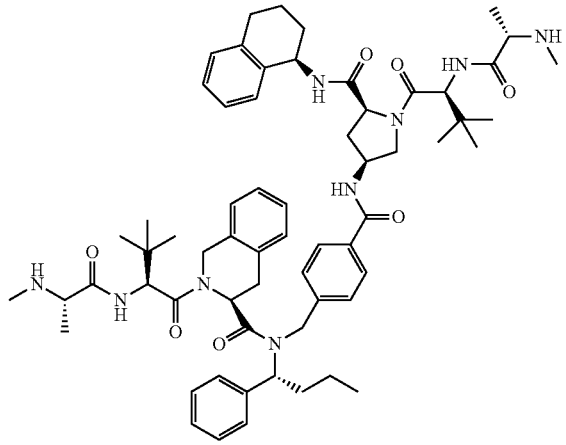

(S)-2-((S)-3,3-Dimethyl-2-((S)-2-(methylamino)
propanamido)butanoyl)-N-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)benzyl)-N-
((R)-1-phenylbutyl)-1,2,3,4-tetrahydroisoquinoline-
3-carboxamide

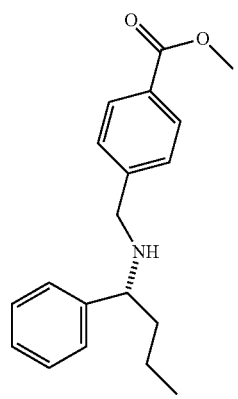 [SMILES: CCC[C@@H](NCc1ccc(C(=O)OC)cc1)c1ccccc1]

A) (R)-Methyl 4-(((1-phenylbutyl)amino)methyl)
benzoate

To a solution of (R)-1-phenylbutan-1-amine (287 mg, 1.92 mmol) in DMF (8 mL) were added methyl 4-(bromomethyl)benzoate (400 mg, 1.75 mmol) and $K_2CO_3$ (386 mg, 2.79 mmol). The reaction mixture was stirred at rt for 2 h and diluted with ethyl acetate and brine. The organic layer was separated, washed with brine and dried over $MgSO_4$. The filtrate was concentrated in vacuo to give the title compound as a colorless oil (0.52 g, 95%). $^1$H NMR (CDCl$_3$) δ 7.98 (d, J=8.4 Hz, 2H), 7.42-7.28 (m, 7H), 3.92 (s, 3H), 3.75-3.53 (m, 2H), 1.80-1.49 (m, 3H), 1.40-1.11 (m, 2H), 0.87 (t, J=7.4 Hz, 3H); MS(ESI$^+$) m/z 298.1 (M+H)$^+$.

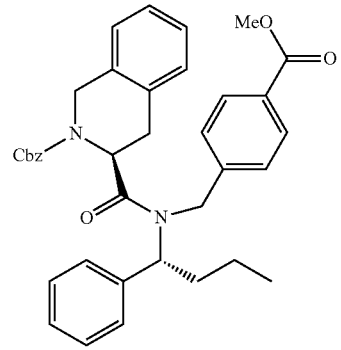 [SMILES: CCC[C@H](c1ccccc1)N(Cc1ccc(C(=O)OC)cc1)C(=O)[C@@H]1Cc2ccccc2CN1C(=O)OCc1ccccc1]

B) (S)-Benzyl 3-((4-(methoxycarbonyl)benzyl)((R)-
1-phenylbutyl)carbamoyl)-3,4-dihydroisoquinoline-2
(1H)-carboxylate To a solution of (S)-2-((benzyloxy)carbonyl)-1,2,3,4-tetrahydroisoquinoline-3-carboxylic acid (214 mg, 0.69 mmol) in DCM (4 mL) was added 1-chloro-N,N,2-trimethylprop-1-en-1-amine (0.11 mL, 0.86 mmol). The reaction mixture was stirred at rt for 10 min and treated with a solution of (R)-methyl 4-(((1-phenylbutyl)amino)methyl)benzoate (170 mg, 0.57 mmol) in DCM (1 mL) and DIEA (0.20 mL, 1.14 mmol). The resulting reaction mixture was stirred at rt for 0.5 h and diluted with DCM and brine. The organic layer was separated and dried over $MgSO_4$. The filtrate was concentrated in vacuo and the residue was purified by flash column chromatography (eluting with 40% EtOAc/hexane) to afford the title compound as a white solid (0.29 g, 85%). MS(ESI$^+$) m/z 591.6 (M+H)$^+$.

The intermediate acid 4-(((S)-2-((S)-2-((S)-2-((tert-Butoxycarbonyl)(methyl)amino)propanamido)-3,3-dimethylbutanoyl)-N-((R)-1-phenylbutyl)-1,2,3,4-tetrahydroisoquinoline-3-carboxamido)methyl)benzoic acid was prepared using similar chemistry outlined for Example 6.

C) (S)-2-((S)-3,3-Dimethyl-2-((S)-2-(methylamino)
propanamido)butanoyl)-N-(4-(((3S,5S)-1-((S)-3,3-
dimethyl-2-((S)-2-(methylamino)propanamido)bu-
tanoyl)-5-(((R)-1,2,3,4-tetrahydronaphthalen-1-yl)
carbamoyl)pyrrolidin-3-yl)carbamoyl)benzyl)-N-
((R)-1-phenylbutyl)-1,2,3,4-tetrahydroisoquinoline-
3-carboxamide To a solution of 4-(((S)-2-((S)-2-((S)-2-((tert-butoxycarbonyl)(methyl)amino)propanamido)-3,3-dimethylbutanoyl)-N-((R)-1-phenylbutyl)-1,2,3,4-tetrahydroisoquinoline-3-carboxamido)methyl)benzoic acid (74 mg, 0.10 mmol) in DMF (1.5 mL) were added HATU (70 mg, 0.20 mmol), followed by tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 61 mg, 0.11 mmol) and DIEA (0.04 mL, 0.20 mmol). The reaction mixture was stirred at rt for 1 h and diluted with ethyl acetate and brine. The organic layer was separated and concentrated in vacuo. The crude product was used directly in the next step without purification.

To a solution of the above crude product (80 mg, 0.062 mmol) in DCM (2.0 mL) was added TFA (0.4 mL, 5.19 mmol). The reaction mixture was stirred at rt for 1 h and concentrated in vacuo. The residue was purified by preparative HPLC. Fractions containing the desired product were combined, concentrated, and lyophilized to give the title compound as a white solid (2 TFA salt, 77 mg, 55%). MS(ESI$^+$) m/z 1080.6 (M+H)$^+$.

Example 8

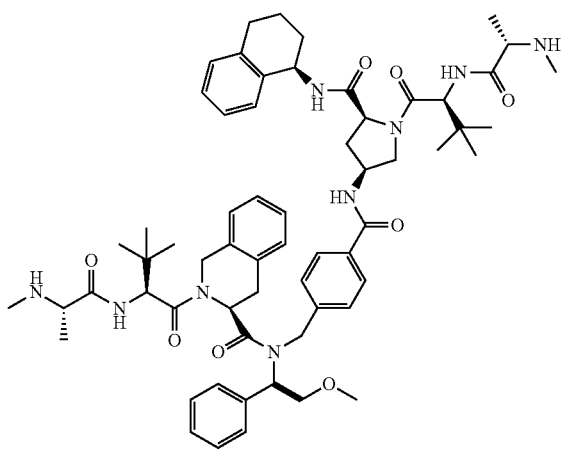

(S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-2-methoxy-1-phenylethyl)-1,2,3,4-tetrahydroisoquinoline-3-carboxamide

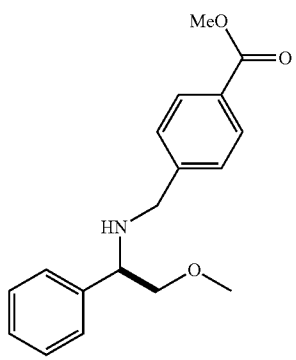 [SMILES: COC[C@H](NCc1ccc(C(=O)OC)cc1)c1ccccc1]

A) (R)-Methyl 4-(((2-methoxy-1-phenylethyl)amino)methyl)benzoate

To a solution of (R)-2-methoxy-1-phenylethanamine (311 mg, 2.06 mmol, source: Chem-Impex international) in DMF (8 mL) were added methyl 4-(bromomethyl)benzoate (410 mg, 1.79 mmol) and K$_2$CO$_3$ (396 mg, 2.86 mmol). The reaction mixture was stirred at rt for 2 h and diluted with ethyl acetate and brine. The organic layer was separated and washed with brine and dried over MgSO$_4$. The filtrate was concentrated in vacuo and the resulting residue was purified by flash column chromatography (eluting with 50% EtOAc/hexane) to afford the title compound as a colorless oil (0.42 g, 78%). $^1$H NMR (CDCl$_3$) δ 7.98 (d, J=8.4 Hz, 2H), 7.47-7.31 (m, 3H), 7.28-7.18 (m, 2H), 6.98 (td, J=7.4, 1.0 Hz, 1H), 6.90 (dd, J=8.3, 0.8 Hz, 1H), 4.20-4.07 (m, 1H), 3.92 (s, 3H), 3.83 (s, 3H), 3.77-3.59 (m, 2H), 1.73 (br. s., 1H), 1.39 (d, J=6.6 Hz, 2H); MS(ESI$^+$) m/z 300.1 (M+H)$^+$.

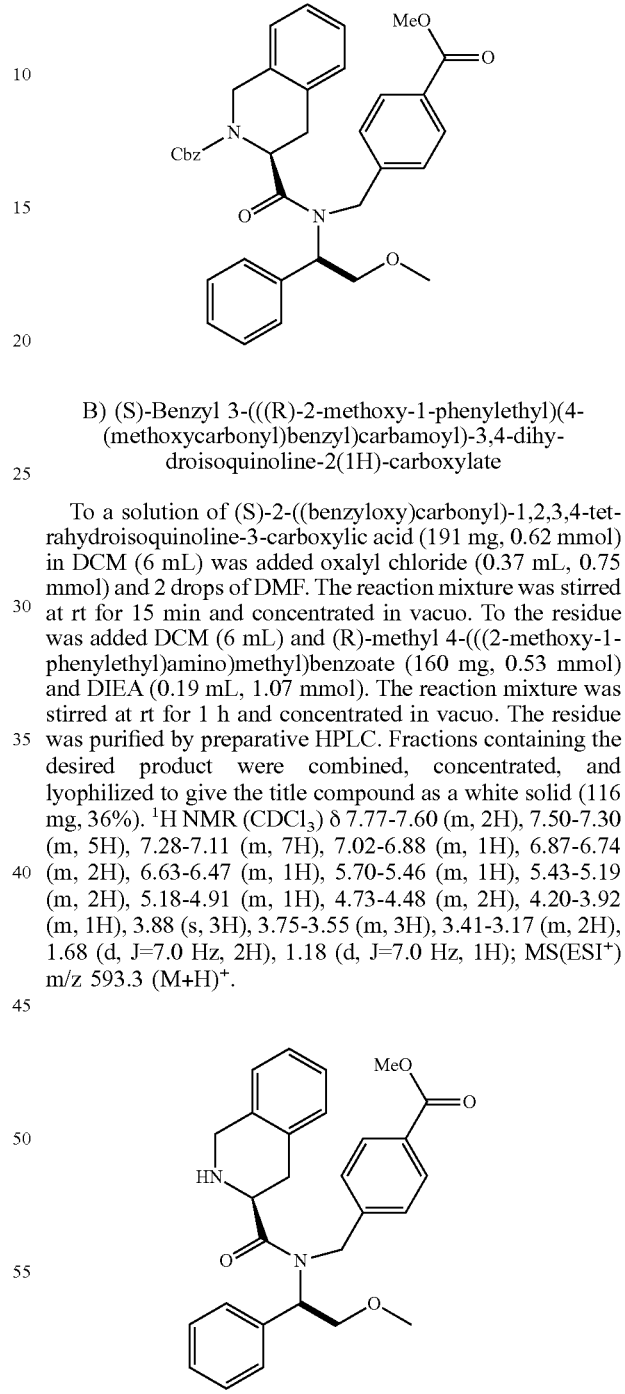

B) (S)-Benzyl 3-(((R)-2-methoxy-1-phenylethyl)(4-(methoxycarbonyl)benzyl)carbamoyl)-3,4-dihydroisoquinoline-2(1H)-carboxylate To a solution of (S)-2-((benzyloxy)carbonyl)-1,2,3,4-tetrahydroisoquinoline-3-carboxylic acid (191 mg, 0.62 mmol) in DCM (6 mL) was added oxalyl chloride (0.37 mL, 0.75 mmol) and 2 drops of DMF. The reaction mixture was stirred at rt for 15 min and concentrated in vacuo. To the residue was added DCM (6 mL) and (R)-methyl 4-(((2-methoxy-1-phenylethyl)amino)methyl)benzoate (160 mg, 0.53 mmol) and DIEA (0.19 mL, 1.07 mmol). The reaction mixture was stirred at rt for 1 h and concentrated in vacuo. The residue was purified by preparative HPLC. Fractions containing the desired product were combined, concentrated, and lyophilized to give the title compound as a white solid (116 mg, 36%). $^1$H NMR (CDCl$_3$) δ 7.77-7.60 (m, 2H), 7.50-7.30 (m, 5H), 7.28-7.11 (m, 7H), 7.02-6.88 (m, 1H), 6.87-6.74 (m, 2H), 6.63-6.47 (m, 1H), 5.70-5.46 (m, 1H), 5.43-5.19 (m, 2H), 5.18-4.91 (m, 1H), 4.73-4.48 (m, 2H), 4.20-3.92 (m, 1H), 3.88 (s, 3H), 3.75-3.55 (m, 3H), 3.41-3.17 (m, 2H), 1.68 (d, J=7.0 Hz, 2H), 1.18 (d, J=7.0 Hz, 1H); MS(ESI$^+$) m/z 593.3 (M+H)$^+$.

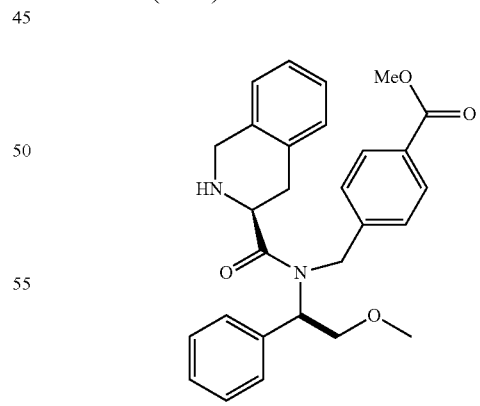

C) Methyl 4-(((S)-N-((R)-2-methoxy-1-phenylethyl)-1,2,3,4-tetrahydroisoquinoline-3-carboxamido)methyl)benzoate To a solution of (S)-benzyl 3-(((R)-2-methoxy-1-phenylethyl)(4-(methoxycarbonyl)benzyl)carbamoyl)- 3,4-dihydroisoquinoline-2(1H)-carboxylate (112 mg, 0.19 mmol) in MeOH (8 mL) was added Pd(OH)$_2$ on carbon (27 mg, 0.04 mmol). The reaction mixture was degassed under vacuum and stirred under H$_2$ balloon for 3 h. The reaction mixture was filtered through a CELITE® pad. The filtrate was concentrated in vacuo to give the title compound as a white solid (87 mg, 100%). $^1$H NMR (DMSO-d$_6$) δ 7.83-7.62 (m, 2H), 7.44-7.31 (m, 1H), 7.26-7.06 (m, 5H), 7.01-6.80 (m, 3H), 6.72 (d, J=8.1 Hz, 1H), 5.91-5.44 (m, 1H), 4.82-4.42 (m, 2H), 4.37-4.10 (m, 2H), 3.81 (s, 3H), 3.72-3.66 (m, 3H), 3.32 (br. s., 2H), 3.25-3.00 (m, 1H), 1.65-1.30 (m, 3H); MS(ESI$^+$) m/z 459.4 (M+H)$^+$.

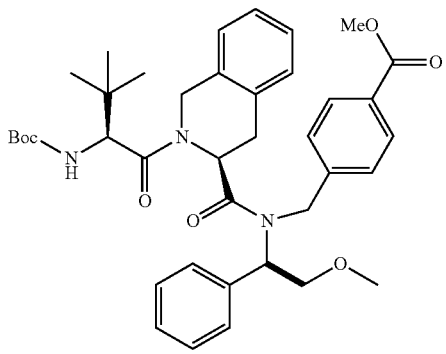 [SMILES: COC[C@@H](c1ccccc1)N(Cc1ccc(C(=O)OC)cc1)C(=O)[C@@H]1Cc2ccccc2CN1C(=O)[C@@H](NC(=O)OC(C)(C)C)C(C)(C)C]

D) Methyl 4-(((S)-2-((S)-2-((tert-butoxycarbonyl) amino)-3,3-dimethylbutanoyl)-N-((R)-2-methoxy-1-phenylethyl)-1,2,3,4-tetrahydroisoquinoline-3-carboxamido)methyl)benzoate To a solution of (S)-2-((tert-butoxycarbonyl)amino)-3,3-dimethylbutanoic acid (61 mg, 0.27 mmol) in DMF (1 mL) were added EDC (58 mg, 0.304 mmol) and 3H-[1,2,3]-triazolo[4,5-b]pyridin-3-ol (26 mg, 0.19 mmol), followed by addition of a solution of methyl 4-(((S)-N-((R)-2-methoxy-1-phenylethyl)-1,2,3,4-tetrahydroisoquinoline-3-carboxamido)methyl)benzoate (87 mg, 0.19 mmol) in DMF (2 mL) and 4-methylmorpholine (0.06 mL, 0.57 mmol). The reaction mixture was stirred at rt overnight and diluted with ethyl acetate and brine. The organic layer was separated and washed with saturated aq. NaHCO$_3$ solution and brine, successively. The organic layer was separated and dried over MgSO$_4$. The filtrate was concentrated in vacuo and the residue was purified by flash column chromatography (eluting with 35% EtOAc/hexane) to afford the title compound as a white solid (120 mg, 93%). MS(ESI$^+$) m/z 672.5 (M+H)$^+$.

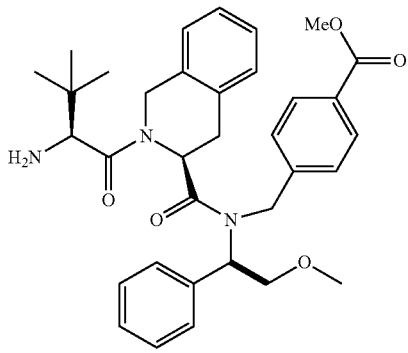 [SMILES: COC[C@@H](c1ccccc1)N(Cc1ccc(C(=O)OC)cc1)C(=O)[C@@H]1Cc2ccccc2CN1C(=O)[C@@H](N)C(C)(C)C]

E) Methyl 4-(((S)-2-((S)-2-amino-3,3-dimethylbutanoyl)-N-((R)-2-methoxy-1-phenylethyl)-1,2,3,4-tetrahydroisoquinoline-3-carboxamido)methyl)benzoate To a solution of methyl 4-(((S)-2-((S)-2-((tert-butoxycarbonyl)amino)-3,3-dimethylbutanoyl)-N-((R)-2-methoxy-1-phenylethyl)-1,2,3,4-tetrahydroisoquinoline-3-carboxamido)methyl)benzoate (120 mg, 0.18 mmol) in DCM (2 mL) was added TFA (0.7 mL, 9.09 mmol). The reaction mixture was stirred at rt for 1 h and concentrated in vacuo to give the title compound as a white solid, which was used directly in the next step reaction without purification. MS(ESI$^+$) m/z 572.5 (M+H)$^+$.

The intermediate acid 4-(((S)-2-((S)-2-((S)-2-((tert-butoxycarbonyl)(methyl)amino)propanamido)-3,3-dimethylbutanoyl)-N-((R)-2-methoxy-1-phenylethyl)-1,2,3,4-tetrahydroisoquinoline-3-carboxamido)methyl)benzoic acid was prepared using a similar procedure for Example 6, steps H and I.

F) (S)-2-((S)-3,3-Dimethyl-2-((S)-2-(methylamino) propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)carbamoyl)benzyl)-N-((R)-2-methoxy-1-phenylethyl)-1,2,3,4-tetrahydroisoquinoline-3-carboxamide To a solution of 4-(((S)-2-((S)-2-((S)-2-((tert-butoxycarbonyl)(methyl)amino)propanamido)-3,3-dimethylbutanoyl)-N-((R)-2-methoxy-1-phenylethyl)-1,2,3,4-tetrahydroisoquinoline-3-carboxamido)methyl)benzoic acid (8 mg, 10.77 μmol) in DMF (1 mL) were added HATU (5.32 mg, 0.014 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 7.2 mg, 0.013 mmol), followed by 4-methylmorpholine (4.7 μl, 0.043 mmol). The reaction mixture was stirred at rt for 1 h and diluted with ethyl acetate and brine. The organic layer was separated and washed with saturated aq. NaHCO$_3$ solution and 1 N HCl solution, successively. The organic layer was separated and dried over MgSO$_4$. The filtrate was concentrated in vacuo and the resulting residue was used directly in the next step without purification.

To the solution of the crude product 1 (10 mg, 7.8 μmol) in DCM (1 mL) was added TFA (0.17 mL, 2.2 mmol). The reaction mixture was stirred at rt for 40 min, treated with 0.3 mL of DIEA and concentrated in vacuo. The residue was purified by preparative HPLC. Fractions containing the product were combined, concentrated, and lyophilized to give the title compound as a white solid (2 TFA salt, 5 mg, 30%). MS(ESI$^+$) m/z 1083.8 (M+H)$^+$.

Example 9

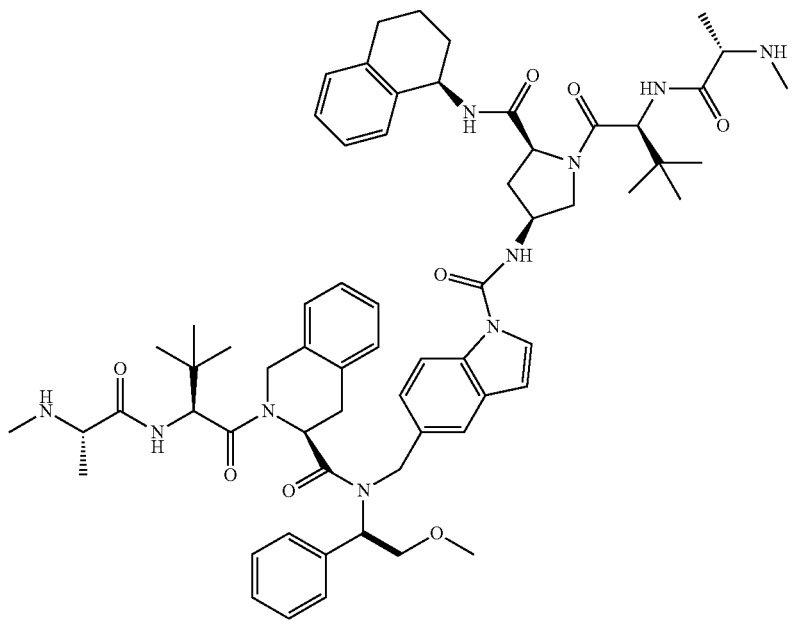

(S)-2-((S)-3,3-Dimethyl-2-((S)-2-(methylamino)propanamido)butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)-1H-indol-5-yl)methyl)-N-((S)-2-methoxy-1-phenylethyl)-1,2,3,4-tetrahydroisoquinoline-3-carboxamide matography (0-30% EtOAc/DCM gradient elution) to afford the title compound as a colorless oil (0.83 g, 83%). $^1$H NMR (CDCl$_3$) δ 8.13 (br. s., 1H), 7.55 (s, 1H), 7.50-7.44 (m, 2H), 7.43-7.28 (m, 4H), 7.23-7.18 (m, 1H), 7.15 (dd, J=8.4, 1.5 Hz, 1H), 6.53 (ddd, J=3.2, 2.1, 0.9 Hz, 1H), 4.01 (dd, J=7.2, 5.8 Hz, 1H), 3.82 (d, J=12.8 Hz, 1H), 3.64 (d, J=12.8 Hz, 1H), 3.46 (s, 1H), 3.45 (d, J=1.3 Hz, 1H), 3.32 (s, 3H); MS(ESI$^+$) m/z 281.1 (M+H)$^+$.

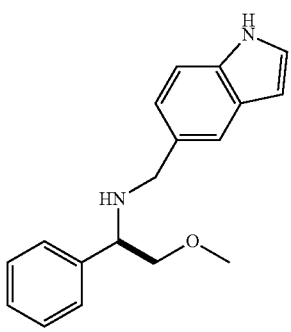 [SMILES: COC[C@H](NCc1ccc2[nH]ccc2c1)c1ccccc1]

A) (S)-N-((1H-Indol-5-yl)methyl)-2-methoxy-1-phenylethanamine

To a solution of (R)-2-methoxy-1-phenylethanamine (0.60 g, 3.9 mmol) in DCE (12 mL) was added 1H-indole-5-carbaldehyde (0.52 g, 3.6 mmol). The reaction mixture was stirred at rt for 10 min and treated with NaBH(OAc)$_3$ (1.22 g, 5.73 mmol). The resulting mixture was stirred at rt for 3 h and treated with saturated aq. NaHCO$_3$ solution. The mixture was stirred for 10 min and extracted with ethyl acetate. The organic layer was separated, washed with brine, and dried over MgSO$_4$. The filtrate was concentrated in vacuo and the residue was purified by flash column chro-

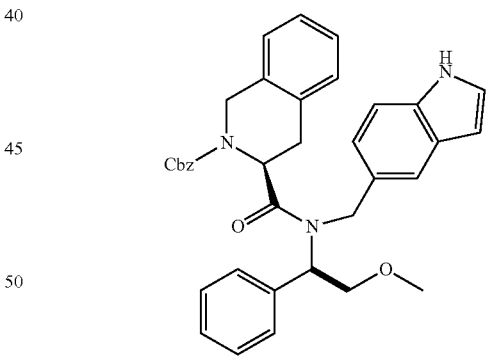

B) (S)-Benzyl 3-(((1H-indol-5-yl)methyl)((S)-2-methoxy-1-phenylethyl)carbamoyl)-3,4-dihydroisoquinoline-2(1H)-carboxylate To a solution of (S)-2-((benzyloxy)carbonyl)-1,2,3,4-tetrahydroisoquinoline-3-carboxylic acid (239 mg, 0.77 mmol) in DCM (8 mL) was added 1-chloro-N,N,2-trimethylprop-1-en-1-amine (0.1 mL, 0.77 mmol) under nitrogen. The reaction mixture was stirred at rt for 10 min and treated with a solution of (S)-N-((1H-indol-5-yl)methyl)-2-methoxy-1-phenylethanamine (205 mg, 0.73 mmol) in DCM (3 mL) followed by DIEA (0.26 mL, 1.46 mmol). The reaction mixture was stirred at rt for 20 min and diluted with brine and DCM. The organic layer was separated and washed with saturated aq. NaHCO₃ solution. The organic layer was separated and dried over MgSO₄. The filtrate was concentrated in vacuo and the residue was purified by flash column chromatography (0-25% EtOAc/DCM gradient elution) to afford the title compound as a colorless oil (405 mg, 97%). ¹H NMR (CDCl₃) δ 8.30-8.05 (m, 1H), 7.47-7.28 (m, 9H), 7.24-7.07 (m, 7H), 7.01-6.70 (m, 2H), 6.53-6.34 (m, 1H), 5.76-5.53 (m, 1.5H), 5.26-5.08 (m, 2.5H), 5.01-4.33 (m, 4H), 3.91-3.41 (m, 3H), 3.24 (d, J=6.6 Hz, 2H), 3.10-2.94 (m, 1H), 2.91-2.54 (m, 1H); MS(ESI⁺) m/z 574.3 (M+H)⁺.

fied by preparative HPLC. Fractions containing the product were combined, and concentrated to small amount. The residue was extracted with ethyl acetate and organic layer was separated and dried over MgSO₄. The filtrate was concentrated in vacuo to give the title compound as a white solid (200 mg, 50%). ¹H NMR (CDCl₃) δ 8.94-8.66 (m, 1H), 8.33-8.03 (m, 1H), 7.88-7.48 (m, 2H), 7.44-7.29 (m, 8H), 7.24-7.01 (m, 8H), 6.98-6.42 (m, 3H), 5.85-5.33 (m, 1H), 5.30-5.02 (m, 3H), 4.95-4.29 (m, 13H), 4.18-3.40 (m, 5H), 3.36-3.15 (m, 2H), 3.10-2.91 (m, 1.5H), 2.88-2.68 (m, 3.5H), 2.66-2.29 (m, 2H), 2.24-1.98 (m, 2H), 1.90 (d, J=9.5 Hz, 3H), 1.48 (s, 6H), 1.39-1.20 (m, 3H), 0.96-0.66 (m, 9H); MS(ESI⁺) m/z 1157.6 (M+H)⁺.

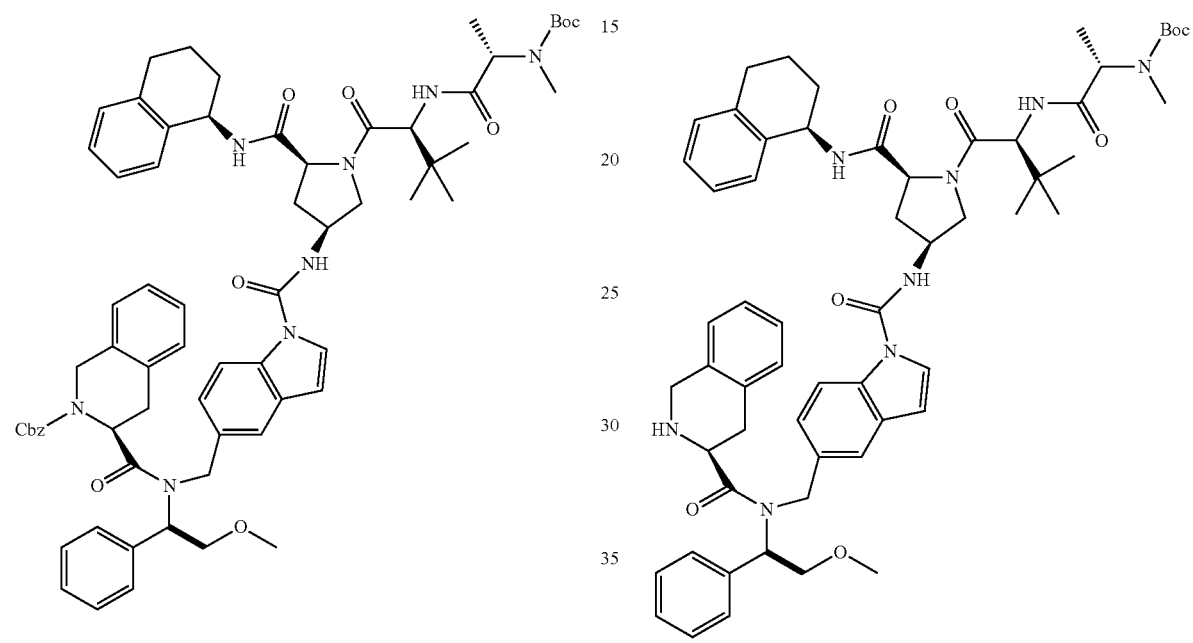

C) (S)-Benzyl 3-(((1-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)-1H-indol-5-yl)methyl)((S)-2-methoxy-1-phenylethyl)carbamoyl)-3,4-dihydroisoquinoline-2(1H)-carboxylate To a suspension of NaH (84 mg, 2.1 mmol) in DMF (5 mL) were added (S)-benzyl 3-(((1H-indol-5-yl)methyl)((S)-2-methoxy-1-phenylethyl)carbamoyl)-3,4-dihydroisoquinoline-2(1H)-carboxylate (200 mg, 0.35 mmol) at rt under nitrogen. The reaction mixture was stirred at rt for 1.5 h.

In a separate flask, a solution of 4-nitrophenyl carbonochloridate (246 mg, 1.22 mmol) in DCM (6 mL) was treated with a solution of tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 214 mg, 0.38 mmol) in DCM (3 mL) and DIEA (0.18 mL, 1.05 mmol) under nitrogen. The reaction mixture was stirred at rt for 30 min, and the added to the sodium salt described in the initial paragraph, followed by the addition of DIEA (0.18 mL, 1.05 mmol). The resulting reaction mixture was stirred at rt for 45 min and treated with MeOH (3 mL). The mixture was stirred for 5 min and diluted with brine solution and ethyl acetate. The organic layer was separated and concentrated in vacuo. The residue was puri- D) tert-Butyl ((S)-1-(((S)-1-((2S,4S)-4-(5-(((S)-N-((R)-2-methoxy-1-phenylethyl)-1,2,3,4-tetrahydroisoquinoline-3-carboxamido)methyl)-1H-indole-1-carboxamido)-2-(((S)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of (S)-benzyl 3-(((1-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)-1H-indol-5-yl)methyl)((S)-2-methoxy-1-phenylethyl)carbamoyl)-3,4-dihydroisoquinoline-2(1H)-carboxylate (190 mg, 0.16 mmol) in MeOH (8 mL) was added Pd(OH)₂ on carbon (35 mg, 0.05 mmol). The reaction mixture was degassed under vacuum and stirred under H₂ balloon for 1 h. The reaction mixture was filtered through a CELITE® pad (MeOH). The filtrate was combined and concentrated in vacuo to give the title compound as a white solid (165 mg, 98%). ¹H NMR (DMSO-d₆) δ 8.76-8.51 (m, 2H), 8.18-7.90 (m, 1H), 7.70 (dd, J=11.9, 3.5 Hz, 1H), 7.48-7.19 (m, 7H), 7.16-6.78 (m, 8H), 6.61-6.47 (m, 1H), 5.74-5.57 (m, 1H), 5.08-4.82 (m, 1H), 4.72-4.31 (m, 5.5H), 4.13-4.00 (m, 3.5H), 3.94-3.77 (m, 2.5H), 3.76-3.60 (m, 1.5H), 3.25-3.06 (m, 7H), 2.81-2.68 (m, 5H), 2.06-1.54 (m, 5H), 1.41 (s, 9H), 1.22 (d, J=6.8 Hz, 3H), 0.97 (br. s., 9H); MS(ESI⁺) m/z 1023.5 (M+H)⁺.

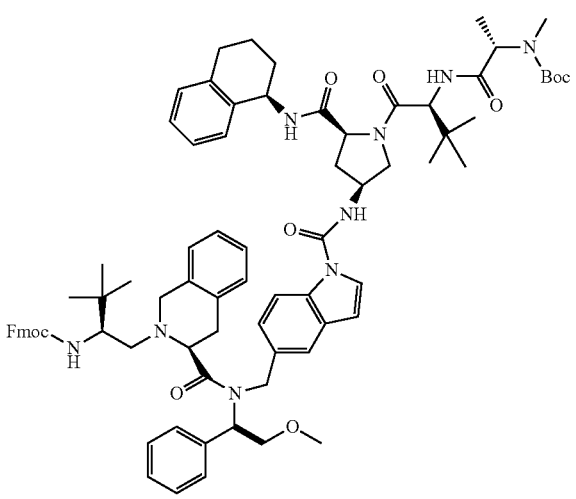

E) tert-Butyl ((S)-1-(((S)-1-((2S,4S)-4-(5-(((S)-2-((S)-2-(((((9H-fluoren-9-yl)methoxy)carbonyl)amino)-3,3-dimethylbutanoyl)-N-((S)-2-methoxy-1-phenylethyl)-1,2,3,4-tetrahydroisoquinoline-3-carboxamido)methyl)-1H-indole-1-carboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of (S)-2-(((((9H-fluoren-9-yl)methoxy)carbonyl)amino)-3,3-dimethylbutanoic acid (48 mg, 0.14 mmol) in DMF (2.5 mL) were added HATU (60 mg, 0.16 mmol), followed by addition of a solution of tert-butyl ((S)-1-(((S)-1-((2S,4S)-4-(5-(((S)-N-((S)-2-methoxy-1-phenylethyl)-1,2,3,4-tetrahydroisoquinoline-3-carboxamido)methyl)-1H-indole-1-carboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (100 mg, 0.098 mmol) in DMF (2.5 mL) and DIEA (0.05 mL, 0.29 mmol). The resulting reaction mixture was stirred at rt overnight and diluted with ethyl acetate and brine. The organic layer was separated, washed with saturated aq. NaHCO$_3$ solution and dried over MgSO$_4$. The filtrate was concentrated in vacuo and used directly in the next step without purification. MS(ESI$^+$) m/z 1375.8 (M+18)$^+$.

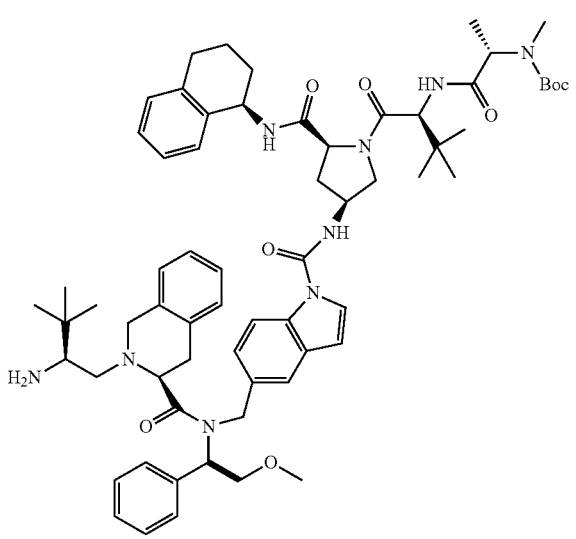 [SMILES: COC[C@@H](c1ccccc1)N(Cc1ccc2c(ccn2C(=O)N[C@H]2C[C@@H](C(=O)N[C@@H]3CCCc4ccccc43)N(C(=O)[C@@H](NC(=O)[C@H](C)N(C)C(=O)OC(C)(C)C)C(C)(C)C)C2)c1)C(=O)[C@@H]1Cc2ccccc2CN1C[C@@H](N)C(C)(C)C]

F) tert-Butyl ((S)-1-(((S)-1-((2S,4S)-4-(5-(((S)-2-((S)-2-amino-3,3-dimethylbutanoyl)-N-((S)-2-methoxy-1-phenylethyl)-1,2,3,4-tetrahydroisoquinoline-3-carboxamido)methyl)-1H-indole-1-carboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of crude tert-butyl ((5)-1-(((S)-1-((2S,4S)-4-(5-(((S)-2-((S)-2-(((((9H-fluoren-9-yl)methoxy)carbonyl)amino)-3,3-dimethylbutanoyl)-N-((S)-2-methoxy-1-phenylethyl)-1,2,3,4-tetrahydroisoquinoline-3-carboxamido)methyl)-1H-indole-1-carboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (100 mg, 0.074 mmol) in DCM (2.5 mL) was added piperidine (0.5 mL, 0.074 mmol). The reaction mixture was stirred at rt for 15 min and concentrated in vacuo. The residue was dissolved in MeOH and filtered. The filtrate was purified by preparative HPLC. Fractions containing the product were combined, concentrated, and lyophilized to give the title compound as a white solid (TFA salt, 50 mg, 48%). $^1$H NMR (DMSO-d$_6$) δ 8.79-8.54 (m, 2H), 8.20-7.92 (m, 3H), 7.85-7.50 (m, 3H), 7.47-6.82 (m, 14H), 6.68-6.37 (m, 1H), 5.72-5.34 (m, 1H), 5.21-4.92 (m, 2H), 4.87-4.33 (m, 8H), 4.14-3.62 (m, 6H), 3.29-3.14 (m, 3.5H), 2.86-2.61 (m, 5.5H), 2.39-2.23 (m, 1H), 2.05-1.52 (m, 5H), 1.41 (s, 9H), 1.22 (d, J=6.6 Hz, 3H), 1.11 (d, J=10.8 Hz, 9H), 0.97 (d, J=3.7 Hz, 9H); MS(ESI$^+$) m/z 1136.6 (M+H)$^+$.

G) (S)-2-((S)-3,3-Dimethyl-2-((S)-2-(methylamino)propanamido)butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)-1H-indol-5-yl)methyl)-N-((S)-2-methoxy-1-phenylethyl)-1,2,3,4-tetrahydroisoquinoline-3-carboxamide(S)-2-((S)-3,3-dimethyl-2-((S)-2-(methylamino)propanamido)butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)-1H-indol-5-yl)methyl)-N-((R)-2-methoxy-1-phenylethyl)-1,2,3,4-tetrahydroisoquinoline-3-carboxamide To a solution of (S)-2-((tert-butoxycarbonyl)(methyl)amino)propanoic acid (11 mg, 0.055 mmol) in DMF (1.5 mL) were added EDC (13 mg, 0.068 mmol), 3H-[1,2,3]-triazolo[4,5-b]pyridin-3-ol (7 mg, 0.051 mmol), a solution of tert-butyl 45)-1-(((S)-1-((2S,4S)-4-(5-(((S)-2-((S)-2-amino-3,3-dimethylbutanoyl)-N-((S)-2-methoxy-1-phenylethyl)-1,2,3,4-tetrahydroisoquinoline-3-carboxamido)methyl)-1H-indole-1-carboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (48 mg, 0.042 mmol) in DMF (2 mL) and DIEA (0.02 mL, 0.13 mmol). The reaction mixture was stirred at rt for 1 h and diluted with ethyl acetate and brine. The organic layer was separated and washed with saturated aq. NaHCO$_3$ solution and dried over MgSO$_4$. The filtrate was concentrated in vacuo and the resulting residue was used directly in the next step without purification.

To a solution of the crude product (40 mg, 0.030 mmol) in DCM (2 mL) was added TFA (0.7 mL, 9.1 mmol). The reaction mixture was stirred at rt for 50 min and concentrated in vacuo. The residue was dissolved in MeOH and purified by preparative HPLC. Fractions containing the product were combined, concentrated, and lyophilized to give the title compound as a white solid (2 TFA salt, 16 mg, 38%). MS(ESI$^+$) m/z 1121.6 (M+H)$^+$.

Example 10

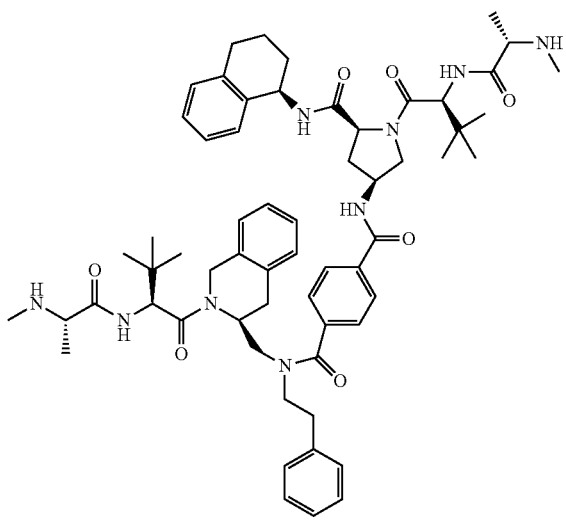

N$^1$-(((S)-2-((S)-3,3-Dimethyl-2-((S)-2-(methyl-amino)propanamido)butanoyl)-1,2,3,4-tetrahydroiso-quinolin-3-yl)methyl)-N$^4$-((3S,5S)-1-((S)-3,3-dim-ethyl-2-((S)-2-(methylamino)propanamido)butanoyl)-5-(((R)-1,2,3,4-tetrahydronaphthalen-1-yl)carbamoyl)pyrrolidin-3-yl)-N$^1$-phenethylterephthalamide

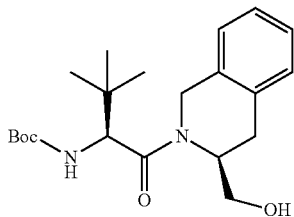 [SMILES: CC(C)(C)OC(=O)N[C@H](C(=O)N1Cc2ccccc2C[C@H]1CO)C(C)(C)C]

A) tert-Butyl ((S)-1-((S)-3-(hydroxymethyl)-3,4-dihydroisoquinolin-2(1H)-yl)-3,3-dimethyl-1-oxobutan-2-yl)carbamate To a solution of (S)-2-(tert-butoxycarbonylamino)-3,3-dimethylbutanoic acid (0.63 g, 2.70 mmol) in DMF (8 mL) were added EDC (0.61 g, 3.16 mmol) and 3H-[1,2,3]-triazolo[4,5-b]pyridin-3-ol (0.34 g, 2.48 mmol). The reaction mixture was stirred at rt for 5 min, followed by addition of 4-methylmorpholine (0.74 mL, 6.76 mmol) and a solution of (S)-(1,2,3,4-tetrahydroisoquinolin-3-yl)methanol, HCl (0.45 g, 2.25 mmol, *Bioorg. Med. Chem. Lett.*, 13:1585-1589 (2003)) in DMF (4 mL). The resulting reaction mixture was stirred at rt for 2 h and diluted with ethyl acetate and brine. The organic layer was separated and washed with citric acid solution, brine and saturated aq. NaHCO$_3$ solution. The organic layer was dried over MgSO$_4$ and filtered. The filtrate was concentrated in vacuo and the residue was purified by flash column chromatography (eluting with 15% EtOAc/DCM) to afford the title compound as a white solid (0.54 g, 64%). $^1$H NMR (CDCl$_3$) δ 7.25-7.06 (m, 4H), 5.44-5.34 (d, J=9.9 Hz, 1H), 5.14 (d, J=18.3 Hz, 0.5H), 4.99-4.89 (m, 0.5H), 4.67 (d, J=9.9 Hz, 1H), 4.60-4.44 (m, 0.5H), 4.31 (d, J=18.3 Hz, 0.5H), 3.73-3.39 (m, 2H), 3.31-3.10 (m, 1.5H), 2.75 (d, J=16.5 Hz, 0.5H), 1.48-1.38 (m, 9H), 1.10-0.96 (m, 9H); MS(ESI$^+$) m/z 377.3 (M+H)$^+$.

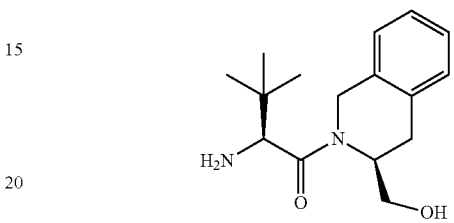

B) (S)-2-Amino-1-((S)-3-(hydroxymethyl)-3,4-dihydroisoquinolin-2(1H)-yl)-3,3-dimethylbutan-1-one To a solution of tert-butyl (S)-1-((S)-3-(hydroxymethyl)-3,4-dihydroisoquinolin-2(1H)-yl)-3,3-dimethyl-1-oxobutan-2-ylcarbamate (0.54 g, 1.4 mmol) in DCM (8 mL) was added HCl (4.0 M solution in dioxane, 5.4 mL, 22 mmol). The reaction mixture was stirred at rt for 2 h and concentrated in vacuo to give the title compound as a white solid (0.45 g, 99%), which was used directly in the next step. MS(ESI$^+$) m/z 277.2 (M+H)$^+$.

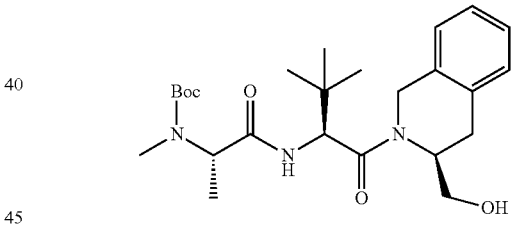

C) tert-Butyl ((S)-1-(((S)-1-((S)-3-(hydroxymethyl)-3,4-dihydroisoquinolin-2(1H)-yl)-3,3-dimethyl-1-oxobutan-2-yl)amino)-1-oxopropan-2-yl)(methyl)carbamate To a solution of (S)-2-(tert-butoxycarbonyl(methyl)amino)propanoic acid (0.38 g, 1.87 mmol) in DMF (10 mL) were added EDC (394 mg, 2.00 mmol) and 3H-[1,2,3]-triazolo[4,5-b]pyridin-3-ol (0.22 g, 1.58 mmol). The reaction mixture was stirred at rt for 5 min, and treated with 4-methylmorpholine (0.40 mL, 3.60 mmol) and a solution of (S)-2-amino-1-((S)-3-(hydroxymethyl)-3,4-dihydroisoquinolin-2(1H)-yl)-3,3-dimethylbutan-1-one, HCl (0.45 g, 1.44 mmol) in DMF (4 mL). The resulting reaction mixture was stirred at rt for 1 h and diluted with ethyl acetate and brine. The organic layer was separated, washed with citric acid solution, brine and saturated aq. NaHCO$_3$ solution. The organic layer was dried over MgSO$_4$ and the filtrate was concentrated in vacuo. The residue was purified by flash column chromatography (eluting with 25% EtOAc/hexane)

to afford the title compound as a white solid (0.52 g, 78%). $^1$H NMR (CDCl$_3$) δ 7.23-7.08 (m, 4H), 5.14-4.85 (m, 2H), 4.75-4.52 (m, 1H), 4.29 (d, J=18.3 Hz, 1H), 3.63-3.38 (m, 2H), 3.20-3.08 (m, 1H), 2.82-2.73 (m, 4H), 1.53-1.46 (m, 10H), 1.31 (d, J=7.0 Hz, 3H), 1.05-0.93 (m, 10H); MS(ESI$^+$) m/z 462.4 (M+H)$^+$.

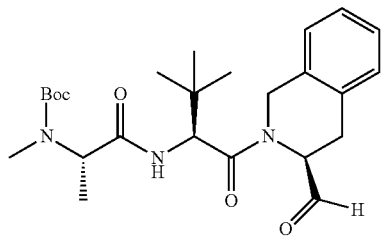 [SMILES: C[C@@H](C(=O)N[C@H](C(=O)N1Cc2ccccc2C[C@H]1C=O)C(C)(C)C)N(C)C(=O)OC(C)(C)C]

D) tert-Butyl ((S)-1-(((S)-1-((S)-3-formyl-3,4-dihydroisoquinolin-2(1H)-yl)-3,3-dimethyl-1-oxobutan-2-yl)amino)-1-oxopropan-2-yl)(methyl)carbamate To a solution of tert-butyl (S)-1-((5)-1-((5)-3-(hydroxymethyl)-3,4-dihydroisoquinolin-2(1H)-yl)-3,3-dimethyl-1-oxobutan-2-ylamino)-1-oxopropan-2-yl(methyl)carbamate (0.52 g, 1.13 mmol) in DCE (8 mL) was added Dess-Martin Periodinane (1.20 g, 2.82 mmol). The reaction mixture was stirred at rt for 4 h and diluted with saturated aq. NaHCO$_3$ solution. The resulting mixture was extracted with DCM. The organic layer was separated, washed with brine, NaS$_2$O$_3$ solution, and dried over MgSO$_4$. The filtrate was concentrated in vacuo and the residue was used directly without purification. MS(ESI$^+$) m/z 460.4 (M+H)$^+$.

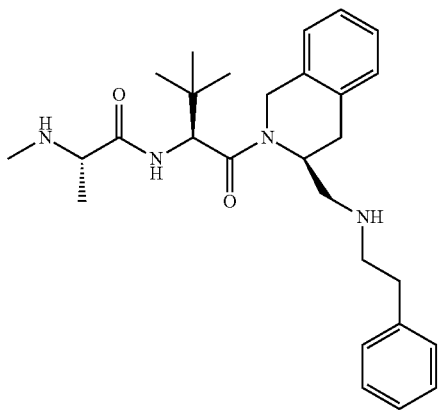 [SMILES: CN[C@@H](C)C(=O)N[C@H](C(=O)N1Cc2ccccc2C[C@H]1CNCCc1ccccc1)C(C)(C)C]

E) tert-Butyl ((S)-1-(((S)-3,3-dimethyl-1-oxo-1-((S)-3-((phenethylamino)methyl)-3,4-dihydroisoquinolin-2(1H)-yl)butan-2-yl)amino)-1-oxopropan-2-yl)(methyl)carbamate To a solution of tert-butyl (S)-1-((S)-1-((S)-3-formyl-3,4-dihydroisoquinolin- 2(1H)-yl)-3,3-dimethyl-1-oxobutan-2-ylamino)-1-oxopropan-2-yl(methyl)carbamate (130 mg, 0.28 mmol) in DCE (4 mL) was added 2-phenylethanamine (0.11 mL, 0.85 mmol). The reaction mixture was stirred at rt for 20 min and treated with NaBH(OAc)$_3$ (90 mg, 0.42 mmol). The resulting mixture was stirred at rt for 2 h and diluted with saturated aq. NaHCO$_3$ solution and ethyl acetate. The organic layer was separated, washed with brine, and dried over MgSO$_4$. The filtrate was concentrated in vacuo and the resulting residue was purified by preparative HPLC. Fractions containing the desired product were combined, concentrated, and lyophilized to give the title compound as a white solid (TFA salt, 36 mg, 19%). MS(ESI$^+$) m/z 565. 5 (M+H)$^+$.

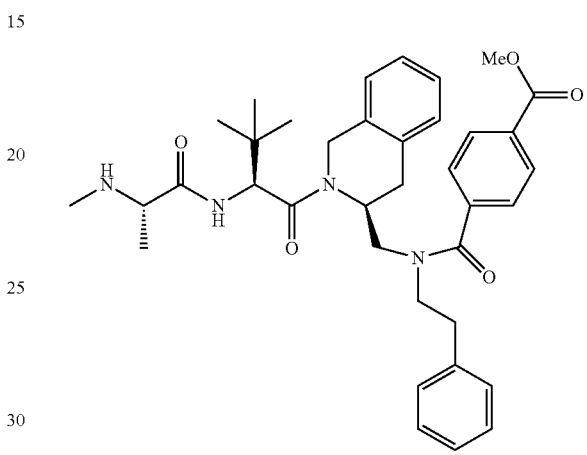

F) Methyl 4-((((S)-2-((S)-2-((S)-2-((tert-butoxycarbonyl)(methyl)amino)propanamido)-3,3-dimethylbutanoyl)-1,2,3,4-tetrahydroisoquinolin-3-yl)methyl)(phenethyl)carbamoyl)benzoate To a suspension of 4-(methoxycarbonyl)benzoic acid (19 mg, 0.10 mmol) in DCE (1 mL) was added oxalyl chloride (0.08 mL, 0.16 mmol) and 1 drop of DMF. The reaction mixture turned to a clear solution. After 30 min, the reaction mixture was concentrated in vacuo. The residue was dissolved in DCM (1 mL) and treated with tert-butyl (S)-1-((S)-3,3-dimethyl-1-oxo-1-((S)-3-((phenethylamino)methyl)-3,4-dihydroisoquinolin-2(1H)-yl)butan-2-ylamino)-1-oxopropan-2-yl(methyl)carbamate, TFA (35 mg, 0.052 mmol) and 4-methylmorpholine (0.02 mL, 0.21 mmol). The reaction mixture was stirred at rt for 1 h and concentrated in vacuo. The residue was dissolved in MeOH and purified by preparative HPLC. Fractions containing the product were combined, concentrated, and lyophilized to give the title compound as a white solid (13 mg, 35%). $^1$H NMR (CDCl$_3$) δ 8.00 (d, J=7.7 Hz, 1H), 7.91-7.78 (m, 1H), 7.25-7.11 (m, 8H), 6.95-6.65 (m, 3H), 5.24-4.89 (m, 2H), 4.81-4.46 (m, 2H), 3.95 (s, 3H), 3.73-3.46 (m, 2H), 3.22-2.44 (m, 9H), 1.60-1.45 (m, 9H), 1.37-1.19 (m, 3H), 1.09-0.87 (m, 10H); MS(ESI$^+$) m/z 727.7 (M+H)$^+$.

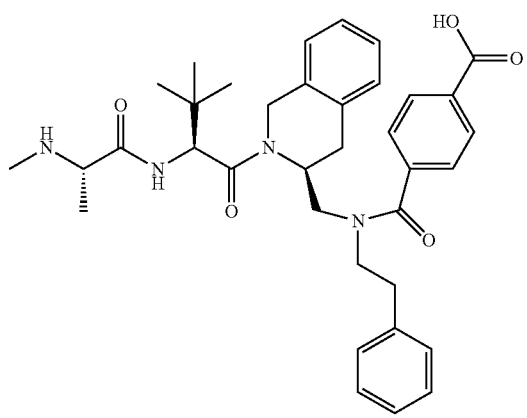 [SMILES: CN[C@@H](C)C(=O)N[C@H](C(=O)N1Cc2ccccc2C[C@H]1CN(CCc1ccccc1)C(=O)c1ccc(C(=O)O)cc1)C(C)(C)C]

G) 4-(((((S)-2-((S)-2-((S)-2-((tert-Butoxycarbonyl)(methyl)amino)propanamido)-3,3-dimethylbutanoyl)-1,2,3,4-tetrahydroisoquinolin-3-yl)methyl)(phenethyl)carbamoyl)benzoic acid To a solution of methyl 4-(((((S)-2-((S)-2-((S)-2-((tert-butoxycarbonyl)(methyl)amino)propanamido)-3,3-dimethylbutanoyl)-1,2,3,4-tetrahydroisoquinolin-3-yl)methyl)(phenethyl)carbamoyl)benzoate (13 mg, 0.018 mmol) in MeOH (1 mL) and THF (1 mL) was added aqueous NaOH solution (0.1 mL, 0.18 mmol). The reaction mixture was stirred at rt for 3 h and treated with 1 N HCl to adjust the pH of the solution to 1. The resulting mixture was extracted with ethyl acetate. The organic layer was separated and dried over MgSO4. The filtrate was concentrated in vacuo to give the title compound as a white solid (9 mg, 71%), which was used directly in the next step. MS(ESI$^+$) m/z 713.6 (M+H)$^+$.

H) N$^1$-(((S)-2-((S)-3,3-Dimethyl-2-((S)-2-(methylamino)propanamido)butanoyl)-1,2,3,4-tetrahydroisoquinolin-3-yl)methyl)-N$^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-N$^1$-phenethylterephthalamide To a solution of 4-(((((S)-2-((S)-2-((S)-2-((tert-butoxycarbonyl)(methyl)amino)propanamido)-3,3-dimethylbutanoyl)-1,2,3,4-tetrahydroisoquinolin-3-yl)methyl)(phenethyl)carbamoyl)benzoic acid (9 mg, 0.013 mmol) in DMF (1 mL) was added HATU (7.7 mg, 0.020 mmol), tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 9 mg, 0.014 mmol) and 4-methylmorpholine (10 μL, 0.08 mmol). The reaction mixture was stirred at rt for 1 h and concentrated in vacuo. The residue was purified by preparative HPLC. Fractions containing the product were combined, concentrated, and lyophilized to give a white solid.

To a solution of the obtained crude product (11 mg, 8.78 μmol) in DCM (1 mL) was added HCl (4 M solution in dioxane, 0.04 mL, 0.18 mmol). The reaction mixture was stirred at rt for 2 h and concentrated in vacuo. The residue was purified by preparative HPLC. Fractions containing the product were combined, concentrated, and lyophilized to give the title compound as a white solid (2 TFA salt, 6 mg, 35%). MS(ESI$^+$) m/z 1052.7 (M+H)$^+$.

Examples 11 to 37

The following Examples were prepared according to the procedures used for the synthesis of the Examples described above.

| Ex. No. | Structure | Name | LCMS (M + H) |
|---|---|---|---|
| 11 | 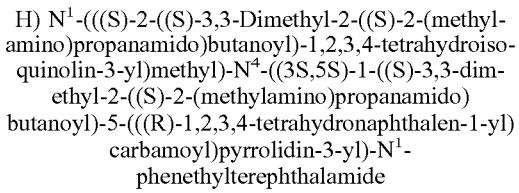 | (S)-N-(2,3-Dichlorobenzyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide | 1108.6 |

| Ex. No. | Structure | Name | LCMS (M + H) |
|---|---|---|---|
| 12 | 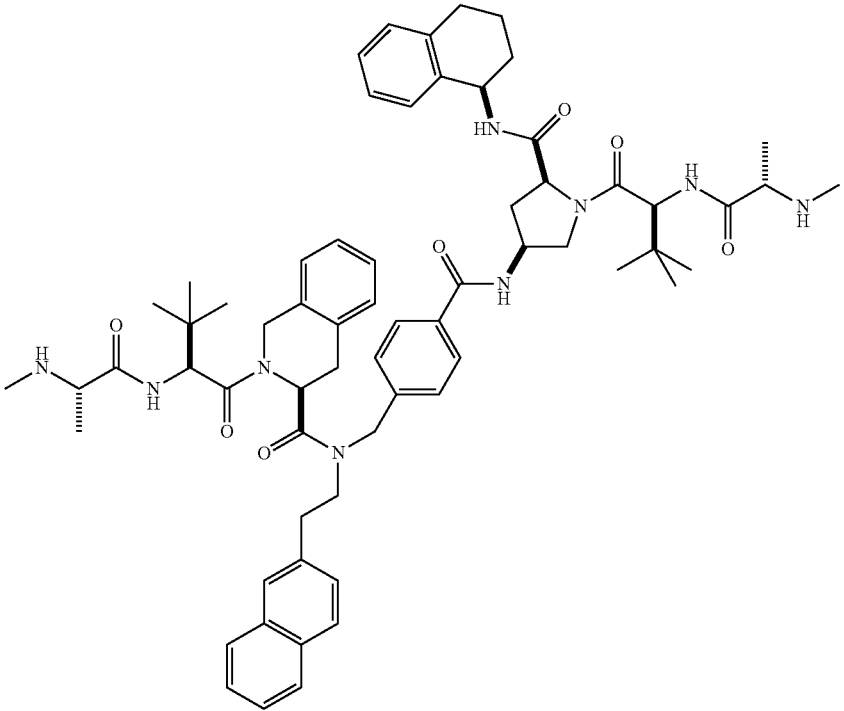 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-(2-(naphthalen-2-yl)ethyl)-1,2,3,4-tetrahydroisoquinoline-3-carboxamide | 1102.8 |
| 13 | 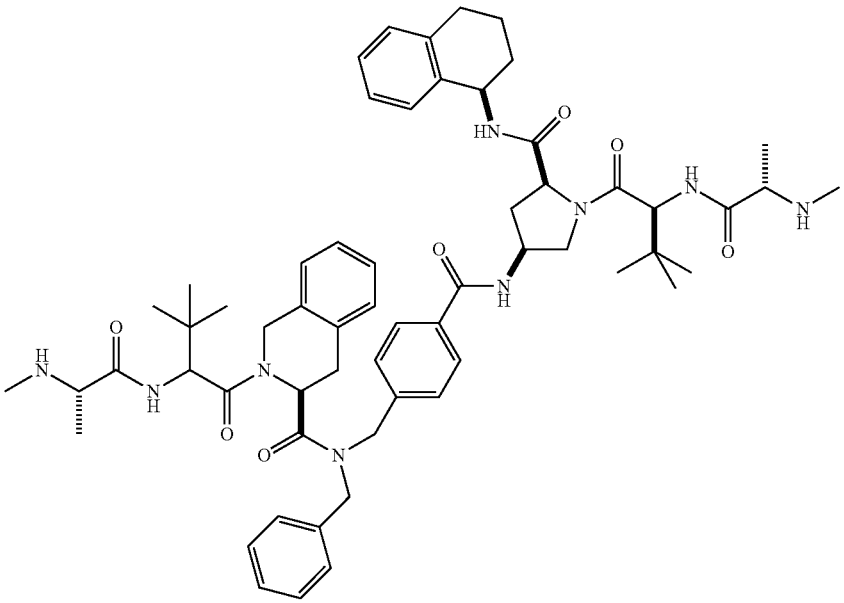 | (S)-N-Benzyl-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide | 1038.8 |

| Ex. No. | Structure | Name | LCMS (M + H) |
|---|---|---|---|
| 14 | 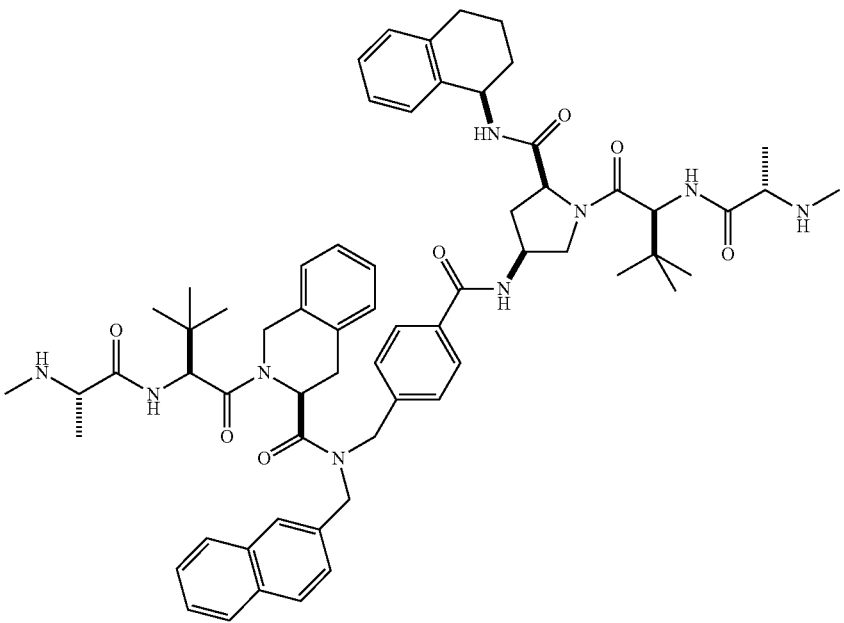 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-(naphthalen-2-ylmethyl)-1,2,3,4-tetrahydroisoquinoline-3-carboxamide | 1088.8 |
| 15 | 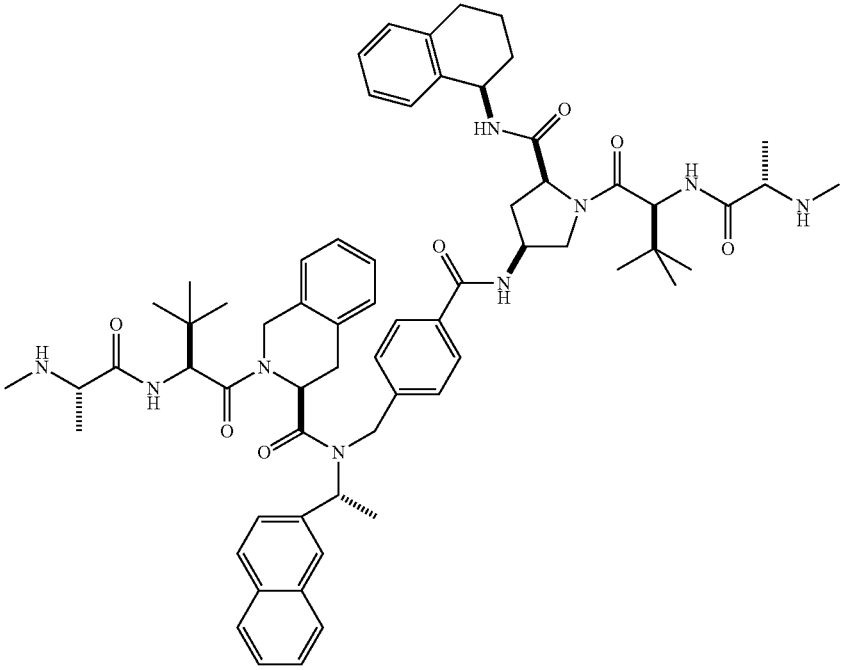 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(naphthalen-2-yl)ethyl)-1,2,3,4-tetrahydroisoquinoline-3-carboxamide | 1103.9 |

| Ex. No. | Structure | Name | LCMS (M + H) |
|---|---|---|---|
| 16 | 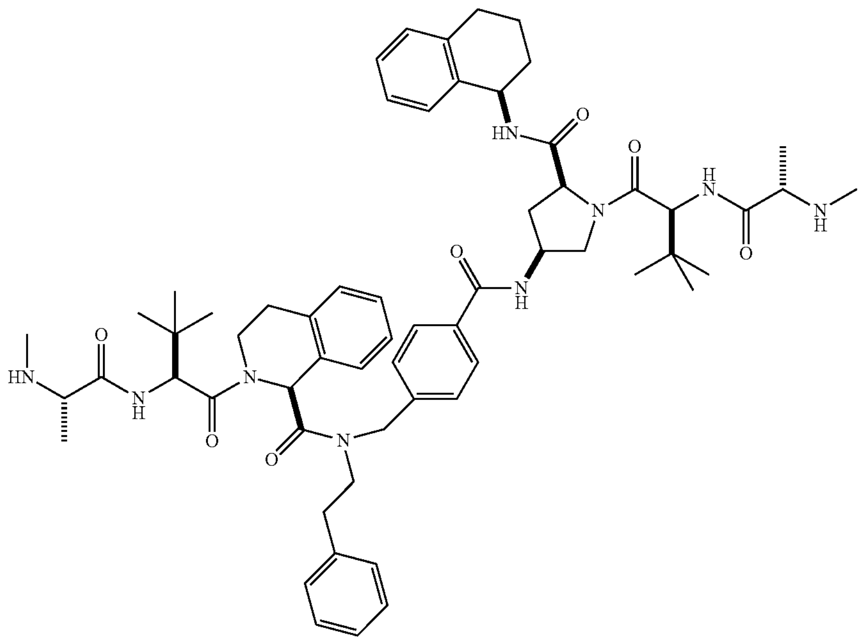 | (S)-2-((S)-3,3-Dimethyl-2-((S)-2-(methyl-amino)propanamido)butanoyl)-N-(4-((3S,5S)-1-((S)-3,3-dimethyl-2-((S)-2-(methylamino)propanamido)butanoyl)-5-(((R)-1,2,3,4-tetra-hydronaphthalen-1-yl)carbamoyl)pyrrolidin-3-yl)carbamoyl)benzyl)-N-phenethyl-1,2,3,4-tetrahydro-isoquinoline-1-carboxamide | 1052.8 |
| 17 | Chiral | N¹-(((S)-2-((S)-3,3-dimethyl-2-((S)-2-(methylamino)propanamido)butanoyl)-1,2,3,4-tetra-hydroisoquinolin-3-yl)methyl)-N⁴-((3S,5S)-1-((S)-3,3-dimethyl-2-((S)-2-(methyl-amino)propanamido)butanoyl)-5-(((R)-1,2,3,4-tetrahydro-naphthalen-1-yl)carbamoyl)pyrrolidin-3-yl)-N¹-((R)-1-(2-fluorophenyl)propan-2-yl)terephthalamide | 1085.5 |

| Ex. No. | Structure | Name | LCMS (M + H) |
|---|---|---|---|
| 18 | 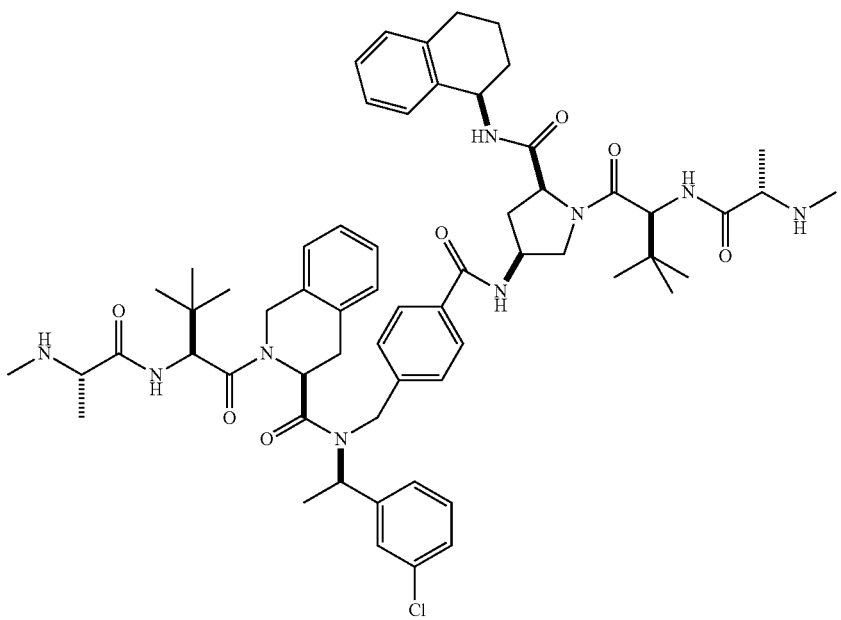 | (S)-N-((S)-1-(3-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide | 1086.9 |
| 19 | 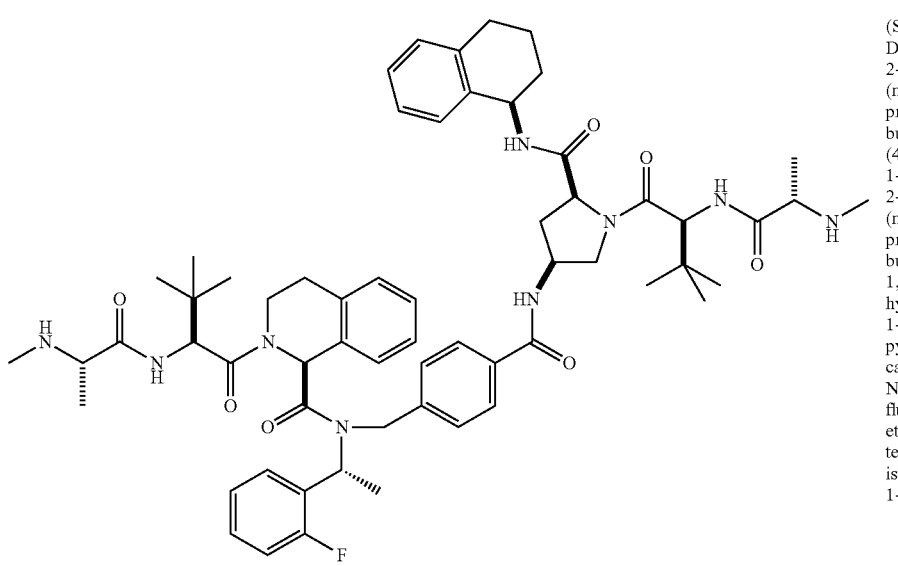 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)ethyl)-1,2,3,4-tetrahydroisoquinoline-1-carboxamide | 1070.9 |

-continued

| Ex. No. | Structure | Name | LCMS (M + H) |
|---|---|---|---|
| 20 | 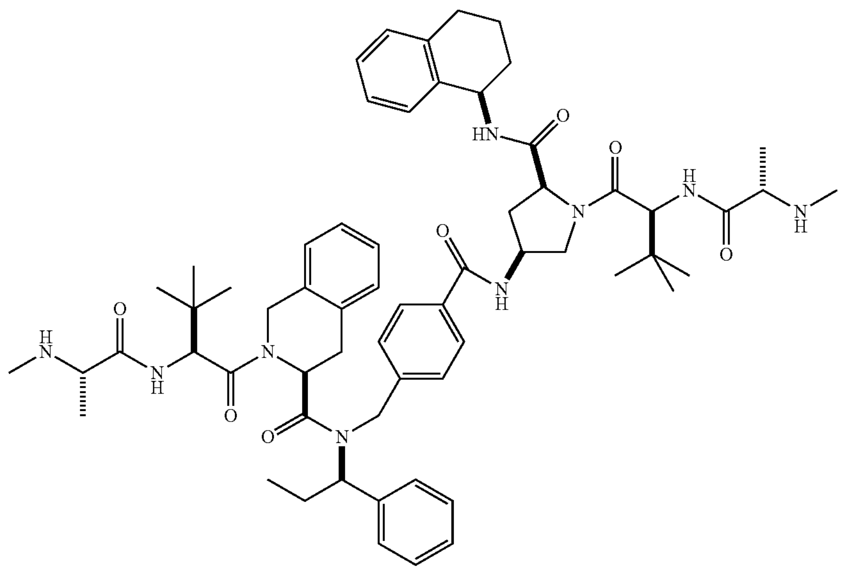 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-phenylpropyl)-1,2,3,4-tetrahydroisoquinoline-3-carboxamide | 1067.9 |
| 21 | 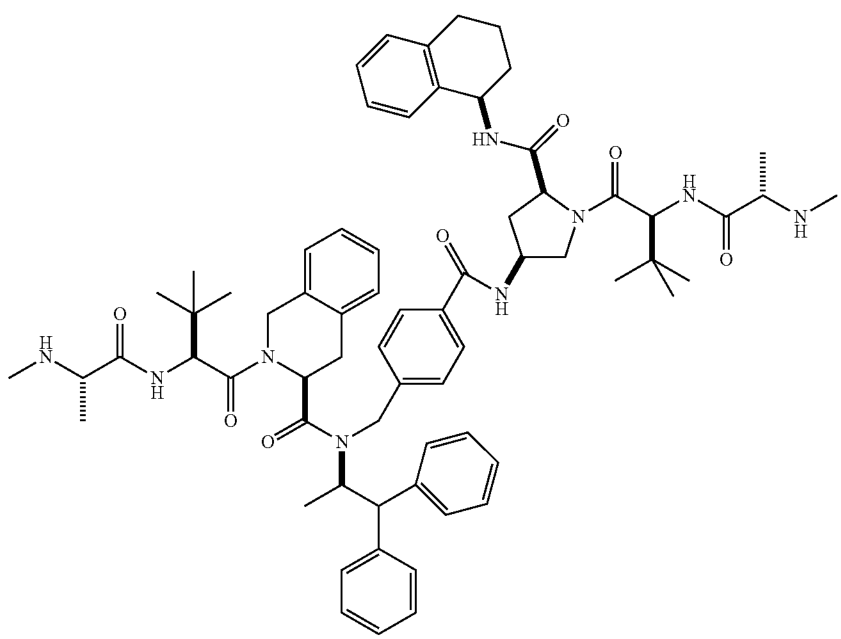 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1,1-diphenylpropan-2-yl)-1,2,3,4-tetrahydroisoquinoline-3-carboxamide | 1143.1 |

| Ex. No. | Structure | Name | LCMS (M + H) |
|---|---|---|---|
| 22 | 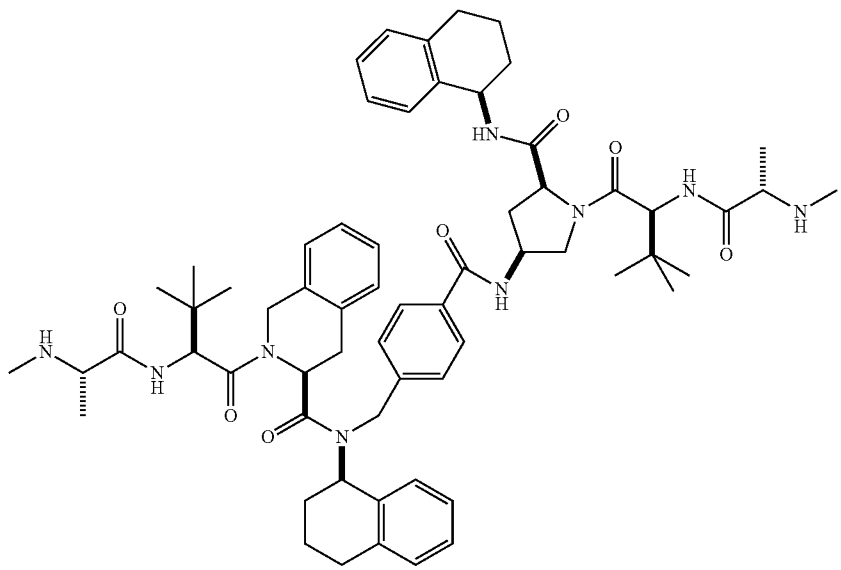 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((S)-1,2,3,4-tetrahydronapthalen-1-yl)-1,2,3,4-tetrahydroisoquinoline-3-carboxamide | 1078.9 |
| 23 | 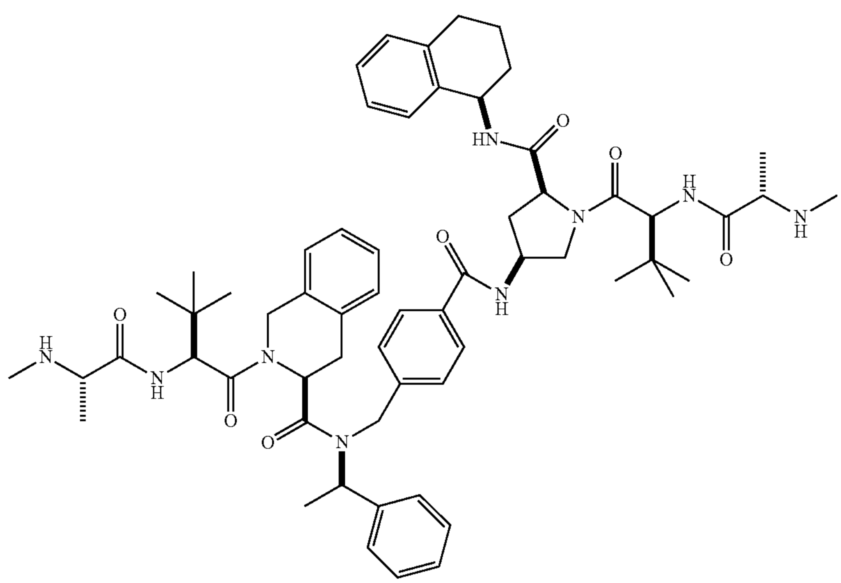 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-phenylethyl)-1,2,3,4-tetrahydroisoquinoline-3-carboxamide | 1052.6 |

| Ex. No. | Structure | Name | LCMS (M + H) |
|---|---|---|---|
| 24 | 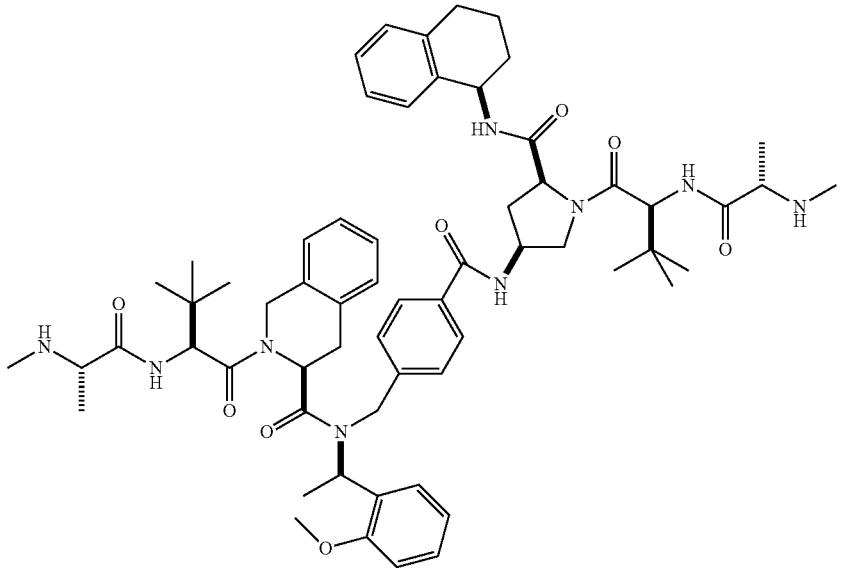 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-methoxyphenyl)ethyl)-1,2,3,4-tetrahydroisoquinoline-3-carboxamide | 1082.6 |
| 25 | 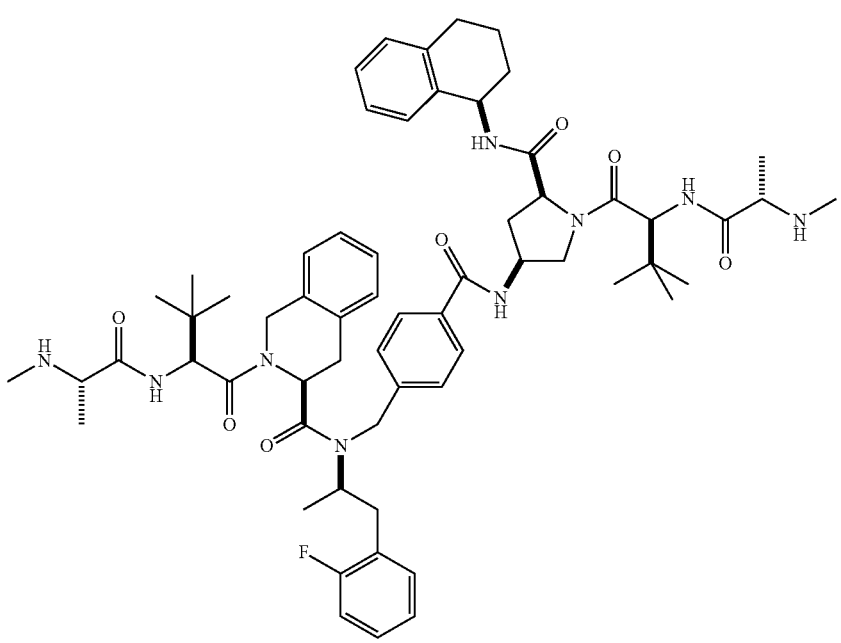 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)propan-2-yl)-1,2,3,4-tetrahydroisoquinoline-3-carboxamide | 1085.7 |

| Ex. No. | Structure | Name | LCMS (M + H) |
|---|---|---|---|
| 26 | 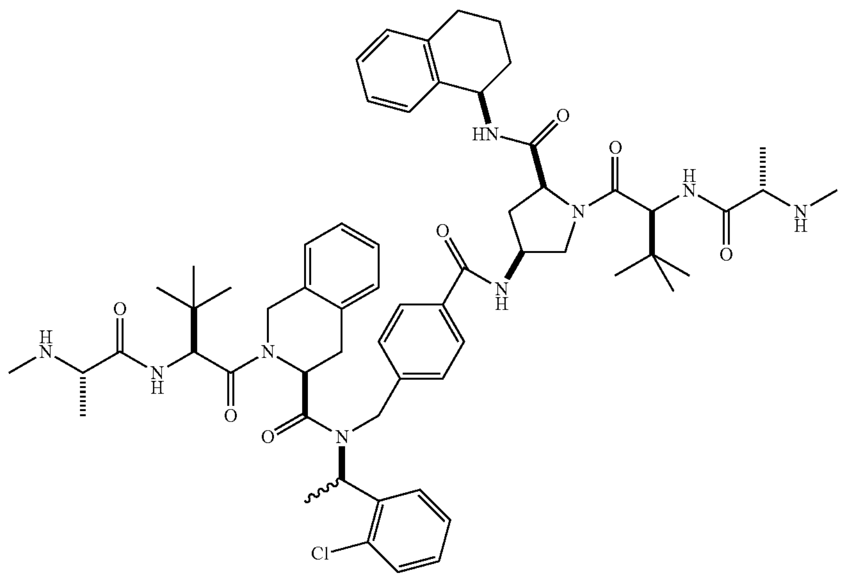 | (3S)-N-(1-(2-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide | 1086.7 |
| 27 | 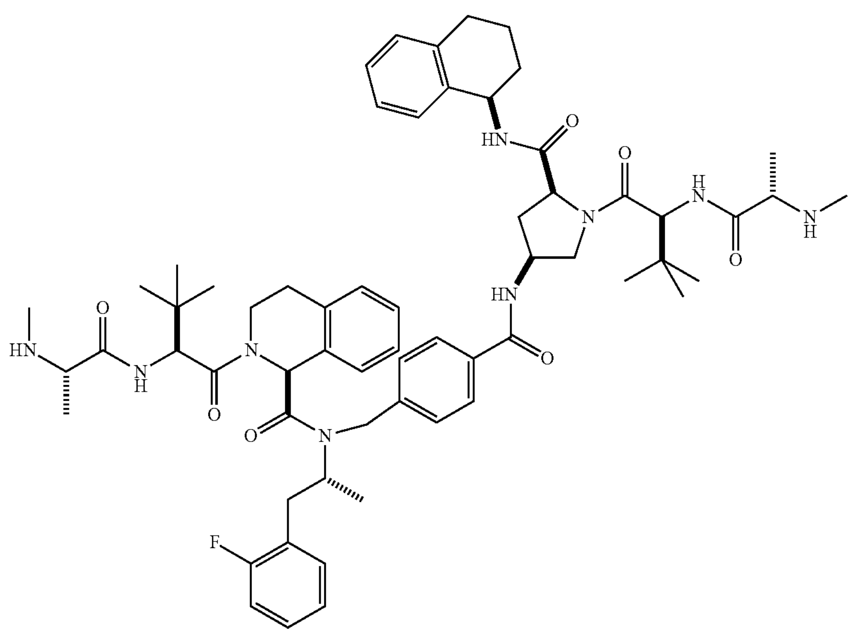 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)propan-2-yl)-1,2,3,4-tetrahydroisoquinoline-1-carboxamide | 1084.7 |

| Ex. No. | Structure | Name | LCMS (M + H) |
|---|---|---|---|
| 28 | 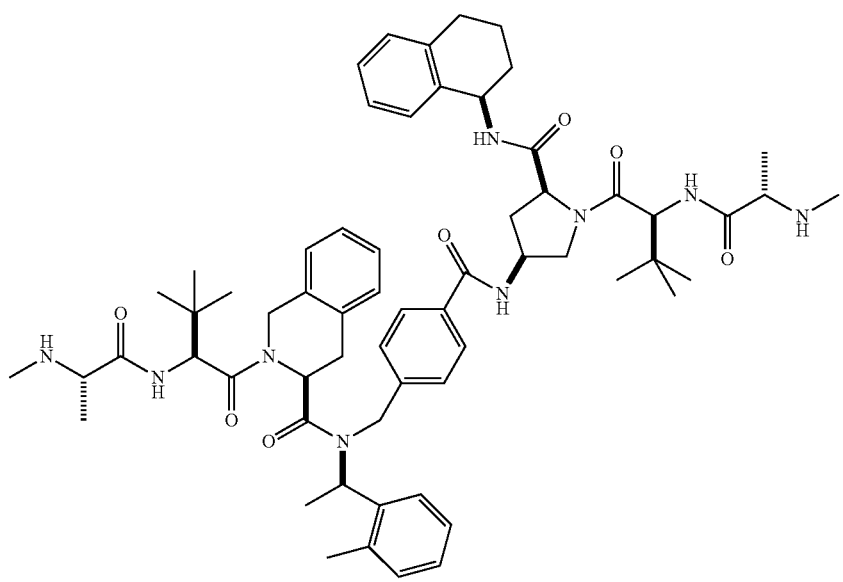 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(o-tolyl)ethyl)-1,2,3,4-tetrahydroisoquinoline-3-carboxamide | 1066.8 |
| 29 | 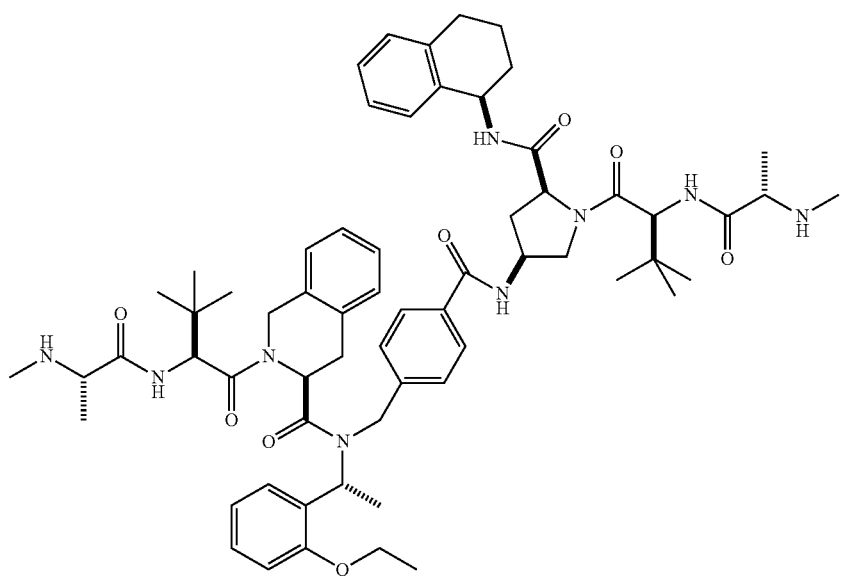 | (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-ethoxyphenyl)ethyl)-1,2,3,4-tetrahydroisoquinoline-3-carboxamide | 1096.7 |

| Ex. No. | Structure | Name | LCMS (M + H) |
|---|---|---|---|
| 30 | 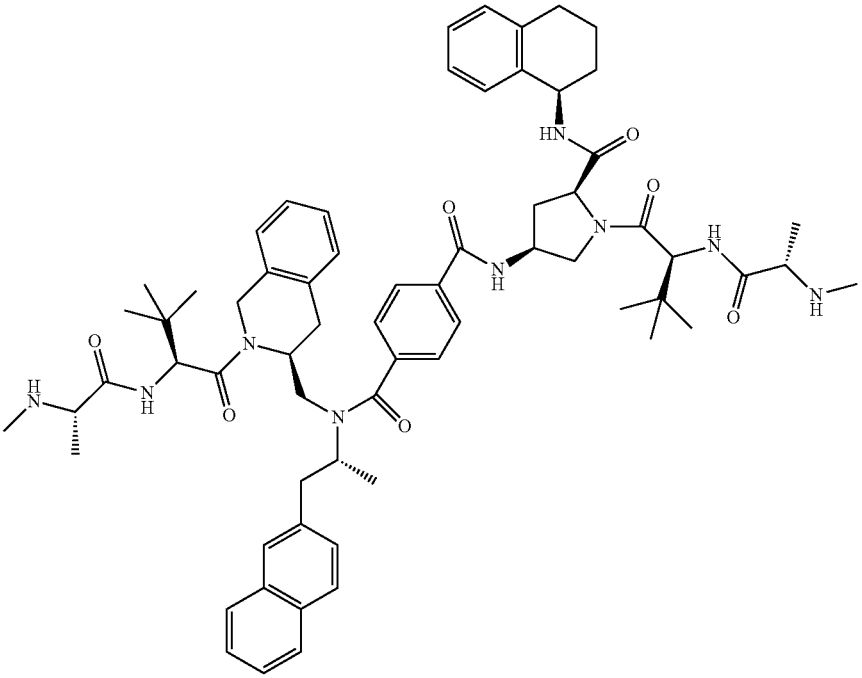 | $N^1$-(((S)-2-((S)-3,3-Dimethyl-2-((S)-2-(methylamino)propanamido)butanoyl)-1,2,3,4-tetrahydro-isoquinolin-3-yl)methyl)-$N^4$-((3S,5S)-1-((S)-3,3-dimethyl-2-((S)-2-(methylamino)propanamido)butanoyl)-5-(((R)-1,2,3,4-tetrahydro-naphthalen-1-yl)carbamoyl)pyrrolidin-3-yl)-$N^1$-((R)-1-(naphthalen-2-yl)propan-2-yl)terephthalamide | 1116.7 |
| 31 | 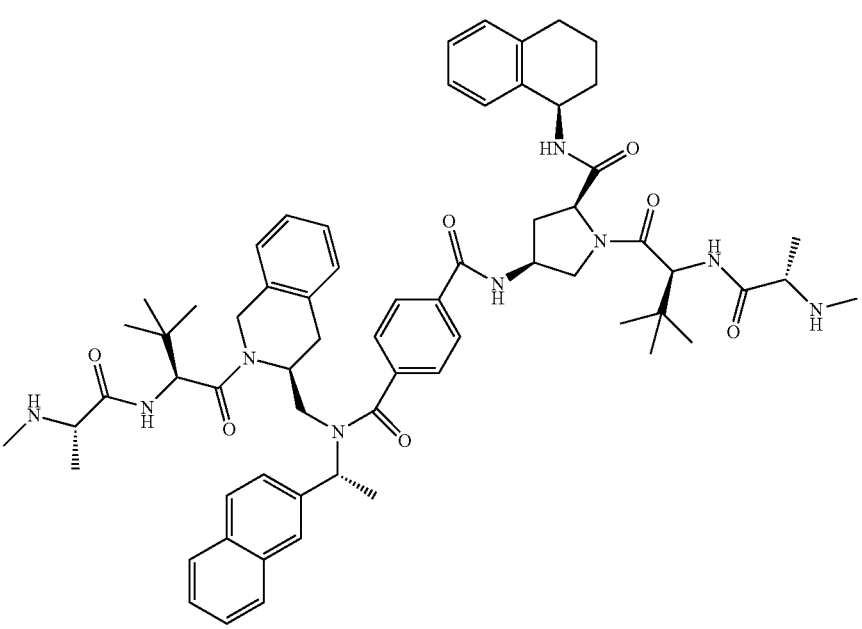 | $N^1$-(((S)-2-((S)-3,3-Dimethyl-2-((S)-2-(methylamino)propanamido)butanoyl)-1,2,3,4-tetrahydro-isoquinolin-3-yl)methyl)-$N^4$-((3S,5S)-1-((S)-3,3-dimethyl-2-((S)-2-(methylamino)propanamido)butanoyl)-5-(((R)-1,2,3,4-tetrahydro-naphthalen-1-yl)carbamoyl)pyrrolidin-3-yl)-$N^1$-((R)-1-(naphthalen-2-yl)ethyl)terephthalamide | 1102.8 |

| Ex. No. | Structure | Name | LCMS (M + H) |
|---|---|---|---|
| 32 | 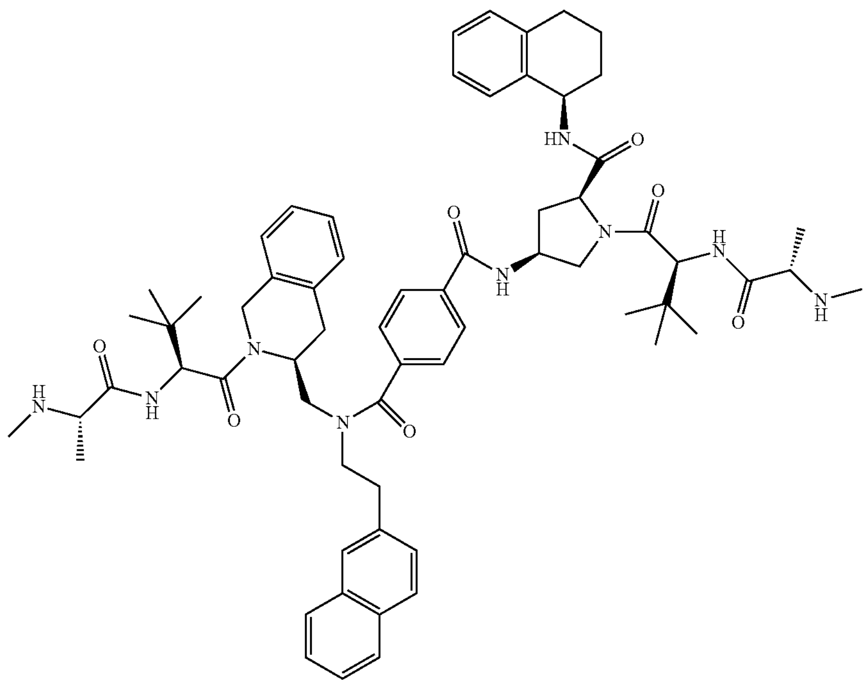 | $N^1$-(((S)-2-((S)-3,3-Dimethyl-2-((S)-2-(methylamino)propanamido)butanoyl)-1,2,3,4-tetrahydroisoquinolin-3-yl)methyl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-$N^1$-(2-(naphthalen-2-yl)ethyl)terephthalamide | 1102.8 |
| 33 | Chiral | $N^1$-(((S)-2-((S)-3,3-Dimethyl-2-((S)-2-(methylamino)propanamido)butanoyl)-1,2,3,4-tetrahydroisoquinolin-3-yl)methyl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-$N^1$-(2-(naphthalen-1-yl)ethyl)terephthalamide | 1103.6 |

| Ex. No. | Structure | Name | LCMS (M + H) |
|---|---|---|---|
| 34 | 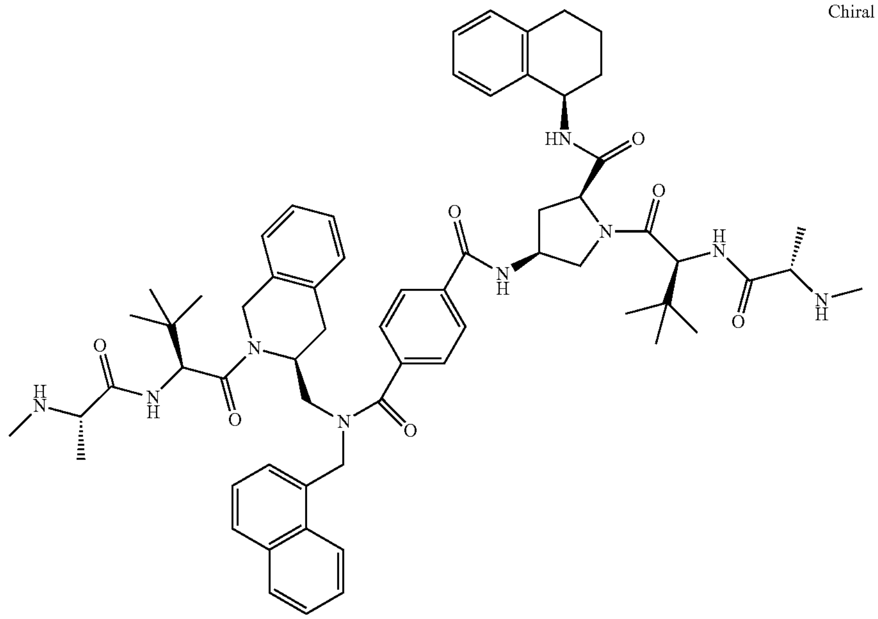 | Chiral N$^1$-(((S)-2-((S)-3,3-Dimethyl-2-((S)-2-(methylamino)propanamido)butanoyl)-1,2,3,4-tetrahydro-isoquinolin-3-yl)methyl)-N$^4$-((3S,5S)-1-((S)-3,3-dimethyl-2-((S)-2-(methylamino)propanamido)butanoyl)-5-(((R)-1,2,3,4-tetrahydro-naphthalen-1-yl)carbamoyl)pyrrolidin-3-yl)-N$^1$-(naphthalen-1-ylmethyl)terephthalamide | 1089.6 |
| 35 | 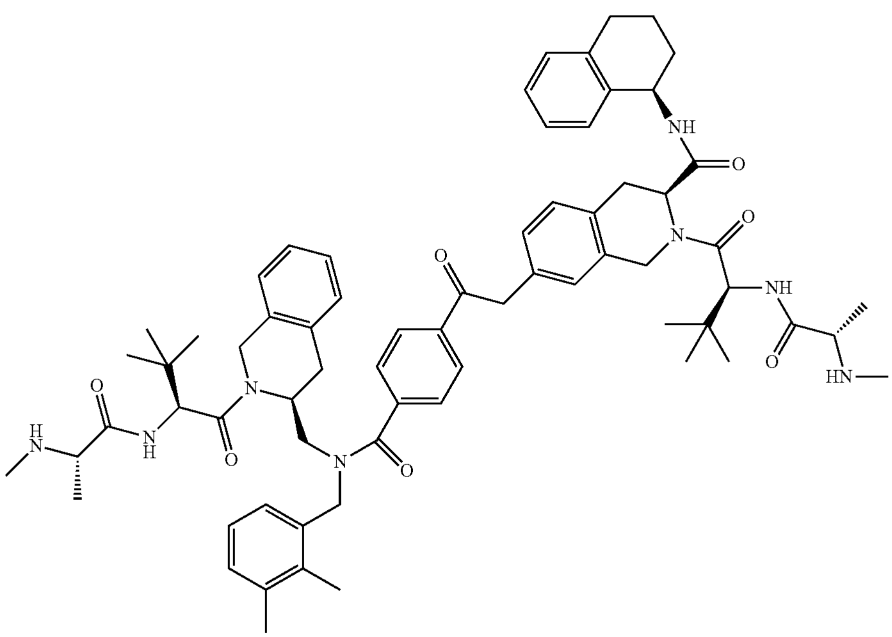 | N$^1$-(((S)-2-((S)-3,3-Dimethyl-2-((S)-2-(methylamino)propanamido)butanoyl)-1,2,3,4-tetra-hydroisoquinolin-3-yl)methyl)-N$^4$-((S)-2-((S)-3,3-dimethyl-2-((S)-2-(methylamino)propanamido)butanoyl)-3-(((R)-1,2,3,4-tetrahydro-naphthalen-1-yl)carbamoyl)-1,2,3,4-tetra-hydroisoquinolin-7-yl)-N$^1$-(2,3-dimethylbenzyl)terephthalamide | 1129.8 |

| Ex. No. | Structure | Name | LCMS (M + H) |
|---|---|---|---|
| 36 | 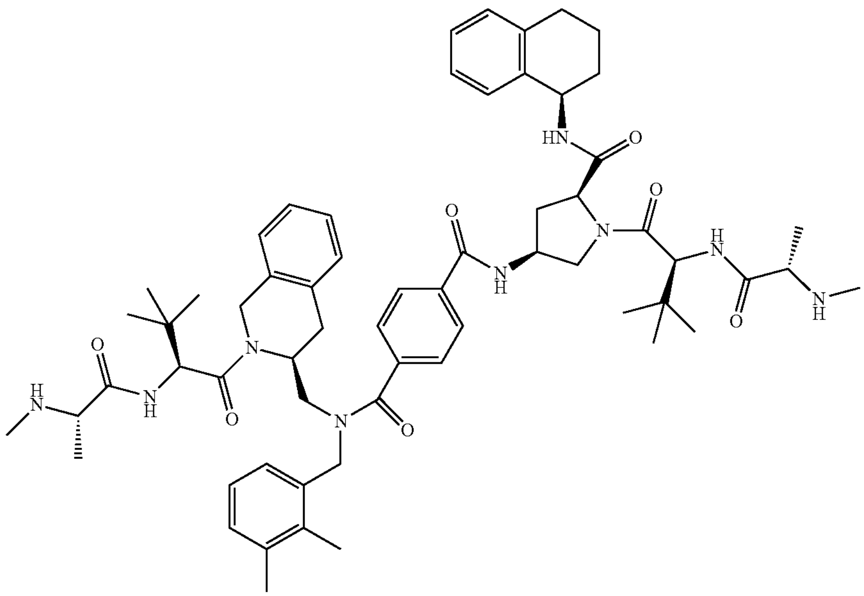 | $N^1$-(((S)-2-((S)-3,3-Dimethyl-2-((S)-2-(methylamino)propanamido)butanoyl)-1,2,3,4-tetrahydroisoquinolin-3-yl)methyl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-$N^1$-(2,3-dimethylbenzyl)terephthalamide | 1066.8 |
| 37 | 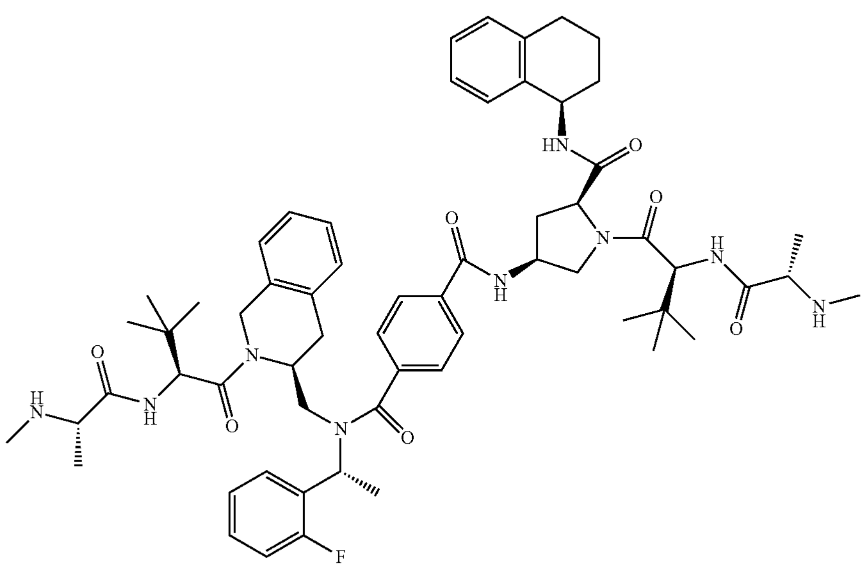 | $N^1$-(((S)-2-((S)-3,3-Dimethyl-2-((S)-2-(methylamino)propanamido)butanoyl)-1,2,3,4-tetrahydroisoquinolin-3-yl)methyl)-$N^4$-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)-$N^1$-((R)-1-(2-fluorophenyl)ethyl)terephthalamide | 1070.8 |

Example 38

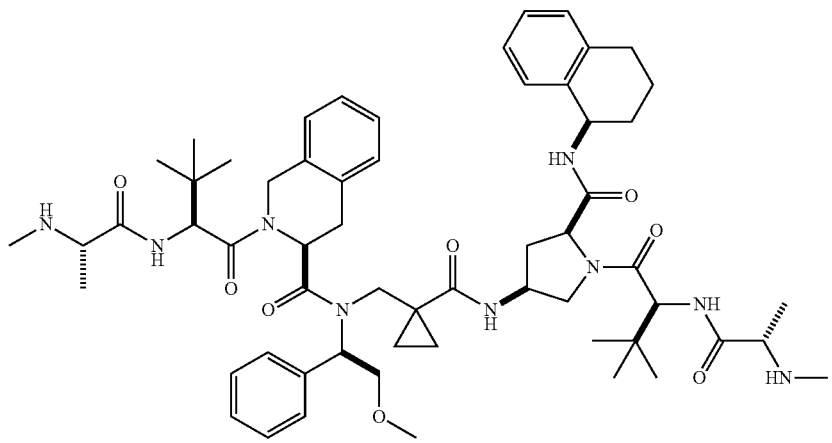

(S)-2-((S)-3,3-Dimethyl-2-((S)-2-(methylamino) propanamido)butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)cyclopropyl)methyl)-N-((S)-2-methoxy-1-phenylethyl)-1,2,3,4-tetrahydroisoquinoline-3-carboxamide, 2 TFA

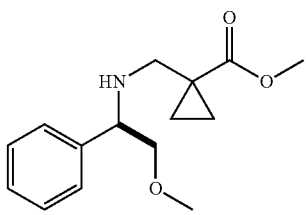 [SMILES: COC[C@H](NCC1(C(=O)OC)CC1)c1ccccc1]

A) (S)-Methyl 1-(((2-methoxy-1-phenylethyl)amino)methyl)cyclopropanecarboxylate

To a solution of (S)-2-methoxy-1-phenylethanamine (191 mg, 1.26 mmol, Chem-Impex) in DCM (3.0 mL) was added methyl 1-formylcyclopropanecarboxylate (300 mg, 2.34 mmol, prepared based on the procedure reported in WO 2009/023269, PCT/US2008/009786). The reaction mixture was stirred at room temperature for 10 min, and Na(OAc)$_3$BH (402 mg, 1.90 mmol) and i-PrOH (2.0 mL) were then added. The reaction mixture was stirred at room temperature overnight and quenched by adding MeOH (2.0 mL) and aq. K$_2$HPO$_4$. The reaction mixture was extracted with DCM (3×). The combined organic extracts were dried over MgSO$_4$, filtered and concentrated in vacuo to give a crude oil. Purification using flash column chromatography (gradient from 0% to 7% MeOH/CH$_2$Cl$_2$) provided the title compound (204 mg, 61%) as a colorless oil. $^1$H NMR (CDCl$_3$) δ 7.43-7.31 (m, 5H), 3.95 (dd, J=8.9, 4.3 Hz, 1H), 3.70 (s, 3H), 3.45-3.40 (m, 2H), 3.39 (s, 3H), 2.79 (d, J=12.3 Hz, 1H), 2.39 (d, J=12.5 Hz, 1H), 1.58 (br. s., 1H), 1.29-1.18 (m, 2H), 0.73-0.68 (m, 2H); MS(ESI$^+$) m/z 264.2 (M+H)$^+$.

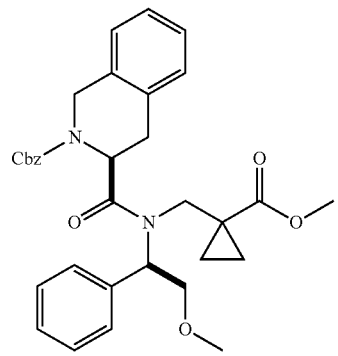

B) (S)-Benzyl 3-(((S)-2-methoxy-1-phenylethyl)((1-(methoxycarbonyl)cyclopropyl)methyl)carbamoyl)-3,4-dihydroisoquinoline-2(1H)-carboxylate To a solution of (S)-2-((benzyloxy)carbonyl)-1,2,3,4-tetrahydroisoquinoline-3-carboxylic acid (170 mg, 0.547 mmol, Chem-Impex) in DCE (2.0 mL) was added 1-chloro-N,N,2-trimethylprop-1-en-1-amine (91 mg, 0.68 mmol, Aldrich). The reaction mixture was stirred at room temperature for 15 min. To this solution was added a solution of (S)-methyl 1-(((2-methoxy-1-phenylethyl)amino)methyl)cyclopropanecarboxylate (120 mg, 0.456 mmol) and DIPEA (177 mg, 1.367 mmol) in DCE (0.5 mL). The reaction mixture was stirred at room temperature for 1 h. The reaction mixture was diluted with DCM and washed with aq. KH$_2$PO$_4$. The organic layer was separated and concentrated in vacuo. The residue was purified using flash column chromatography (gradient from 0% to 10% MeOH/CH$_2$Cl$_2$) to provide the title compound (180 mg, 71%) as a light yellow oil. MS(ESI$^+$) m/z 557.3 (M+H)$^+$.

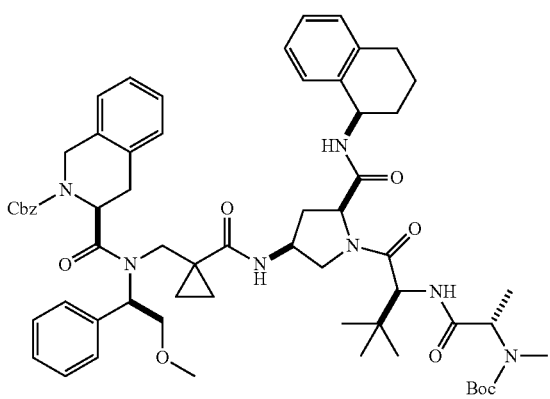

C) (S)-Benzyl 3-(((1-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)cyclopropyl)methyl)((S)-2-methoxy-1-phenylethyl)carbamoyl)-3,4-dihydroisoquinoline-2(1H)-carboxylate To a solution of (S)-benzyl 3-(((S)-2-methoxy-1-phenylethyl)((1-(methoxycarbonyl)cyclopropyl)methyl)carbamoyl)-3,4-dihydroisoquinoline-2(1H)-carboxylate (180 mg, 0.323 mmol) in THF (2.0 mL) and MeOH (2.0 mL) at room temperature was added 1N LiOH (1.62 mL, 1.62 mmol). The reaction mixture was stirred at room temperature for 7 h. The reaction mixture was then cooled to 0° C., neutralized to pH 3-4 with 1N HCl, and extracted with DCM (3×). The combined organic extracts were dried over MgSO₄, filtered and concentrated in vacuo to give crude 1-(((S)-2-((benzyloxy)carbonyl)-N-((S)-2-methoxy-1-phenylethyl)-1,2,3,4-tetrahydroisoquinoline-3-carboxamido)methyl)cyclopropanecarboxylic acid which was used directly in the next step.

To a solution of the crude product obtained above in DMF (2.0 mL) at room temperature were added HATU (243 mg, 0.640 mmol) and DIPEA (0.168 mL, 0.960 mmol). The reaction mixture was stirred at room temperature for 10 min, followed by the addition of the solution of tert-butyl ((S)-1-(((S)-1-(2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 196 mg, 0.35 mmol) in DMF (1.0 mL). The reaction mixture was stirred at room temperature for 1 h. The reaction was quenched by adding cold water (~10 mL). The solid formed was collected by filtration and purified by flash column chromatography (gradient from 0% to 10% MeOH/CH₂Cl₂) to provide the title compound (150 mg, 43%) as an off-white solid. MS(ESI⁺) m/z 1083.0 (M+H)⁺.

D) tert-Butyl ((S)-1-(((S)-1-((2S,4S)-4-(1-(((S)-2-((S)-2-(((((9H-fluoren-9-yl)methoxy)carbonyl)amino)-3,3-dimethylbutanoyl)-N-((S)-2-methoxy-1-phenylethyl)-1,2,3,4-tetrahydroisoquinoline-3-carboxamido)methyl)cyclopropanecarboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of (S)-benzyl 3-(((1-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)cyclopropyl)methyl)((S)-2-methoxy-1-phenylethyl)carbamoyl)-3,4-dihydroisoquinoline-2(1H)-carboxylate (210 mg, 0.19 mmol) in i-PrOH (10 mL) was added Pd(OH)₂ on carbon (27 mg, 0.19 mmol). The reaction mixture was degassed under vacuum and stirred under H₂ balloon for 1 h. The reaction mixture was then diluted with EtOAc (~30 mL) and filtered through CELITE®. The filtrate was concentrated in vacuo to give crude tert-butyl ((S)-1-(((S)-1-((2S,4S)-4-(1-(((S)-N-((S)-2-methoxy-1-phenylethyl)-1,2,3,4-tetrahydroisoquinoline-3-carboxamido)methyl)cyclopropanecarboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate, which was used directly in the next step.

To a solution of (S)-2-(((((9H-fluoren-9-yl)methoxy)carbonyl)(methyl)amino)-3,3-dimethylbutanoic acid (0.12 g, 0.33 mmol) in DMF (2.0 mL) at room temperature were added HATU (0.228 g, 0.60 mmol) and DIPEA (0.157 mL, 0.90 mmol). The reaction mixture was stirred at room temperature for 10 min and followed by the addition of a solution of tert-butyl ((S)-1-(((S)-1-((2S,4S)-4-(1-(((S)-N-((S)-2-methoxy-1-phenylethyl)-1,2,3,4-tetrahydroisoquinoline-3-carboxamido)methyl)cyclopropanecarboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (0.28 g, 0.30 mmol) in DMF (1.0 mL). The reaction mixture was stirred at room temperature for 2 h and then quenched by adding cold water (10 mL). The solid formed was collected by filtration and purified by flash column chromatography (gradient from 0% to 10% MeOH/CH₂Cl₂) to provide the title compound (243 mg, 63%) as a light brown solid. MS(ESI⁺) m/z 1284.2 (M+H)⁺.

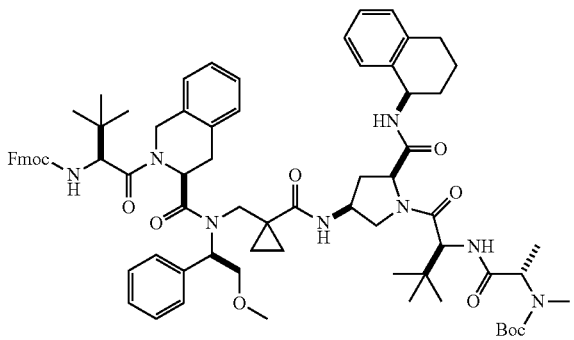

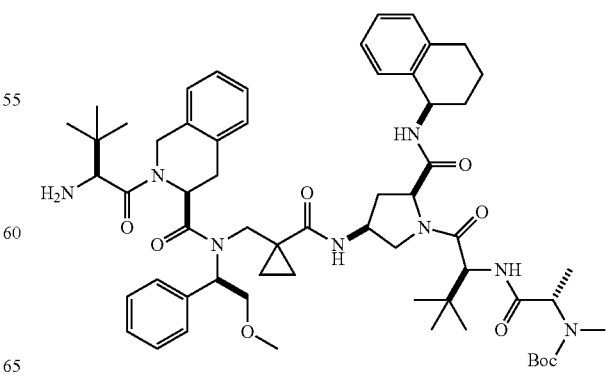

E) tert-Butyl ((S)-1-(((S)-1-((2S,4S)-4-(1-(((S)-2-((S)-2-amino-3,3-dimethylbutanoyl)-N-((S)-2-methoxy-1-phenylethyl)-1,2,3,4-tetrahydroisoquinoline-3-carboxamido)methyl)cyclopropanecarboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-(((S)-1-((2S,4S)-4-(1-(((S)-2-((S)-2-((((9H-fluoren-9-yl)methoxy)carbonyl)amino)-3,3-dimethylbutanoyl)-N-((S)-2-methoxy-1-phenyl-ethyl)-1,2,3,4-tetrahydroisoquinoline-3-carboxamido)methyl)cyclopropanecarboxamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (240 mg, 0.19 mmol) in DCM (4.0 mL) was added piperidine (0.18 mL, 1.87 mmol) dropwise. The reaction mixture was stirred at room temperature for 2 h and then concentrated in vacuo. MeOH (5.0 mL) was added to the residue, and the resulting white solid was removed by filtration. The filtrate was purified by prep HPLC to give the title compound (141 mg, 71%). MS(ESI⁺) m/z 1061.8 (M+H)⁺.

F) (S)-2-((S)-3,3-Dimethyl-2-((S)-2-(methylamino)propanamido)butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)cyclopropyl)methyl)-N-((S)-2-methoxy-1-phenylethyl)-1,2,3,4-tetrahydroisoquinoline-3-carboxamide To a solution of (S)-2-((tert-butoxycarbonyl)(methyl)amino)propanoic acid (15.3 mg, 0.075 mmol) in DMF (0.5 mL) were added EDC (21.7 mg, 0.11 mmol), HOAt (15.4 mg, 0.11 mmol) and NMM (0.021 mL, 0.19 mmol). The reaction mixture was stirred at room temperature for 5 min, followed by addition of a solution of (S)-2-((S)-2-Amino-3,3-dimethylbutanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)cyclopropyl)methyl)-N-((S)-2-methoxy-1-phenylethyl)-1,2,3,4-tetrahydroisoquinoline-3-carboxamide (40 mg, 0.038 mmol) in DMF (0.5 mL). The resulting reaction mixture was stirred at room temperature for 1 h and then purified by prep HPLC to give the N-Boc precursor (28 mg, 60%). MS(ESI⁺) m/z 1246.9 (M+H)⁺.

To a solution of the above compound (28 mg, 0.022 mmol) in DCM (2.0 mL) was added TFA (0.5 mL). The reaction mixture was stirred at room temperature for 1 h and then concentrated in vacuo. The residue was dissolved in MeCN/H₂O and lyophilized to provide the title compound (29 mg, 100%) as a white solid. MS(ESI⁺) m/z 1047.2 (M+H)⁺.

Example 39

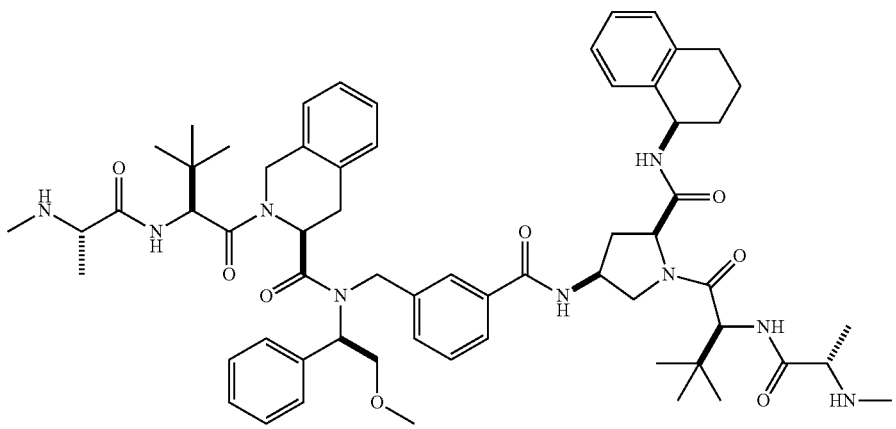

(S)-2-((S)-3,3-Dimethyl-2-((S)-2-(methylamino)propanamido)butanoyl)-N-(3-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((S)-2-methoxy-1-phenylethyl)-1,2,3,4-tetrahydroisoquinoline-3-carboxamide

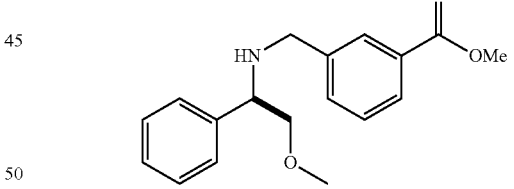

A) (S)-Methyl 3-(((2-methoxy-1-phenylethyl)amino)methyl)benzoate

To a solution of methyl 3-(bromomethyl)benzoate (458 mg, 2.00 mmol, Aldrich) in DMF (5.0 mL) were added (S)-2-methoxy-1-phenylethanamine (302 mg, 2.00 mmol, Chem-Impex) and K₂CO₃ (829 mg, 6.00 mmol). The reaction mixture was stirred at room temperature overnight and then quenched by adding ~50 mL of cold water. The semi-solid formed was collected by filtration and purified by flash column chromatography (gradient from 0 to 10% MeOH/CH₂Cl₂) to provide the title compound (400 mg, 67%) as an off white solid. MS(ESI⁺) m/z 300.2 (M+H)⁺.

B) (S)-2-((S)-3,3-Dimethyl-2-((S)-2-(methylamino) propanamido)butanoyl)-N-(3-(((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)carbamoyl)benzyl)-N-((S)-2-methoxy-1-phenylethyl)-1,2,3,4-tetrahydroisoquinoline-3-carboxamide Following procedures analogous to those for the preparation of Compounds B, C, D, E and F of Example 38, (S)-methyl 3-(((2-methoxy-1-phenylethyl)amino)methyl)benzoate was converted to the title compound. MS(ESI+) m/z 1082.7 (M+H)+.

Example 40

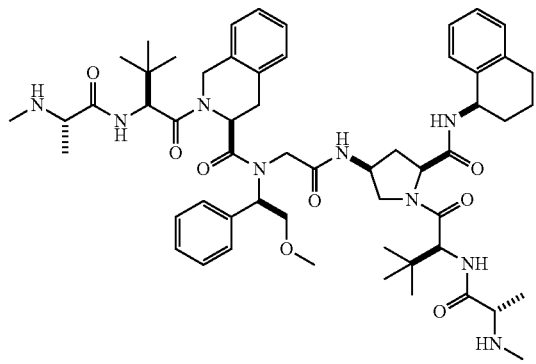

(S)-2-((S)-3,3-Dimethyl-2-((S)-2-(methylamino) propanamido)butanoyl)-N-(2-(((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)amino)-2-oxoethyl)-N-((S)-2-methoxy-1-phenylethyl)-1,2,3,4-tetrahydroisoquinoline-3-carboxamide A) (S)-Ethyl 2-((2-methoxy-1-phenylethyl)amino)acetate To a solution of (S)-2-methoxy-1-phenylethanamine (302 mg, 2.00 mmol, Chem-Impex) in DMF (2 ml) was added ethyl 2-bromoacetate (334 mg, 2.00 mmol, Aldrich) and K₂CO₃ (829 mg, 6.00 mmol). The reaction mixture was stirred at room temperature for 2 h and then quenched by adding cold water (~10 mL). The mixture was extracted with DCM (3×). The combined organic extracts were dried over MgSO₄, filtered and concentrated in vacuo. The residue was purified by flash column chromatography (gradient from 0% to 10% MeOH/CH₂Cl₂) to provide the title compound (356 mg, 75%) as a viscous oil. ¹H NMR (CDCl₃) δ 7.39-7.26 (m, 5H), 4.16 (q, J=7.1 Hz, 2H), 3.96 (dd, J=7.7, 5.5 Hz, 1H), 3.46 (d, J=2.4 Hz, 1H), 3.45 (s, 1H), 3.40 (s, 3H), 3.37-3.31 (m, 1H), 3.24-3.17 (m, 1H), 1.24 (t, J=7.1 Hz, 3H); MS(ESI+) m/z 238.2 (M+H)+.

B) (S)-2-((S)-3,3-Dimethyl-2-((S)-2-(methylamino) propanamido)butanoyl)-N-(2-(((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)amino)-2-oxoethyl)-N-((S)-2-methoxy-1-phenylethyl)-1,2,3,4-tetrahydroisoquinoline-3-carboxamide Following procedures analogous to those for the preparation of Compounds B, C, D, E and F of Example 38, (S)-ethyl 2-((2-methoxy-1-phenylethyl)amino)acetate was converted to the title compound. MS(ESI+) m/z 1006.6 (M+H)+.

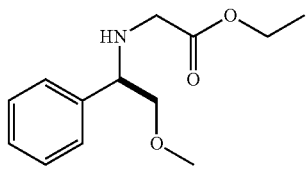 [SMILES: CCOC(=O)CN[C@@H](COC)c1ccccc1]

Example 41

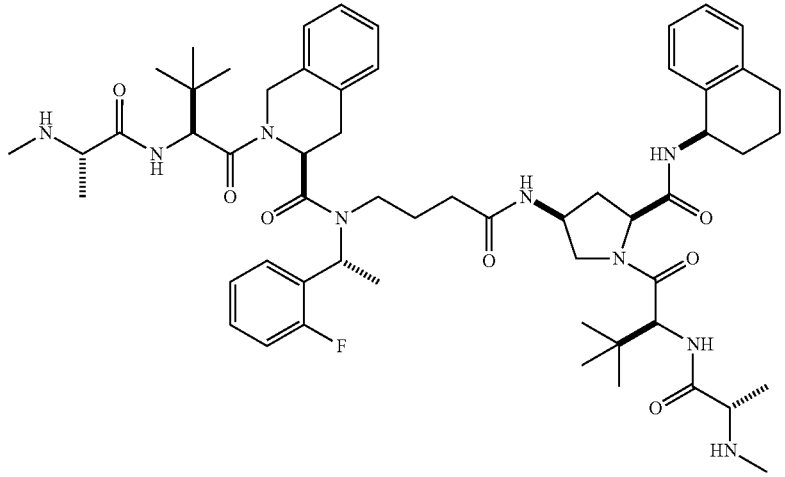

(S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)amino)-4-oxobutyl)-N-((R)-1-(2-fluorophenyl)ethyl)-1,2,3,4-tetrahydroisoquinoline-3-carboxamide

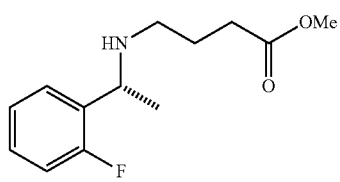 [SMILES: COC(=O)CCCN[C@H](C)c1ccccc1F]

B) (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)amino)-4-oxobutyl)-N-((R)-1-(2-fluorophenyl)ethyl)-1,2,3,4-tetrahydroisoquinoline-3-carboxamide Following procedures analogous to those for the preparation of Compounds B, C, D, E and F of Example 38, (R)-methyl 4-((1-(2-fluorophenyl)ethyl)amino)butanoate was converted to the title compound. MS(ESI$^+$) m/z 1022.8 (M+H)$^+$.

Example 42

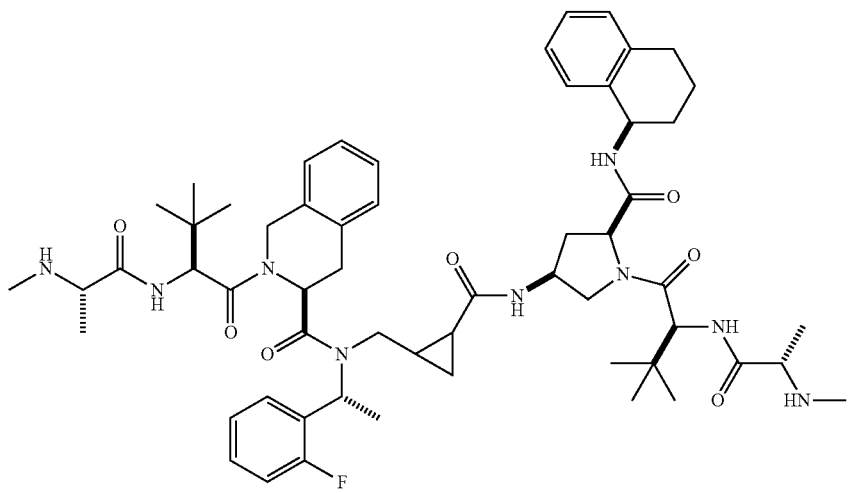

A) (R)-Methyl 4-((1-(2-fluorophenyl)ethyl)amino)butanoate

To a solution of (R)-1-(2-fluorophenyl)ethanamine (278 mg, 2.0 mmol, Kingston) in DCM (3.0 mL) was added methyl 4-oxobutanoate (232 mg, 2.0 mmol, Aldrich). The reaction mixture was stirred at room temperature for 30 min, and Na(OAc)$_3$BH (636 mg, 3.00 mmol) and i-PrOH (2.0 mL) were then added. The reaction mixture was stirred at room temperature for 1 h. The reaction was quenched with MeOH (2.0 mL) and sat. aq. K$_2$HPO$_4$ (2.0 mL) and then diluted with DCM (50 mL). The organic layer was separated, dried over MgSO$_4$, filtered and concentrated in vacuo. The residue was purified by preparative HPLC to provide the desired product (239 mg, 50%) as a white solid. $^1$H NMR (CDCl$_3$) δ 7.37 (td, J=7.5, 1.8 Hz, 1H), 7.21-7.14 (m, 1H), 7.12-7.07 (m, 1H), 6.98 (ddd, J=10.6, 8.1, 1.1 Hz, 1H), 4.09 (q, J=6.6 Hz, 1H), 3.62 (s, 3H), 2.58-2.50 (m, 1H), 2.48-2.40 (m, 1H), 2.33 (td, J=7.4, 3.3 Hz, 2H), 1.81-1.73 (m, 2H), 1.35 (d, J=6.6 Hz, 3H); MS(ESI$^+$) m/z 240.2 (M+H)$^+$.

(3S)-2-((S)-3,3-Dimethyl-2-((S)-2-(methylamino)propanamido)butanoyl)-N-((2-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)cyclopropyl)methyl)-N-((R)-1-(2-fluorophenyl)ethyl)-1,2,3,4-tetrahydroisoquinoline-3-carboxamide

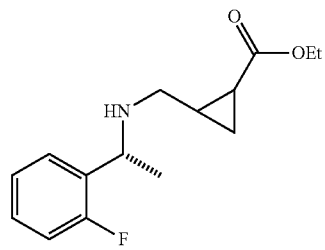 [SMILES: CCOC(=O)C1CC1CN[C@H](C)c1ccccc1F]

A) Ethyl 2-((((R)-1-(2-fluorophenyl)ethyl)amino)methyl)cyclopropanecarboxylate

To a solution of (R)-1-(2-fluorophenyl)ethanamine (278 mg, 2.0 mmol) in DCM (3.0 mL) and i-PrOH (2.0 mL) were added ethyl 2-formylcyclopropanecarboxylate (284 mg, 2.0 mmol, Aldrich) and Na(OAc)$_3$BH (636 mg, 3.0 mmol). The reaction mixture was stirred at room temperature for 1 h. The reaction was quenched with MeOH (2.0 mL) and a few drops of NH$_4$OH and then diluted with DCM. The organic layer was separated, dried over MgSO$_4$, filtered and concentrated in vacuo. The residue was purified by preparative HPLC to provide the desired product (265 mg, 50%) as a white solid. $^1$H NMR (CDCl$_3$) δ 7.43-7.35 (m, 1H), 7.25-7.18 (m, 1H), 7.16-7.10 (m, 1H), 7.05-6.98 (m, 1H), 4.19-4.07 (m, 3H), 2.54-2.45 (m, 1H), 2.43-2.33 (m, 1H), 1.64-1.55 (m, 1H), 1.40 (d, J=6.8 Hz, 3H), 1.44-1.35 (m, 1H), 1.25 (t, J=7.2 Hz, 3H), 1.17 (ddt, J=11.5, 8.8, 4.5 Hz, 1H), 0.76-0.66 (m, 1H); MS(ESI$^+$) m/z 266.2 (M+H)$^+$.

B) (3S)-2-((S)-3,3-Dimethyl-2-((S)-2-(methylamino) propanamido)butanoyl)-N-((2-(((3S,5S)-1-((S)-3,3-dimethyl-2-((S)-2-(methylamino)propanamido)butanoyl)-5-(((R)-1,2,3,4-tetrahydronaphthalen-1-yl) carbamoyl)pyrrolidin-3-yl)carbamoyl)cyclopropyl) methyl)-N-((R)-1-(2-fluorophenyl)ethyl)-1,2,3,4-tetrahydroisoquinoline-3-carboxamide Following procedures analogous to those for the preparation of Compounds B, C, D, E and F of Example 38, ethyl 2-((((R)-1-(2-fluorophenyl)ethyl)amino)methyl)cyclopropanecarboxylate was converted to the title compound. MS(ESI$^+$) m/z 1034.6 (M+H)$^+$.

Example 43

A) (R)-Methyl 1-(((1-(2,3-difluorophenyl)ethyl) amino)methyl)cyclopropanecarboxylate To a solution of (R)-1-(2,3-difluorophenyl)ethanamine (220 mg, 1.40 mmol, APAC) in DCM (3.0 mL) was added methyl 1-formylcyclopropanecarboxylate (256 mg, 1.40 mmol). The mixture was stirred at room temperature for 10 min, and then Na(OAc)$_3$BH (445 mg, 2.10 mmol) and i-PrOH (2.0 mL) were added. The reaction mixture was stirred at room temperature for 1 h, quenched with MeOH (2.0 mL) and aq. K$_2$HPO$_4$ (2.0 mL) and then diluted with DCM. The organic layer was separated, dried over MgSO$_4$, filtered and concentrated in vacuo. The residue was purified by preparative HPLC to provide the desired product (238 mg, 63%) as a white solid. $^1$H NMR (CD$_3$OD) δ 7.46-7.31 (m, 3H), 4.78 (q, J=7.0 Hz, 1H), 3.69 (s, 3H), 3.28-3.23 (m, 1H), 3.17 (m, 1H), 1.75 (d, J=7.0 Hz, 3H), 1.43-1.35 (m, 2H), 1.21-1.14 (m, 1H), 1.08-1.01 (m, 1H); MS(ESI$^+$) m/z 270.4 (M+H)$^+$.

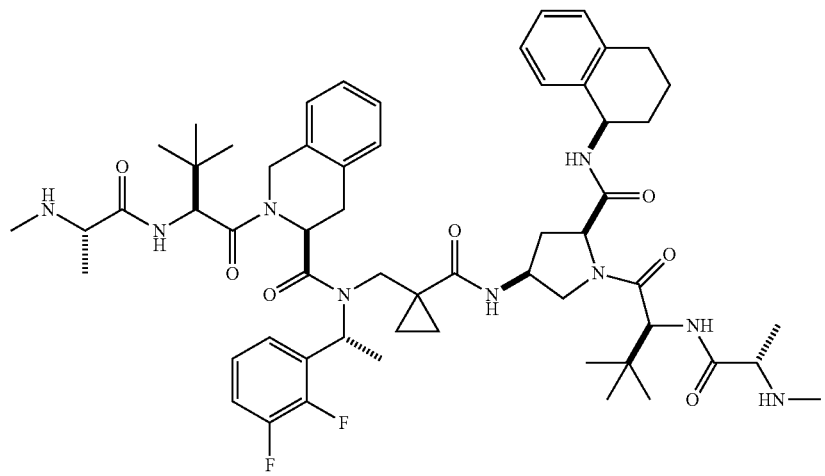

(S)-N-((R)-1-(2,3-Difluorophenyl)ethyl)-2-((S)-3,3-dimethyl-2-((S)-2-(methylamino)propanamido)butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)cyclopropyl)methyl)-1,2,3,4-tetrahydroisoquinoline-3-carboxamide

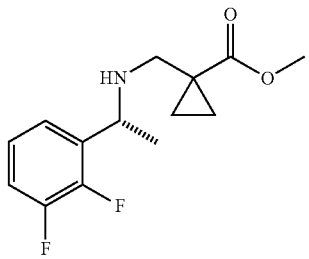 [SMILES: COC(=O)C1(CN[C@H](C)c2cccc(F)c2F)CC1]

B) (S)-N-((R)-1-(2,3-difluorophenyl)ethyl)-2-((S)-3,3-dimethyl-2-((S)-2-(methylamino)propanamido) butanoyl)-N-((1-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl) pyrrolidin-3-yl)carbamoyl)cyclopropyl)methyl)-1,2,3,4-tetrahydroisoquinoline-3-carboxamide Following procedures analogous to those for the preparation of Compounds B, C, D, E and F of Example 38, (R)-methyl 1-(((1-(2,3-difluorophenyl)ethyl)amino) methyl) cyclopropanecarboxylate was converted to the title compound. MS(ESI$^+$) m/z 1052.4 (M+H)$^+$.

Example 44

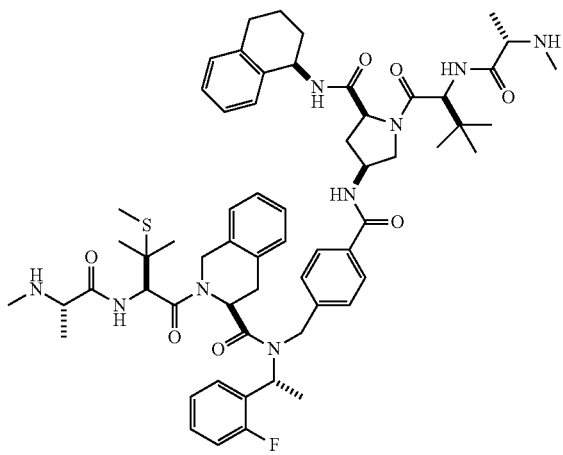

(S)-N-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)ethyl)-2-((R)-3-methyl-2-((S)-2-(methylamino)propanamido)-3-(methylthio)butanoyl)-1,2,3,4-tetrahydroisoquinoline-3-carboxamide

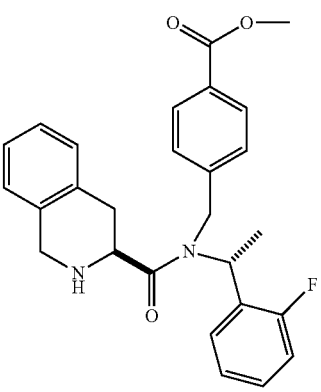 [SMILES: COC(=O)c1ccc(CN(C(=O)[C@@H]2Cc3ccccc3CN2)[C@H](C)c2ccccc2F)cc1]

A) Methyl 4-(((S)-N-((R)-1-(2-fluorophenyl)ethyl)-1,2,3,4-tetrahydroisoquinoline-3-carboxamido)methyl)benzoate To a solution of (S)-benzyl 3-(((R)-1-(2-fluorophenyl)ethyl)(4-(methoxycarbonyl)benzyl)carbamoyl)-3,4-dihydroisoquinoline-2(1H)-carboxylate (220 mg, 0.38 mmol, Compound D of Example 1) in MeOH (6 mL) was added 10% Pd—C (121 mg, 0.11 mmol). The reaction mixture was degassed under vacuum and stirred under $H_2$ balloon at rt for 3 h. The reaction mixture was filtered through a CELITE® pad and the pad was washed with MeOH. The combined filtrate was concentrated in vacuo to give the title compound as a white solid (155 mg, 92%). $^1$H NMR (DMSO-$d_6$) δ 7.82 (d, J=8.1 Hz, 1H), 7.74 (d, J=8.1 Hz, 1H), 7.46 (dt, J=15.2, 7.7 Hz, 1H), 7.31-6.88 (m, 9H), 5.99 (q, J=7.0 Hz, 0.5H), 5.89 (q, J=6.6 Hz, 0.5H), 5.75 (s, 1H), 4.95 (d, J=18.7 Hz, 0.5H), 4.69 (d, J=18.5 Hz, 0.5H), 4.59-4.42 (m, 1H), 4.19-4.07 (m, 1H), 3.99 (br. s., 0.5H), 3.81 (s, 3H), 3.50 (br. s., 0.5H), 3.10-2.79 (m, 1H), 2.76-2.56 (m, 1H), 1.57 (d, J=6.8 Hz, 1.5H), 1.42 (d, J=7.3 Hz, 1.5H)); MS(ESI$^+$) m/z 447.4 (M+H)$^+$.

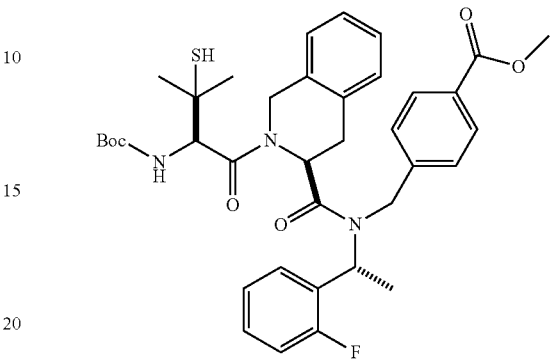

B) Methyl 4-(((S)-2-((R)-2-((tert-butoxycarbonyl)amino)-3-mercapto-3-methylbutanoyl)-N-((R)-1-(2-fluorophenyl)ethyl)-1,2,3,4-tetrahydroisoquinoline-3-carboxamido)methyl)benzoate To a solution of (R)-2-((tert-butoxycarbonyl)amino)-3-mercapto-3-methylbutanoic acid (48 mg, 0.19 mmol) in DCM (5 mL) was added 4-(4,6-dimethoxy[1,3,5]triazin-2-yl)-4-methylmorpholinium chloride hydrate (58 mg, 0.21 mmol). The reaction mixture was stirred at rt for 1.5 h and treated with a solution of methyl 4-(((S)-N-((R)-1-(2-fluorophenyl)ethyl)-1,2,3,4-tetrahydroisoquinoline-3-carboxamido)methyl)benzoate, TFA (90 mg, 0.16 mmol) in DCM (2 mL) followed by DIEA (0.1 mL, 0.5 mmol). The resulting mixture was stirred at rt for 40 h and concentrated in vacuo. The residue was purified by preparative HPLC. Fractions containing the desired product were combined, concentrated, and lyophilized to give the title compound as a white solid (47 mg, 43%). $^1$H NMR (CDCl$_3$) δ 8.13-7.78 (m, 2H), 7.49-7.28 (m, 3H), 7.26-6.76 (m, 7H), 5.98-5.53 (m, 2H), 5.35-4.81 (m, 4H), 4.78-4.40 (m, 2H), 4.01-3.88 (m, 3H), 3.21-2.47 (m, 3H), 1.76-1.59 (m, 3H), 1.55-1.39 (m, 12H), 1.33 (d, J=19.6 Hz, 1H); MS(ESI$^+$) m/z 678.4 (M+H)$^+$.

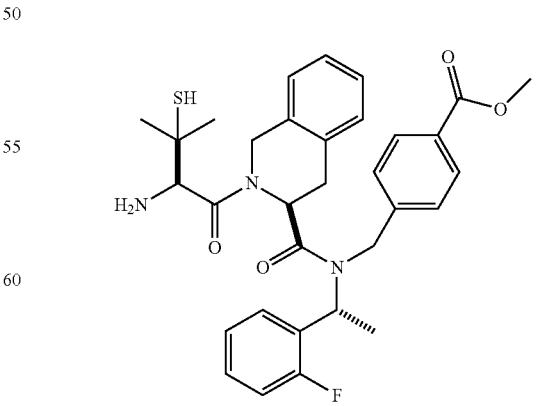

C) Methyl 4-(((S)-2-((R)-2-amino-3-mercapto-3-methylbutanoyl)-N-((R)-1-(2-fluorophenyl)ethyl)-1,2,3,4-tetrahydroisoquinoline-3-carboxamido)methyl)benzoate To a solution of methyl 4-(((S)-2-((R)-2-((tert-butoxycarbonyl)amino)-3-mercapto-3-methylbutanoyl)-N-((R)-1-(2-fluorophenyl)ethyl)-1,2,3,4-tetrahydroisoquinoline-3-carboxamido)methyl)benzoate (90 mg, 0.13 mmol) in DCM (2 mL) was added TFA (0.5 mL, 6.49 mmol). The reaction mixture was stirred at rt for 1 h and concentrated in vacuo to give light brown solid (TFA salt, 90 mg, 59%), which was dried overnight under vacuum and used in the next step. MS(ESI$^+$) m/z 578.3 (M+H)$^+$.

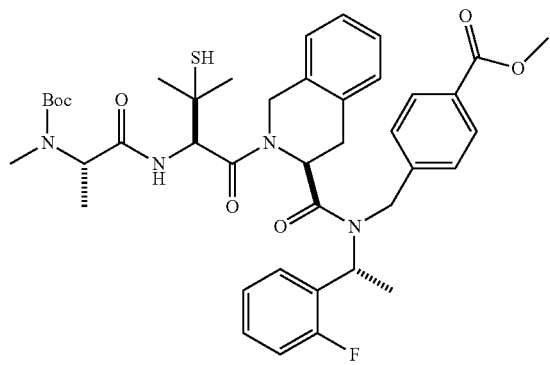

D) Methyl 4-(((S)-2-((R)-2-((S)-2-((tert-butoxycarbonyl)(methyl)amino)propanamido)-3-mercapto-3-methylbutanoyl)-N-((R)-1-(2-fluorophenyl)ethyl)-1,2,3,4-tetrahydroisoquinoline-3-carboxamido)methyl)benzoate To a solution of (S)-2-((tert-butoxycarbonyl)(methyl)amino)propanoic acid (34 mg, 0.17 mmol) in DMF (1 mL) were added EDC (35 mg, 0.18 mmol) and 3H-[1,2,3]-triazolo[4,5-b]pyridin-3-ol (20 mg, 0.14 mmol). The reaction mixture was stirred at rt for 10 minutes and treated with a solution of the crude methyl 4-(((S)-2-((R)-2-amino-3-mercapto-3-methylbutanoyl)-N-((R)-1-(2-fluorophenyl)ethyl)-1,2,3,4-tetrahydroisoquinoline-3-carboxamido)methyl)benzoate TFA salt (90 mg, 0.13 mmol) in DMF (1.5 mL) followed by DIEA (0.1 mL, 0.4 mmol). The resulting mixture was stirred at rt for 1 h and diluted with ethyl acetate and brine. The organic layer was separated and concentrated in vacuo. The residue was purified by preparative HPLC. Fractions containing the desired product were combined, concentrated, and lyophilized to give the title compound as a white solid (23 mg, 23%). MS(ESI$^+$) m/z 763.4 (M+H)$^+$.

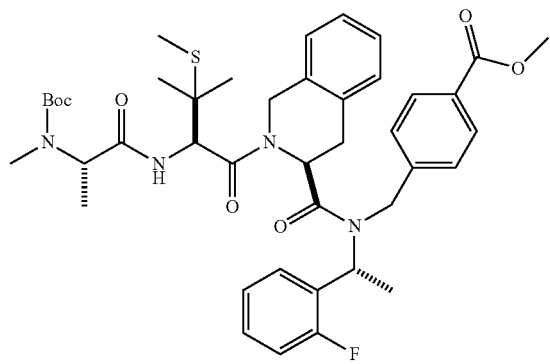

E) Methyl 4-(((S)-2-((R)-2-((S)-2-((tert-butoxycarbonyl)(methyl)amino)propanamido)-3-methyl-3-(methylthio)butanoyl)-N-((R)-1-(2-fluorophenyl)ethyl)-1,2,3,4-tetrahydroisoquinoline-3-carboxamido)methyl)benzoate To a solution of methyl 4-(((S)-2-((R)-2-((S)-2-((tert-butoxycarbonyl)(methyl)amino)propanamido)-3-mercapto-3-methylbutanoyl)-N-((R)-1-(2-fluorophenyl)ethyl)-1,2,3,4-tetrahydroisoquinoline-3-carboxamido)methyl)benzoate (23 mg, 0.03 mmol) in DCM (1 mL) was added iodomethane (0.04 mL, 0.60 mmol) and DIEA (11 µL, 0.06 mmol). The reaction mixture was stirred at rt for 30 minutes and concentrated in vacuo to give the title compound as a white solid, which was used directly in the next step without purification. MS(ESI$^+$) m/z 777.5 (M+H)$^+$.

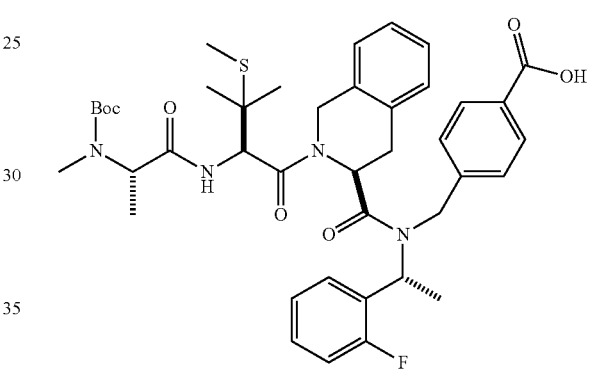

F) 4-(((S)-2-((R)-2-((S)-2-((tert-Butoxycarbonyl)(methyl)amino)propanamido)-3-methyl-3-(methylthio)butanoyl)-N-((R)-1-(2-fluorophenyl)ethyl)-1,2,3,4-tetrahydroisoquinoline-3-carboxamido)methyl)benzoic acid To a solution of methyl 4-(((S)-2-((R)-2-((S)-2-((tert-butoxycarbonyl)(methyl)amino)propanamido)-3-methyl-3-(methylthio)butanoyl)-N-((R)-1-(2-fluorophenyl)ethyl)-1,2,3,4-tetrahydroisoquinoline-3-carboxamido)methyl)benzoate (23 mg, 0.03 mmol) in THF (1 mL) and MeOH (0.5 mL) was added 2.0 M LiOH solution (0.3 mL, 0.59 mmol). The reaction mixture was stirred at rt for 3 h and treated with 1N HCl solution to adjust the pH of the solution to 1. The resulting mixture was extracted with ethyl acetate (twice) and dried over MgSO$_4$. The filtrate was concentrated in vacuo to give the title compound as a yellow solid (20 mg, 89%). MS(ESI$^+$) m/z 763.5 (M+H)$^+$.

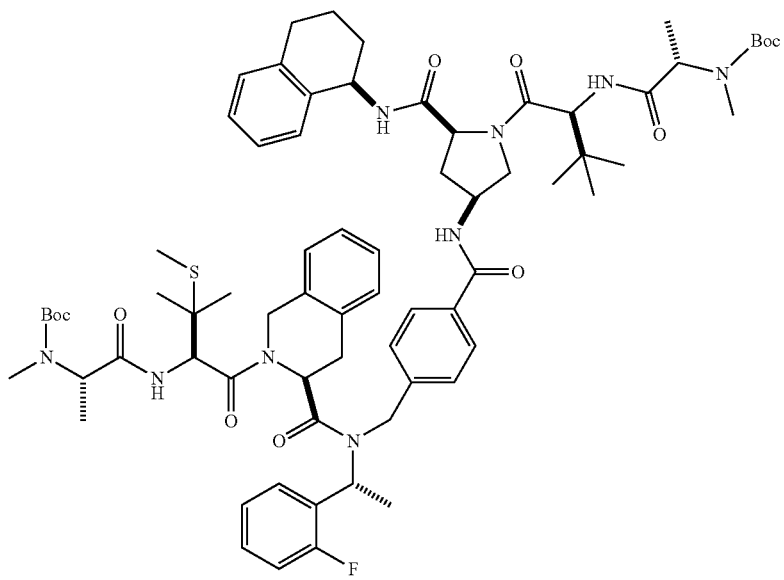

G) Intermediate III

To a solution of 4-(((S)-2-((R)-2-((S)-2-((tert-butoxycarbonyl)(methyl)amino)propanamido)-3-methyl-3-(methylthio)butanoyl)-N-((R)-1-(2-fluorophenyl)ethyl)-1,2,3,4-tetrahydroisoquinoline-3-carboxamido)methyl)benzoic acid (20 mg, 0.026 mmol) in DMF (1 mL) were added HATU (13 mg, 0.034 mmol), tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound K of Example 2, 17 mg, 0.03 mmol) and DIEA (0.02 mL, 0.13 mmol). The reaction mixture was stirred at rt for 1 h and purified by preparative HPLC. Fractions containing the desired product were combined, concentrated, and lyophilized to give the title compound as a white solid (17 mg, 50%). MS(ESI$^+$) m/z 1303.6 (M+H)$^+$.

H) (S)-N-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)ethyl)-2-((R)-3-methyl-2-((S)-2-(methylamino)propanamido)-3-(methylthio)butanoyl)-1,2,3,4-tetrahydroisoquinoline-3-carboxamide To a solution of Intermediate 3 (15 mg, 0.012 mmol) in DCM (1.5 mL) was added TFA (0.02 mL, 0.23 mmol). The reaction mixture was stirred at rt for 1 h, concentrated in vacuo and lyophilized to give the title compound as a white solid (2 TFA salt, 10 mg, 64%). MS(ESI$^+$) m/z 1102.7 (M+H)$^+$.

Evaluation of Biological Activity

Exemplary compounds were tested for inhibition of XIAP BIR3, XIAP BIR2 and/or XIAP BIR2-3 activity. Experimental procedures and results are provided below.

A. XIAP-BIR3 SMAC Peptide Fluorescence Polarization Assay (FPA)

Assays were performed in black, flat-bottom, 384-well plates. The final assay volume was 50 µL prepared from additions of N-His-Tb-BIR3(241-356, XIAP), fluoresceinated modified SMAC peptide, and test compounds in assay buffer consisting of 20 mM sodium phosphate, 1 mM EDTA, 50 mM NaCl, and 0.05% PLURONIC® F68. The reaction was incubated at room temperature for 60 minutes and fluorescence polarization of the reaction was detected on the LJL Plate Reader. Inhibition data were calculated from mP values generated by the no protein control reactions for 100% inhibition and vehicle-only reactions for 0% inhibition. The final concentration of reagents in the assay was 130 nM N-His-Tb-BIR3(241-356, XIAP), 1.4 nM fluoresceinated modified SMAC peptide, and 1% DMSO. Dose response curves were generated to determine the concentration required for inhibiting 50% of polarization activity ($IC_{50}$). Compounds were dissolved at 10 mM in dimethylsulfoxide (DMSO) and evaluated at eleven concentrations. $IC_{50}$ values were derived by non-linear regression analysis.

B. XIAP-BIR2/SMAC Peptide AlphaScreen Assay

Assays were performed in white, flat-bottom, 384-well ProxiPlates (Perkin Elmer). The final assay volume was 10 µL prepared from additions of His-BIR2 (124-240/C202A/C213G), Biotinylated SMAC peptide, and test compounds in assay buffer consisting of 25 mM Hepes, 100 mM NaCl, 0.1% BSA, and 5 mM $CaCl_2$. The reaction was incubated at room temperature for 60 minutes. After 60 minutes, 2.5 µL, of AlphaScreen detection reagent (Perkin Elmer) was added to the reaction mixture and incubated at room temperature in the dark for 120 minutes. The AlphaScreen signal generated by the reaction was detected on the Envision Plate Reader Inhibition data were calculated from an AlphaScreen signal generated by the no protein control reactions for 100% inhibition and vehicle-only reactions for 0% inhibition. The final concentration of reagents in the assay was 50 nM His-BIR2 (124-240/C202A/C213G), 50 nM.

Biotinylated SMAC peptide, 4 µg/mL AlphaScreen detection reagents, and 0.5% DMSO. Dose response curves were generated to determine the concentration required for inhibiting 50% of the activity ($IC_{50}$). Compounds were dissolved at 10 mM in dimethylsulfoxide (DMSO) and evaluated at eleven concentrations. $IC_{50}$ values were derived by non-linear regression analysis.

Results:

Results of the biochemical binding assays are shown in the Table below. "NT" means that the compound was not tested in the assay.

| Example No. | XIAP BIR3 FPA IC$_{50}$ (μM) | XIAP-BIR2 AlphaScreen IC$_{50}$ (μM) |
|---|---|---|
| 1 | 0.06 | 0.09 |
| 2 | 0.03 | 0.85 |
| 3 | 0.06 | 0.12 |
| 4 | 0.10 | 0.18 |
| 5 | 0.22 | 0.30 |
| 6 | 0.07 | 0.15 |
| 7 | 0.19 | 1.14 |
| 8 | 0.06 | 0.03 |
| 9 | 0.13 | 0.34 |
| 10 | 0.06 | 0.41 |
| 11 | 0.07 | 0.51 |
| 12 | 0.09 | 1.30 |
| 13 | 0.04 | 0.60 |
| 14 | 0.04 | 1.72 |
| 15 | 0.09 | 0.33 |
| 16 | 0.07 | 1.60 |
| 17 | 0.10 | 0.59 |
| 18 | 0.12 | 0.19 |
| 19 | 0.29 | 1.87 |
| 20 | 0.11 | 0.32 |
| 21 | 0.29 | 2.83 |
| 22 | 0.11 | 1.01 |
| 23 | 0.12 | 0.17 |
| 24 | 0.13 | 0.06 |
| 25 | 0.06 | 0.65 |
| 26 | 0.19 | 0.10 |
| 27 | 0.09 | 1.74 |
| 28 | 0.16 | 0.25 |
| 29 | 0.16 | 0.34 |
| 30 | 0.27 | 0.76 |
| 31 | 0.25 | 1.69 |
| 32 | 0.06 | 0.80 |
| 33 | 0.12 | 0.90 |
| 34 | 0.16 | 1.57 |
| 35 | 0.23 | 1.81 |
| 36 | 0.09 | 1.29 |
| 37 | 0.23 | 0.65 |
| 38 | 0.06 | 0.22 |
| 39 | 0.08 | 0.32 |
| 40 | 0.06 | 1.21 |
| 41 | 0.06 | 0.11 |
| 42 | 0.07 | 0.33 |
| 43 | 0.18 | 0.15 |

What is claimed is:

1. A compound selected from the following (S)-N-(4-(((3S,5S)-1-((S)-3,3-Dimethyl-2-((R)-2-(methylamino)propanamido)butanoyl)-5-(((R)-1,2,3,4-tetrahydronaphthalen-1-yl)carbamoyl)pyrrolidin-3-yl)carbamoyl)benzyl)-2-((S)-3,3-dimethyl-2-((S)-2-(methylamino)propanamido)butanoyl)-N-((R)-1-(2-fluorophenyl)ethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-phenethyl-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(3-methoxyphenyl)ethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(4-fluorophenyl)ethyl)-1,2,3,4-tetrahydroisoquinoline-3-carboxamide, (S)-N-((R)-1-(2-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, (S)-N-((R)-1-(2,3-Difluorophenyl)ethyl)-2-((S)-3,3-dimethyl-2)-((S)-2-(methylamino)propanamido)butanoyl)-N-(4-(((3S,5S)-1-((S)-3,3-dimethyl-2-((S))-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-phenylbutyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-2-methoxy-1-phenylethyl)-1,2,3,4-tetrahydroisoquinoline-3-carboxamide, (S)-N-(2,3-Dichlorobenzyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, (S)-2-((S)-3,3-Dimethyl-2-2-(methylamino)propanamido)butanoyl)-N-(4-(((3S,5S)-1-((S)-3,3-dimethyl-2-2-(methylamino)propanamido)butanoyl)-5-(((R)-1,2,3,4-tetrahydronaphthalen- 1-yl)carbamoyl)pyrrolidin-3-yl)carbamoyl)benzyl)-N-(2-(naphthalen-2-yl)ethyl)-1,2,3,4-tetrahydroisoquinoline-3-carboxamide, (S)-N-Benzyl-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-(naphthalen-2-ylmethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-

(naphthalen-2-yl)ethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-phenethyl-1,2,3,4-tetrahydroisoquinoline-1-carboxamide, (S)-N-((S)-1-(3-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)ethyl)-1,2,3,4-tetrahydroisoquinoline-1-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)- 1,2,3,4-tetrahydronaphthalen-1-yl)carbamoyl)pyrrolidin-3-yl)carbamoyl)benzyl)-N-((R)-1-phenylpropyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1,1-diphenylpropan-2-yl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((S)-1,2,3,4-tetrahydronaphthalen-1-yl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-phenylethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-methoxyphenyl)ethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)propan-2-yl)-1,2,3,4-tetrahydroisoquinoline-3-carboxamide, (3S)-N-(1-(2-Chlorophenyl)ethyl)-2-((S)-3,3-dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-fluorophenyl)propan-2-yl)-1,2,3,4-tetrahydroisoquinoline-1-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(o-tolyl)ethyl)-1,2,3,4-tetrahydroisoquinoline-3-carboxamide, (S)-2-((S)-3,3-Dimethyl-2-((S)-2-(methylamino)propanamido)butanoyl)-N-(4-(((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)-N-((R)-1-(2-ethoxyphenyl)ethyl)-1,2,3,4-tetrahydroisoquinoline-3-carboxamide, or a pharmaceutically acceptable salt, tautomer or stereoisomer thereof.

* * * * *